US010422002B2

(12) United States Patent
Stephens et al.

(10) Patent No.: US 10,422,002 B2
(45) Date of Patent: Sep. 24, 2019

(54) METHODS AND COMPOSITIONS FOR DNA PROFILING

(71) Applicant: Illumina, Inc., San Diego, CA (US)

(72) Inventors: Kathryn M. Stephens, Poway, CA (US); Cydne Holt, Encinitas, CA (US); Carey Davis, San Diego, CA (US); Anne Jager, San Diego, CA (US); Paulina Walichiewicz, San Diego, CA (US); Yonmee Han, San Diego, CA (US); David Silva, San Diego, CA (US); Min-Jui Richard Shen, Poway, CA (US); Sasan Amini, San Diego, CA (US); Frank J. Steemers, Encinitas, CA (US)

(73) Assignee: ILLUMINA, INC., San Diego, CA (US)

( * ) Notice: Subject to any disclaimer, the term of this patent is extended or adjusted under 35 U.S.C. 154(b) by 581 days.

(21) Appl. No.: 14/622,632

(22) Filed: Feb. 13, 2015

(65) Prior Publication Data

US 2015/0232929 A1    Aug. 20, 2015

Related U.S. Application Data

(60) Provisional application No. 61/940,942, filed on Feb. 18, 2014, provisional application No. 62/043,060, filed on Aug. 28, 2014, provisional application No. 62/103,524, filed on Jan. 14, 2015.

(51) Int. Cl.
| | |
|---|---|
| *C12Q 1/6876* | (2018.01) |
| *C12Q 1/6827* | (2018.01) |
| *C12Q 1/6853* | (2018.01) |
| *C12Q 1/6858* | (2018.01) |
| *C12Q 1/6869* | (2018.01) |

(52) U.S. Cl.
CPC ......... *C12Q 1/6876* (2013.01); *C12Q 1/6827* (2013.01); *C12Q 1/6853* (2013.01); *C12Q 1/6858* (2013.01); *C12Q 1/6869* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2003/0082566 A1* | 5/2003 | Sylvan | ................. | C12Q 1/6858 435/6.1 |
| 2003/0157499 A1* | 8/2003 | Lundeberg | ........... | C12Q 1/6851 435/5 |
| 2006/0014190 A1* | 1/2006 | Hennessy | ............. | C12Q 1/6827 435/6.11 |
| 2006/0057595 A1* | 3/2006 | Lao | ...................... | C12Q 1/6851 435/6.12 |
| 2008/0090239 A1* | 4/2008 | Shoemaker | ........ | G01N 33/5091 435/6.12 |
| 2009/0081675 A1* | 3/2009 | Colston, Jr. | ............ | C12Q 1/689 435/6.18 |
| 2009/0163366 A1* | 6/2009 | Nickerson | ............ | C12Q 1/6869 506/4 |
| 2009/0317817 A1* | 12/2009 | Oeth | .................... | C12Q 1/6879 435/6.11 |

FOREIGN PATENT DOCUMENTS

| | | |
|---|---|---|
| WO | WO 2006/004659 A1 | 1/2006 |
| WO | 2011091046 | 7/2011 |
| WO | WO 2012/155084 A1 | 11/2012 |

OTHER PUBLICATIONS

Dieffenbach et al. Genome Research 1993; 3: S30-S37.*
Kinde et al. Proceedings of the National Academy of Sciences, USA 2011; 108: 9530-9535. (Year: 2011).*
Kube et al. Genes and Immunity 2003; 4: 459-468. (Year: 2003).*
Rook MS et al., Whole genome amplification of DNA from laser capture-microdissected tissue for high-throughput single nucleotide polymorphism and short tandem repeat genotyping, American Journal of Pathology 164:23-33 (2004).
Fraige Karina et al., Analysis of Seven STR Human Loci for Paternity Testing by Microchip Electrophoresis, Brazilian Archives of Biology and Technology 56:213-221 (2013).
Teemu Kivioja et al., Counting absolute numbers of molecules using unique molecular identifiers, Nature Methods, Nature Publishing Group, GB 9:72-74 (2012).
Liu Jing et al., An Improved allele-specific PCR primer design method for SNP marker analysis and its application, Plant Methods, Biomed Central, London, GB, 8:1-8 (2012).
Phillips Chris et al., Development of a novel forensic STR multiplex for ancestry analysis and extended identity testing, Electrophoresis, 34:1151-1162 (2013).

(Continued)

*Primary Examiner* — Angela M. Bertagna
(74) *Attorney, Agent, or Firm* — Illumina, Inc.

(57) ABSTRACT

Embodiments disclosed herein provide methods for constructing a DNA profile comprising: providing a nucleic acid sample, amplifying the nucleic acid sample with a plurality of primers that specifically hybridize to at least one target sequence comprising a SNP and at least one target sequence comprising a tandem repeat, and determining the genotypes of the at least one SNP and at least one tandem repeat in the amplification products, thereby constructing the DNA profile of the nucleic acid sample. Embodiments disclosed herein further provide a plurality of primers that specifically hybridize to at least one short target sequence and at least one long target sequence in a nucleic acid sample, wherein amplifying the nucleic acid sample using the plurality of primers in a single reaction results in a short amplification product and a long amplification product, wherein each of the plurality of primers comprises one or more tag sequences.

10 Claims, 36 Drawing Sheets

Specification includes a Sequence Listing.

(56) References Cited

OTHER PUBLICATIONS

Bornman Daniel et al., Short-read, high-throughput sequencing technology for STR genotyping, Biotech Rapid Dispatches 2012:1-6 (2012).
Bender K et al., A multiplex SNP typing approach for the DNA pyrosequencing technology, International Congress Series 1288:73-75 (2006).
International Search Report and Written Opinion dated May 13, 2015 for PCT Application No. PCT/US2015/015939, filed Feb. 13, 2015.
"Office Action", Office Action, Columbian Patent Application No. NC2016/0001634, dated Feb. 9, 2018, 10 pages.

* cited by examiner

FIG. 1
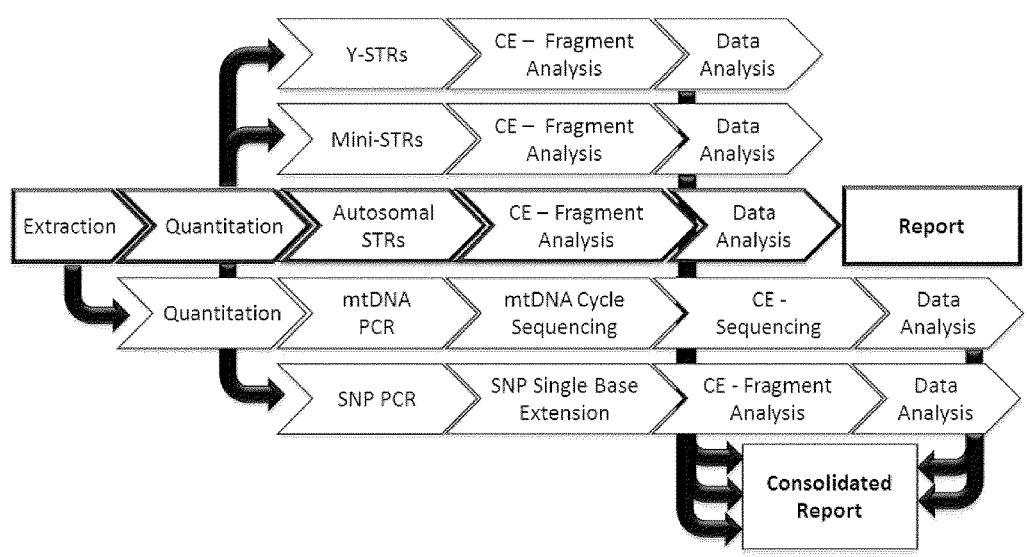
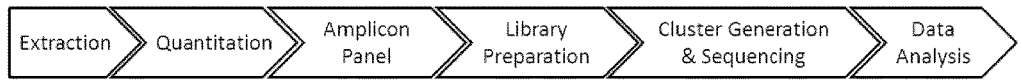

FIG. 5
A
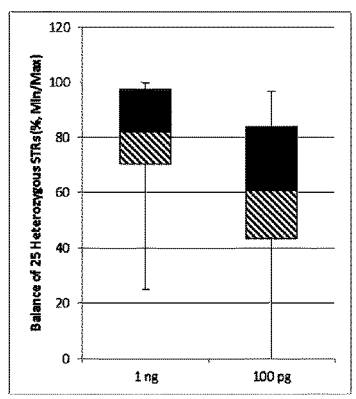
B
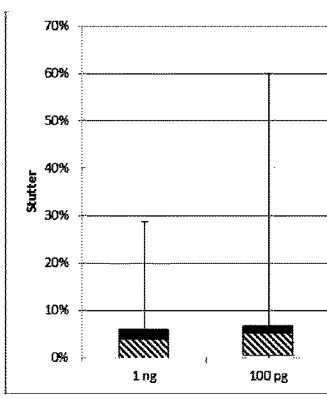
C
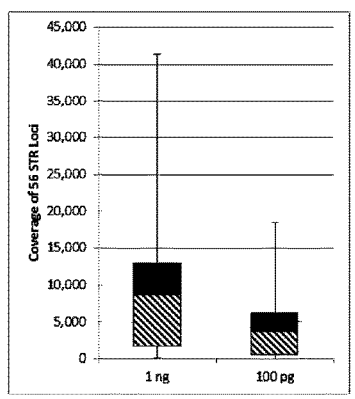
D
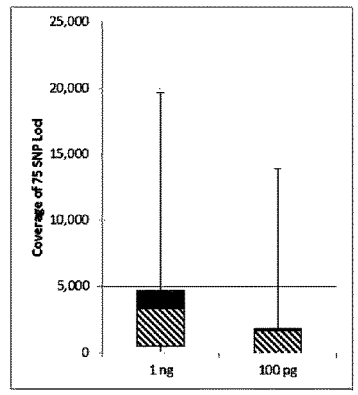
E
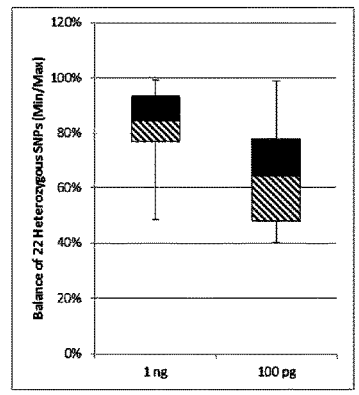

FIG. 7
A
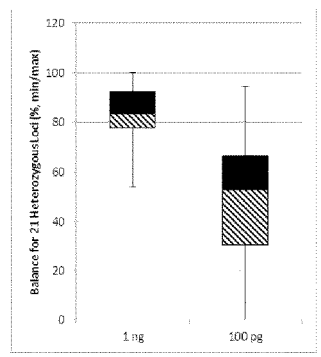
B
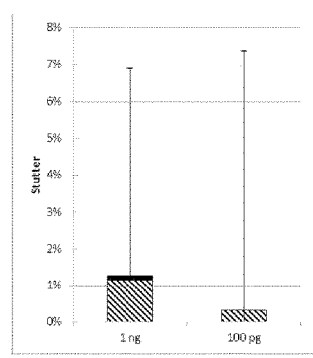
C
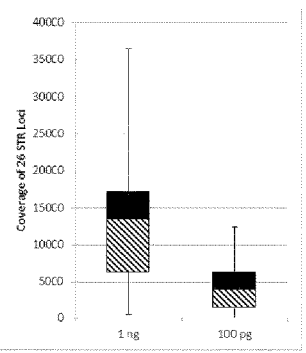
D
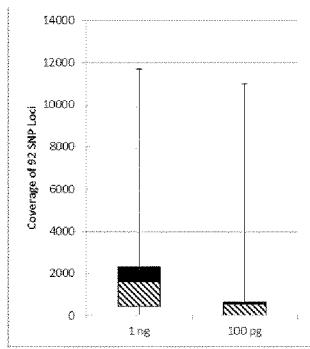
E
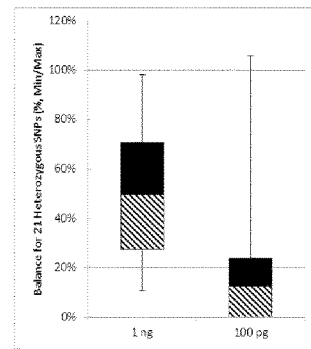

FIG. 10
A
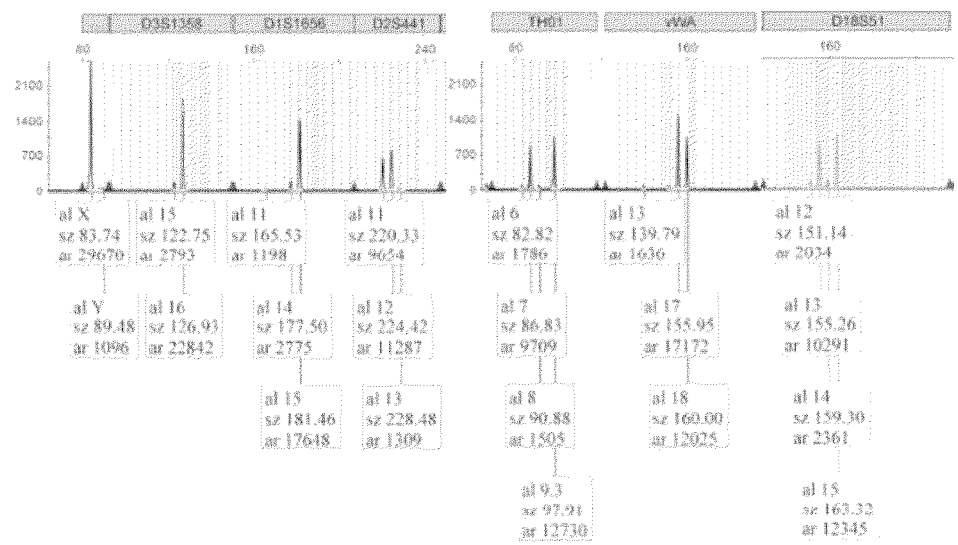
B
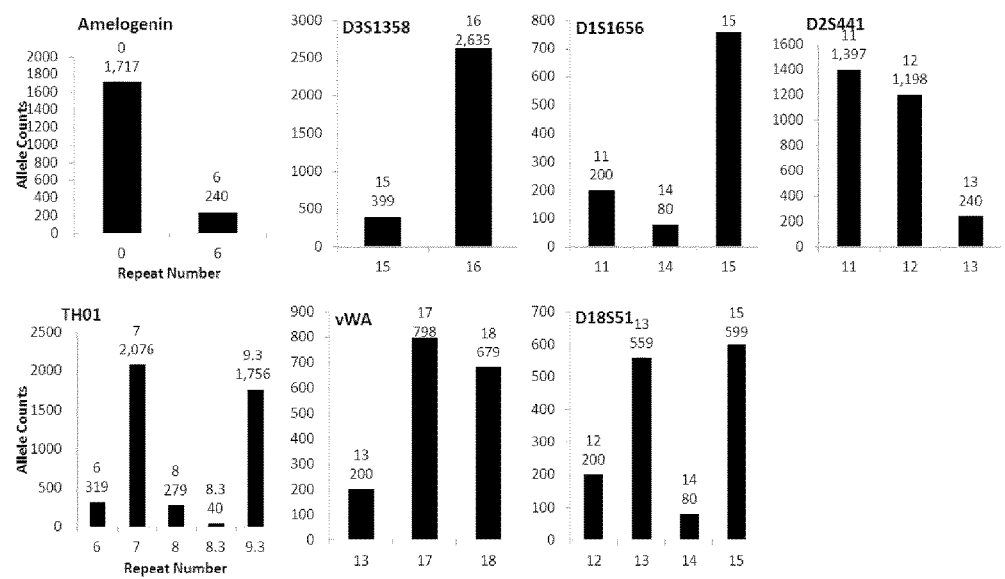

| | Sex (Amelogenin) | | Reads aligned to STRs | | Reads aligned to SNPs | | # STR Loci Called | | # SNP Loci Called | |
|---|---|---|---|---|---|---|---|---|---|---|
| | Rep 1 | Rep 2 | Rep 1 | Rep 2 | Rep 1 | Rep 2 | Rep 1 | Rep 2 | Rep 1 | Rep 2 |
| Sample 1 | X,Y | X,Y | 203068 | 248442 | 149466 | 181778 | 61 | 61 | 173 | 173 |
| Sample 3 | X | X | 216055 | 257742 | 212633 | 240954 | 37 | 37 | 173 | 173 |
| Sample 4 | X,Y | X,Y | 207488 | 205907 | 178985 | 169305 | 60 | 60 | 173 | 173 |
| Sample 5 | X | X | 199073 | 248681 | 205600 | 252732 | 37 | 37 | 173 | 173 |
| Sample 6 | X,Y | X,Y | 257850 | 281531 | 108997 | 129134 | 61 | 61 | 173 | 173 |
| Sample 7 | X,Y | X,Y | 312646 | 273206 | 156677 | 120709 | 61 | 61 | 173 | 173 |
| Sample 10 | X | X | 182882 | 321643 | 130252 | 235847 | 37 | 37 | 173 | 173 |
| Sample 13 | X | X | 266863 | 319394 | 183128 | 207556 | 37 | 37 | 173 | 173 |
| Sample 14 | X | X | 257545 | 180804 | 221688 | 155998 | 37 | 37 | 173 | 173 |
| Sample 15 | X,Y | X,Y | 232712 | 251490 | 150815 | 184715 | 37 | 37 | 173 | 173 |
| Sample 16 | X,Y | X,Y | 275702 | 213553 | 176862 | 126154 | 61 | 60 | 173 | 173 |
| Sample 17 | X | X | 159708 | 235314 | 106760 | 193307 | 37 | 37 | 173 | 173 |
| 2800M | X,Y | X,Y | 327295 | 0 | 125254 | 0 | 61 | 0 | 173 | 0 |
| NTC | NA | NA | 0 | 0 | 0 | 0 | 0 | 0 | 0 | 0 |

FIG. 12

| Sample | NIST Auto-STRs RMP | NIST Y-STRs 95% confidence HaplotypeFrequency | dbSNP iSNPs RMP | US Y-STR DB (match probability) |
|---|---|---|---|---|
| Sample 1 | 1.05E-36 | 8.32E-03 | 3.98E-45 | -2.58 |
| Sample 3 | 4.90E-33 | | 2.51E-46 | |
| Sample 4 | 7.41E-37 | 8.32E-03 | 7.94E-41 | -2.58 |
| Sample 5 | 2.82E-37 | | 1.00E-43 | |
| Sample 6 | 1.45E-34 | 8.32E-03 | 6.31E-45 | -2.58 |
| Sample 7 | 4.17E-36 | 8.32E-03 | 1.58E-42 | |
| Sample 10 | 3.55E-38 | | 3.98E-44 | |
| Sample 13 | 1.58E-37 | | 7.94E-43 | |
| Sample 14 | 2.00E-37 | | 1.26E-44 | |
| Sample 15 | 8.71E-38 | | 1.58E-40 | |
| Sample 16 | 6.03E-42 | 8.32E-03 | 1.26E-44 | -2.58 |
| Sample 17 | 4.07E-34 | | 7.94E-46 | |
| 2800M | 5.75E-33 | 8.32E-03 | 1.58E-44 | -2.58 |

FIG. 13

| | Predictions | | | | | | | | Donor Characteristics | |
|---|---|---|---|---|---|---|---|---|---|---|
| | Eye Color | | | Hair Color | | | | | Eye Color | Hair Color |
| | blue | intermediate | brown | brown | red | black | blond | light | dark | | |
| Sample 1 | 8% | 14% | 79% | 47% | 0% | 12% | 41% | 74% | 26% | Brown | Brown |
| Sample 3 | 0% | 1% | 99% | 35% | 0% | 63% | 3% | 3% | 97% | Brown | Dark Brown |
| Sample 4 | 1% | 3% | 97% | 30% | 0% | 68% | 2% | 3% | 97% | Brown | Black |
| Sample 5 | 2% | 23% | 75% | 79% | 4% | 8% | 10% | 60% | 40% | Hazel | Brown |
| Sample 6 | 3% | 6% | 91% | 66% | 0% | 18% | 16% | 54% | 46% | Brown | Brown |
| Sample 7 | 0% | 0% | 100% | 6% | 0% | 94% | 0% | 0% | 100% | Dark Brown | Black |
| Sample 10 | 49% | 22% | 29% | 36% | 0% | 14% | 50% | 82% | 18% | Blue | Brown/Blonde |
| Sample 13 | 0% | 1% | 99% | 32% | 0% | 67% | 1% | 2% | 98% | Dark Brown | Black |
| Sample 14 | 2% | 9% | 88% | 60% | 1% | 34% | 4% | 10% | 90% | Dark Brown | Dark Brown |
| Sample 15 | 1% | 4% | 95% | 33% | 0% | 66% | 0% | 0% | 100% | Dark Brown | Dark Brown |
| Sample 16 | 0% | 0% | 100% | 16% | 0% | 84% | 0% | 0% | 100% | Dark Brown | Black |
| Sample 17 | 85% | 8% | 6% | 63% | 8% | 11% | 19% | 62% | 38% | Blue | Light Brown/Blonde |
| 2800M | 5% | 12% | 83% | 43% | 0% | 5% | 52% | 88% | 12% | | |

*FIG. 14*

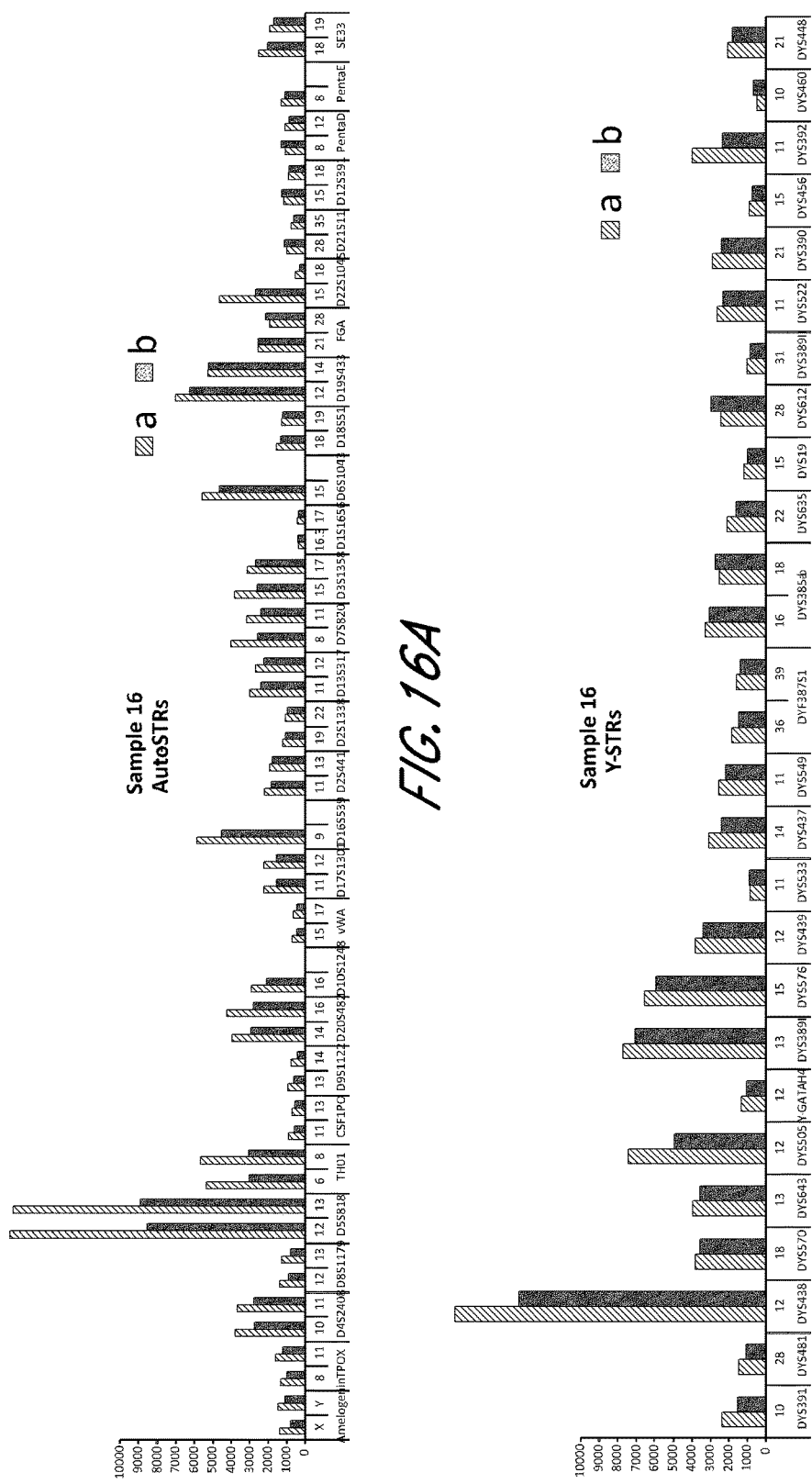

| Sample ID | Locus | Repeat Number | Sequence | % | % |
|---|---|---|---|---|---|
| Sample 3 | D9S1122 | 13 | TAGATAGATAGATAGATAGATAGATAGATAGATAGATAGATAGATAGATAGA | 52% | 48% |
| | | | TAGATCGATAGATAGATAGATAGATAGATAGATAGATAGATAGATAGATAGA | | |
| Sample 7 | D2S1338 | 19 | TGCCTGCCTGCCTGCCTGCCTGCCTGCCTGCCTTCCTTCCTTCCTTCCTTCCTTCCTTCCTTCCTTCCTTCC | 54% | 46% |
| | | | TGCCTGCCTGCCTGCCTGCCTGCCTGCCTGCCGCCTTCCTTCCTTCCTTCCTTCCTTCCTTCCTTCCTTCC | | |
| Sample 13 | D8S1179 | 14 | TCTATCTATCTGTCTATCTATCTATCTATCTATCTATCTATCTATCTATCTA | 52% | 48% |
| | | | TCTATCGTCTATCTATCTATCTATCTATCTATCTATCTATCTATCTATCTA | | |
| Sample 14 | D8S1179 | 13 | TCTATCATCTGTCTATCTATCTATCTATCTATCTATCTATCTATCTATCTA | 58% | 42% |
| | | | TCTATCGTCTATCTATCTATCTATCTATCTATCTATCTATCTATCTATCTA | | |
| Sample 15 | D2S1338 | 19 | TGCCTGCCTGCCTGCCTGCCTGCCTGCCTGCCGCCTTCCTTCCTTCCTTCCTTCCTTCCTTCCTTCCTTCC | 57% | 43% |
| | | | TGCCTGCCTGCCTGCCTGCCTGCCTGCCTGCCTTCCTTCCTTCCTTCCTTCCTTCCTTCCTTCCTTCCTTCC | | |
| Sample 17 | D8S1179 | 13 | TCTATCATCTATCTATCTATCTATCTATCTATCTATCTATCTATCTATCTA | 55% | 45% |
| | | | TCTATCGTCTATCTATCTATCTATCTATCTATCTATCTATCTATCTATCTA | | |
| Sample 17 | D9S1122 | 12 | TAGATAGATAGATAGATAGATAGATAGATAGATAGATAGATAGATAGA | 52% | 48% |
| | | | TAGATCGATAGATAGATAGATAGATAGATAGATAGATAGATAGATAGA | | |
| 2800M | D9S1122 | 12 | TAGATAGATAGATAGATAGATAGATAGATAGATAGATAGATAGATAGA | 50% | 50% |
| | | | TAGATCGATAGATAGATAGATAGATAGATAGATAGATAGATAGATAGA | | |

| Sample | STRs called | iSNPs called | Dropped STR alleles | Dropped SNP alleles | RMP* |
|---|---|---|---|---|---|
| Male Control | 60 | 94 | None | None | 1 in 5.6E+28 |
| Male, Sheared | 45/60 | 93/94 | 5 | 3 | 1 in 2.3E+28 |
| Male, Sheared+DNase | 28/60 | 81/94 | 5 | 8 | 1 in 5.0E+19 |
| Female Control | 36 | 94 | None | None | 1 in 1.7E+29 |
| Female, Sheared | 32/36 | 92/94 | 7 | 3 | 1 in 3.11E+28 |
| Female, Sheared | 21/36 | 77/94 | 11 | 17 | 1 in 1.41E+16 | ns and compositions for DNA

```
                        SEQUENCE LISTING

<160> NUMBER OF SEQ ID NOS: 429

<210> SEQ ID NO 1
<211> LENGTH: 19
<212> TYPE: DNA
<213> ORGANISM: Homo sapiens

<400> SEQUENCE: 1
ccctgggctc tgtaaagaa                                                  19

<210> SEQ ID NO 2
<211> LENGTH: 24
<212> TYPE: DNA
<213> ORGANISM: Homo sapiens

<400> SEQUENCE: 2
atcagagctt aaactgggaa gctg                                            24

<210> SEQ ID NO 3
<211> LENGTH: 23
<212> TYPE: DNA
<213> ORGANISM: Homo sapiens

<400> SEQUENCE: 3
acagtaactg ccttcataga tag                                             23

<210> SEQ ID NO 4
<211> LENGTH: 22
<212> TYPE: DNA
<213> ORGANISM: Homo sapiens

<400> SEQUENCE: 4
gtgtcagacc ctgttctaag ta                                              22

<210> SEQ ID NO 5
<211> LENGTH: 30
<212> TYPE: DNA
<213> ORGANISM: Homo sapiens

<400> SEQUENCE: 5
tgattttcct ctttggtatc cttatgtaat                                      30
```

```
<210> SEQ ID NO 6
<211> LENGTH: 28
<212> TYPE: DNA
<213> ORGANISM: Homo sapiens

<400> SEQUENCE: 6
acaacatttg tatctttatc tgtatcct                                          28

<210> SEQ ID NO 7
<211> LENGTH: 27
<212> TYPE: DNA
<213> ORGANISM: Homo sapiens

<400> SEQUENCE: 7
tttgtatttc atgtgtacat tcgtatc                                           27

<210> SEQ ID NO 8
<211> LENGTH: 28
<212> TYPE: DNA
<213> ORGANISM: Homo sapiens

<400> SEQUENCE: 8
acctatcctg tagattattt tcactgtg                                          28

<210> SEQ ID NO 9
<211> LENGTH: 24
<212> TYPE: DNA
<213> ORGANISM: Homo sapiens

<400> SEQUENCE: 9
ctctgagtga caaattgaga cctt                                              24

<210> SEQ ID NO 10
<211> LENGTH: 25
<212> TYPE: DNA
<213> ORGANISM: Homo sapiens

<400> SEQUENCE: 10
ttaacttctc tggtgtgtgg agatg                                             25

<210> SEQ ID NO 11
<211> LENGTH: 20
<212> TYPE: DNA
<213> ORGANISM: Homo sapiens

<400> SEQUENCE: 11
tttggtgcac ccattacccg                                                   20

<210> SEQ ID NO 12
<211> LENGTH: 20
<212> TYPE: DNA
<213> ORGANISM: Homo sapiens

<400> SEQUENCE: 12
aggaggttga ggctgcaaaa                                                   20

<210> SEQ ID NO 13
<211> LENGTH: 35
<212> TYPE: DNA
<213> ORGANISM: Homo sapiens

<400> SEQUENCE: 13
caccaaatat tggtaattaa atgtttacta tagac                                  35
```

<210> SEQ ID NO 14
<211> LENGTH: 25
<212> TYPE: DNA
<213> ORGANISM: Homo sapiens

<400> SEQUENCE: 14
taaagggtat gatagaacac ttgtc                                    25

<210> SEQ ID NO 15
<211> LENGTH: 21
<212> TYPE: DNA
<213> ORGANISM: Homo sapiens

<400> SEQUENCE: 15
caaaggcaga tcccaagctc t                                        21

<210> SEQ ID NO 16
<211> LENGTH: 21
<212> TYPE: DNA
<213> ORGANISM: Homo sapiens

<400> SEQUENCE: 16
tgtgtgtgca tctgtaagca t                                        21

<210> SEQ ID NO 17
<211> LENGTH: 20
<212> TYPE: DNA
<213> ORGANISM: Homo sapiens

<400> SEQUENCE: 17
tggtgtgtat tccctgtgcc                                          20

<210> SEQ ID NO 18
<211> LENGTH: 20
<212> TYPE: DNA
<213> ORGANISM: Homo sapiens

<400> SEQUENCE: 18
gcagtccaat ctgggtgaca                                          20

<210> SEQ ID NO 19
<211> LENGTH: 28
<212> TYPE: DNA
<213> ORGANISM: Homo sapiens

<400> SEQUENCE: 19
ccaatctggt cacaaacata ttaatgaa                                 28

<210> SEQ ID NO 20
<211> LENGTH: 27
<212> TYPE: DNA
<213> ORGANISM: Homo sapiens

<400> SEQUENCE: 20
tttcccttgt cttgttatta aaggaac                                  27

<210> SEQ ID NO 21
<211> LENGTH: 20
<212> TYPE: DNA
<213> ORGANISM: Homo sapiens

<400> SEQUENCE: 21
ttcccattgg cctgttcctc                                          20

```
<210> SEQ ID NO 22
<211> LENGTH: 20
<212> TYPE: DNA
<213> ORGANISM: Homo sapiens

<400> SEQUENCE: 22
ctgtacacag ggcttccgag                                                    20

<210> SEQ ID NO 23
<211> LENGTH: 23
<212> TYPE: DNA
<213> ORGANISM: Homo sapiens

<400> SEQUENCE: 23
gctgagtgat tgtctgtaa ttg                                                 23

<210> SEQ ID NO 24
<211> LENGTH: 37
<212> TYPE: DNA
<213> ORGANISM: Homo sapiens

<400> SEQUENCE: 24
gaactcacag attaaactgt aaccaaaata aaattag                                 37

<210> SEQ ID NO 25
<211> LENGTH: 22
<212> TYPE: DNA
<213> ORGANISM: Homo sapiens

<400> SEQUENCE: 25
caatagtgtg caaggatggg tg                                                 22

<210> SEQ ID NO 26
<211> LENGTH: 20
<212> TYPE: DNA
<213> ORGANISM: Homo sapiens

<400> SEQUENCE: 26
tctgtggttc tccagcttac                                                    20

<210> SEQ ID NO 27
<211> LENGTH: 22
<212> TYPE: DNA
<213> ORGANISM: Homo sapiens

<400> SEQUENCE: 27
cttagggaac cctcactgaa tg                                                 22

<210> SEQ ID NO 28
<211> LENGTH: 22
<212> TYPE: DNA
<213> ORGANISM: Homo sapiens

<400> SEQUENCE: 28
gtccttgtca gcgtttattt gc                                                 22

<210> SEQ ID NO 29
<211> LENGTH: 20
<212> TYPE: DNA
<213> ORGANISM: Homo sapiens

<400> SEQUENCE: 29
```
ttgggttgag ccataggcag                                               20

<210> SEQ ID NO 30
<211> LENGTH: 20
<212> TYPE: DNA
<213> ORGANISM: Homo sapiens

<400> SEQUENCE: 30
gcatccgtga ctctctggac                                               20

<210> SEQ ID NO 31
<211> LENGTH: 26
<212> TYPE: DNA
<213> ORGANISM: Homo sapiens

<400> SEQUENCE: 31
gttatgggac ttttctcagt ctccat                                        26

<210> SEQ ID NO 32
<211> LENGTH: 27
<212> TYPE: DNA
<213> ORGANISM: Homo sapiens

<400> SEQUENCE: 32
gagactaata ggaggtagat agactgg                                       27

<210> SEQ ID NO 33
<211> LENGTH: 24
<212> TYPE: DNA
<213> ORGANISM: Homo sapiens

<400> SEQUENCE: 33
gagactgtat tagtaaggct tctc                                          24

<210> SEQ ID NO 34
<211> LENGTH: 20
<212> TYPE: DNA
<213> ORGANISM: Homo sapiens

<400> SEQUENCE: 34
cctggactga gccatgctcc                                               20

<210> SEQ ID NO 35
<211> LENGTH: 23
<212> TYPE: DNA
<213> ORGANISM: Homo sapiens

<400> SEQUENCE: 35
cagtcctgtg ttagtcagga ttc                                           23

<210> SEQ ID NO 36
<211> LENGTH: 22
<212> TYPE: DNA
<213> ORGANISM: Homo sapiens

<400> SEQUENCE: 36
tcaagggtca actgtgtgat gt                                            22

<210> SEQ ID NO 37
<211> LENGTH: 24
<212> TYPE: DNA
<213> ORGANISM: Homo sapiens

<400> SEQUENCE: 37

-continued

```
cttctgaaag cttctagttt acct                                          24

<210> SEQ ID NO 38
<211> LENGTH: 24
<212> TYPE: DNA
<213> ORGANISM: Homo sapiens

<400> SEQUENCE: 38
ttgcttattt gtggggtat ttca                                           24

<210> SEQ ID NO 39
<211> LENGTH: 29
<212> TYPE: DNA
<213> ORGANISM: Homo sapiens

<400> SEQUENCE: 39
aagaattctc ttatttgggt tattaattg                                     29

<210> SEQ ID NO 40
<211> LENGTH: 20
<212> TYPE: DNA
<213> ORGANISM: Homo sapiens

<400> SEQUENCE: 40
aaattgtgga caggtgcggt                                               20

<210> SEQ ID NO 41
<211> LENGTH: 34
<212> TYPE: DNA
<213> ORGANISM: Homo sapiens

<400> SEQUENCE: 41
ccatgtaaaa atacatgcat gtgtttattt atac                               34

<210> SEQ ID NO 42
<211> LENGTH: 35
<212> TYPE: DNA
<213> ORGANISM: Homo sapiens

<400> SEQUENCE: 42
tgattaaaaa gaatgaaggt aaaaatgtgt ataac                              35

<210> SEQ ID NO 43
<211> LENGTH: 34
<212> TYPE: DNA
<213> ORGANISM: Homo sapiens

<400> SEQUENCE: 43
ccaaatgttt atgattaatc ttttaaattg gagc                               34

<210> SEQ ID NO 44
<211> LENGTH: 26
<212> TYPE: DNA
<213> ORGANISM: Homo sapiens

<400> SEQUENCE: 44
gtaacaaggg ctacaggaat catgag                                        26

<210> SEQ ID NO 45
<211> LENGTH: 27
<212> TYPE: DNA
<213> ORGANISM: Homo sapiens
```

<400> SEQUENCE: 45
tcatccactg aaatgactga aaaatag                                27

<210> SEQ ID NO 46
<211> LENGTH: 25
<212> TYPE: DNA
<213> ORGANISM: Homo sapiens

<400> SEQUENCE: 46
aggtacataa cagttcaata gaaag                                 25

<210> SEQ ID NO 47
<211> LENGTH: 29
<212> TYPE: DNA
<213> ORGANISM: Homo sapiens

<400> SEQUENCE: 47
gagttattca gtaagttaaa ggattgcag                             29

<210> SEQ ID NO 48
<211> LENGTH: 24
<212> TYPE: DNA
<213> ORGANISM: Homo sapiens

<400> SEQUENCE: 48
gggagccagt ggatttggaa acag                                  24

<210> SEQ ID NO 49
<211> LENGTH: 20
<212> TYPE: DNA
<213> ORGANISM: Homo sapiens

<400> SEQUENCE: 49
gcatggtgag gctgaagtag                                       20

<210> SEQ ID NO 50
<211> LENGTH: 25
<212> TYPE: DNA
<213> ORGANISM: Homo sapiens

<400> SEQUENCE: 50
ctaacctatg gtcataacga tttttt                                25

<210> SEQ ID NO 51
<211> LENGTH: 30
<212> TYPE: DNA
<213> ORGANISM: Homo sapiens

<400> SEQUENCE: 51
gatgataaga ataatcagta tgtgacttgg                            30

<210> SEQ ID NO 52
<211> LENGTH: 30
<212> TYPE: DNA
<213> ORGANISM: Homo sapiens

<400> SEQUENCE: 52
ataggttaga tagagatagg acagatgata                            30

<210> SEQ ID NO 53
<211> LENGTH: 22
<212> TYPE: DNA
<213> ORGANISM: Homo sapiens -continued

```
<400> SEQUENCE: 53
ccctaccgct atagtaactt gc                                          22

<210> SEQ ID NO 54
<211> LENGTH: 23
<212> TYPE: DNA
<213> ORGANISM: Homo sapiens

<400> SEQUENCE: 54
cacgtctgta attccagctc cta                                         23

<210> SEQ ID NO 55
<211> LENGTH: 25
<212> TYPE: DNA
<213> ORGANISM: Homo sapiens

<400> SEQUENCE: 55
ggaagcgtgt actagagttc ttcag                                       25

<210> SEQ ID NO 56
<211> LENGTH: 22
<212> TYPE: DNA
<213> ORGANISM: Homo sapiens

<400> SEQUENCE: 56
ggacagcctc catatccaca tg                                          22

<210> SEQ ID NO 57
<211> LENGTH: 23
<212> TYPE: DNA
<213> ORGANISM: Homo sapiens

<400> SEQUENCE: 57
ttcctactgc cccacctta ttg                                          23

<210> SEQ ID NO 58
<211> LENGTH: 24
<212> TYPE: DNA
<213> ORGANISM: Homo sapiens

<400> SEQUENCE: 58
tttatggtct cagtgcccct caga                                        24

<210> SEQ ID NO 59
<211> LENGTH: 23
<212> TYPE: DNA
<213> ORGANISM: Homo sapiens

<400> SEQUENCE: 59
tcataatcac atatcacatg agc                                         23

<210> SEQ ID NO 60
<211> LENGTH: 21
<212> TYPE: DNA
<213> ORGANISM: Homo sapiens

<400> SEQUENCE: 60
aaacagaacc agggaatga a                                            21

<210> SEQ ID NO 61
<211> LENGTH: 25
<212> TYPE: DNA
```

```
<213> ORGANISM: Homo sapiens

<400> SEQUENCE: 61
tgaaactaaa gtcaaatggg gctac                                    25

<210> SEQ ID NO 62
<211> LENGTH: 24
<212> TYPE: DNA
<213> ORGANISM: Homo sapiens

<400> SEQUENCE: 62 taagggtga cacctctctg gata                                      24

<210> SEQ ID NO 63
<211> LENGTH: 25
<212> TYPE: DNA
<213> ORGANISM: Homo sapiens

<400> SEQUENCE: 63
cccagcctac atctaccact tcatg                                    25

<210> SEQ ID NO 64
<211> LENGTH: 28
<212> TYPE: DNA
<213> ORGANISM: Homo sapiens

<400> SEQUENCE: 64
ctaatgttcg tatggacctt tggaaagc                                 28

<210> SEQ ID NO 65
<211> LENGTH: 24
<212> TYPE: DNA
<213> ORGANISM: Homo sapiens

<400> SEQUENCE: 65
gtctccagta cccagctagc ttag                                     24

<210> SEQ ID NO 66
<211> LENGTH: 22
<212> TYPE: DNA
<213> ORGANISM: Homo sapiens

<400> SEQUENCE: 66
tctcccaacc tgccctttat ca                                       22

<210> SEQ ID NO 67
<211> LENGTH: 20
<212> TYPE: DNA
<213> ORGANISM: Homo sapiens

<400> SEQUENCE: 67
tttgggctga cacagtggct                                          20

<210> SEQ ID NO 68
<211> LENGTH: 24
<212> TYPE: DNA
<213> ORGANISM: Homo sapiens

<400> SEQUENCE: 68
ttgatcaaca caggaggttt gacc                                     24

<210> SEQ ID NO 69
<211> LENGTH: 30
```

<212> TYPE: DNA
<213> ORGANISM: Homo sapiens

<400> SEQUENCE: 69
tataccactt tgatgttgac actagtttac                              30

<210> SEQ ID NO 70
<211> LENGTH: 23
<212> TYPE: DNA
<213> ORGANISM: Homo sapiens

<400> SEQUENCE: 70
cctgtctatg gtctcgattc aat                                    23

<210> SEQ ID NO 71
<211> LENGTH: 21
<212> TYPE: DNA
<213> ORGANISM: Homo sapiens

<400> SEQUENCE: 71
tgcatgacag agggagattc t                                      21

<210> SEQ ID NO 72
<211> LENGTH: 26
<212> TYPE: DNA
<213> ORGANISM: Homo sapiens

<400> SEQUENCE: 72 agagggaaa tagtagaatg aggatg                                  26

<210> SEQ ID NO 73
<211> LENGTH: 24
<212> TYPE: DNA
<213> ORGANISM: Homo sapiens

<400> SEQUENCE: 73
gccaaactct attagtcaac gttc                                   24

<210> SEQ ID NO 74
<211> LENGTH: 24
<212> TYPE: DNA
<213> ORGANISM: Homo sapiens

<400> SEQUENCE: 74
ctggttctct agctcacata cagt                                   24

<210> SEQ ID NO 75
<211> LENGTH: 28
<212> TYPE: DNA
<213> ORGANISM: Homo sapiens

<400> SEQUENCE: 75 tttacccta acaagaaaaa aagaagaa                                28

<210> SEQ ID NO 76
<211> LENGTH: 24
<212> TYPE: DNA
<213> ORGANISM: Homo sapiens

<400> SEQUENCE: 76
cagtgtgaga agtgtgagaa gtgc                                   24

<210> SEQ ID NO 77

```
<211> LENGTH: 21
<212> TYPE: DNA
<213> ORGANISM: Homo sapiens

<400> SEQUENCE: 77
gacaccatgc caaacaacaa c                                             21

<210> SEQ ID NO 78
<211> LENGTH: 26
<212> TYPE: DNA
<213> ORGANISM: Homo sapiens

<400> SEQUENCE: 78
atctatctat tccaattaca tagtcc                                        26

<210> SEQ ID NO 79
<211> LENGTH: 30
<212> TYPE: DNA
<213> ORGANISM: Homo sapiens

<400> SEQUENCE: 79
tcattatacc tacttctgta tccaactctc                                    30

<210> SEQ ID NO 80
<211> LENGTH: 26
<212> TYPE: DNA
<213> ORGANISM: Homo sapiens

<400> SEQUENCE: 80
ggaacacaat tatccctgag tagcag                                        26

<210> SEQ ID NO 81
<211> LENGTH: 29
<212> TYPE: DNA
<213> ORGANISM: Homo sapiens

<400> SEQUENCE: 81
ggtagcataa tagaaatttt atgagtggg                                     29

<210> SEQ ID NO 82
<211> LENGTH: 30
<212> TYPE: DNA
<213> ORGANISM: Homo sapiens

<400> SEQUENCE: 82
gaagacagac ttcaatatca cagaacatcg                                    30

<210> SEQ ID NO 83
<211> LENGTH: 28
<212> TYPE: DNA
<213> ORGANISM: Homo sapiens

<400> SEQUENCE: 83
gtgtatctat tcattcaatc atacaccc                                      28

<210> SEQ ID NO 84
<211> LENGTH: 23
<212> TYPE: DNA
<213> ORGANISM: Homo sapiens

<400> SEQUENCE: 84
ctccctggtt gcaagcaatt gcc                                           23
```

<210> SEQ ID NO 85
<211> LENGTH: 26
<212> TYPE: DNA
<213> ORGANISM: Homo sapiens

<400> SEQUENCE: 85
ccaaaattag tggggaatag ttgaac                                26

<210> SEQ ID NO 86
<211> LENGTH: 24
<212> TYPE: DNA
<213> ORGANISM: Homo sapiens

<400> SEQUENCE: 86
gtcgagatca caccattgca tttc                                  24

<210> SEQ ID NO 87
<211> LENGTH: 24
<212> TYPE: DNA
<213> ORGANISM: Homo sapiens

<400> SEQUENCE: 87
gcctggcttg gaattctttt accc                                  24

<210> SEQ ID NO 88
<211> LENGTH: 35
<212> TYPE: DNA
<213> ORGANISM: Homo sapiens

<400> SEQUENCE: 88
tttaagtctt taatctatct tgaattaata gattc                       35

<210> SEQ ID NO 89
<211> LENGTH: 28
<212> TYPE: DNA
<213> ORGANISM: Homo sapiens

<400> SEQUENCE: 89
ctttaagagg agtctgctaa aaggaatg                              28

<210> SEQ ID NO 90
<211> LENGTH: 20
<212> TYPE: DNA
<213> ORGANISM: Homo sapiens

<400> SEQUENCE: 90
tcaccagaag gttgcaagac                                       20

<210> SEQ ID NO 91
<211> LENGTH: 20
<212> TYPE: DNA
<213> ORGANISM: Homo sapiens

<400> SEQUENCE: 91
tctggcgaag taacccaaac                                       20

<210> SEQ ID NO 92
<211> LENGTH: 21
<212> TYPE: DNA
<213> ORGANISM: Homo sapiens

<400> SEQUENCE: 92
tcgagtcagt tcaccagaag g                                     21

```
<210> SEQ ID NO 93
<211> LENGTH: 17
<212> TYPE: DNA
<213> ORGANISM: Homo sapiens

<400> SEQUENCE: 93
ggaaccagtg agagccg                                                    17

<210> SEQ ID NO 94
<211> LENGTH: 19
<212> TYPE: DNA
<213> ORGANISM: Homo sapiens

<400> SEQUENCE: 94
ctcagagtgc tgaacccag                                                  19

<210> SEQ ID NO 95
<211> LENGTH: 32
<212> TYPE: DNA
<213> ORGANISM: Homo sapiens

<400> SEQUENCE: 95
gtatttattc atgatcagtt cttaactcaa cc                                   32

<210> SEQ ID NO 96
<211> LENGTH: 41
<212> TYPE: DNA
<213> ORGANISM: Homo sapiens

<400> SEQUENCE: 96
ctacctaata tttatctata tcattctaat tatgtctctt c                         41

<210> SEQ ID NO 97
<211> LENGTH: 28
<212> TYPE: DNA
<213> ORGANISM: Homo sapiens

<400> SEQUENCE: 97
ctctaaaggt ttttttggt ggcataag                                         28

<210> SEQ ID NO 98
<211> LENGTH: 32
<212> TYPE: DNA
<213> ORGANISM: Homo sapiens

<400> SEQUENCE: 98
gattaataca acaaaaattt ggtaatctga aa                                   32

<210> SEQ ID NO 99
<211> LENGTH: 26
<212> TYPE: DNA
<213> ORGANISM: Homo sapiens

<400> SEQUENCE: 99
caacctaagc tgaaatgcag atattc                                          26

<210> SEQ ID NO 100
<211> LENGTH: 30
<212> TYPE: DNA
<213> ORGANISM: Homo sapiens

<400> SEQUENCE: 100
gttatgaaac gtaaatgaa tgatgactag                                       30
```

<210> SEQ ID NO 101
<211> LENGTH: 26
<212> TYPE: DNA
<213> ORGANISM: Homo sapiens

<400> SEQUENCE: 101
gcagtctcat ttcctggaga tgaagg                                  26

<210> SEQ ID NO 102
<211> LENGTH: 21
<212> TYPE: DNA
<213> ORGANISM: Homo sapiens

<400> SEQUENCE: 102
cttgggctga ggagttcaat c                                       21

<210> SEQ ID NO 103
<211> LENGTH: 29
<212> TYPE: DNA
<213> ORGANISM: Homo sapiens

<400> SEQUENCE: 103
gccagtaaga ataaaattac agcatgaag                               29

<210> SEQ ID NO 104
<211> LENGTH: 25
<212> TYPE: DNA
<213> ORGANISM: Homo sapiens

<400> SEQUENCE: 104
gaataatcta ccagcaacaa tggct                                   25

<210> SEQ ID NO 105
<211> LENGTH: 20
<212> TYPE: DNA
<213> ORGANISM: Homo sapiens

<400> SEQUENCE: 105
tgcccaatgg aatgctctct                                         20

<210> SEQ ID NO 106
<211> LENGTH: 33
<212> TYPE: DNA
<213> ORGANISM: Homo sapiens

<400> SEQUENCE: 106
gctccatctc aaacaacaaa aacacaaaaa atg                          33

<210> SEQ ID NO 107
<211> LENGTH: 23
<212> TYPE: DNA
<213> ORGANISM: Homo sapiens

<400> SEQUENCE: 107
gggtcattga acctcatgct ctg                                     23

<210> SEQ ID NO 108
<211> LENGTH: 25
<212> TYPE: DNA
<213> ORGANISM: Homo sapiens

<400> SEQUENCE: 108 cccccccaaaa ttctactgaa gtaaa                                              25

<210> SEQ ID NO 109
<211> LENGTH: 28
<212> TYPE: DNA
<213> ORGANISM: Homo sapiens

<400> SEQUENCE: 109
taacaggata aatcacctat ctatgtat                                            28

<210> SEQ ID NO 110
<211> LENGTH: 23
<212> TYPE: DNA
<213> ORGANISM: Homo sapiens

<400> SEQUENCE: 110
gctgaggaga atttccaaat tta                                                 23

<210> SEQ ID NO 111
<211> LENGTH: 28
<212> TYPE: DNA
<213> ORGANISM: Homo sapiens

<400> SEQUENCE: 111
cccgcaaact aactaggata aatctcta                                            28

<210> SEQ ID NO 112
<211> LENGTH: 28
<212> TYPE: DNA
<213> ORGANISM: Homo sapiens

<400> SEQUENCE: 112
cgacatggga aatgtcagat cataagac                                            28

<210> SEQ ID NO 113
<211> LENGTH: 28
<212> TYPE: DNA
<213> ORGANISM: Homo sapiens

<400> SEQUENCE: 113
ccagggagtg aaaaatcctt ttatcatc                                            28

<210> SEQ ID NO 114
<211> LENGTH: 25
<212> TYPE: DNA
<213> ORGANISM: Homo sapiens

<400> SEQUENCE: 114
gaggatgaag gttagagcca gacct                                               25

<210> SEQ ID NO 115
<211> LENGTH: 28
<212> TYPE: DNA
<213> ORGANISM: Homo sapiens

<400> SEQUENCE: 115
tgtggaataa actgaaggct aaagaaaa                                            28

<210> SEQ ID NO 116
<211> LENGTH: 28
<212> TYPE: DNA
<213> ORGANISM: Homo sapiens

<400> SEQUENCE: 116

| | |
|---|---|
| caagccctat gccaaggata taacaatg | 28 |

<210> SEQ ID NO 117
<211> LENGTH: 28
<212> TYPE: DNA
<213> ORGANISM: Homo sapiens

<400> SEQUENCE: 117

| | |
|---|---|
| gaggttttac tgtattagga gttcccac | 28 |

<210> SEQ ID NO 118
<211> LENGTH: 28
<212> TYPE: DNA
<213> ORGANISM: Homo sapiens

<400> SEQUENCE: 118

| | |
|---|---|
| cagatgtgag atgataattt cgttctcc | 28 |

<210> SEQ ID NO 119
<211> LENGTH: 26
<212> TYPE: DNA
<213> ORGANISM: Homo sapiens

<400> SEQUENCE: 119

| | |
|---|---|
| ttgttcttct ccatcccatt tcaccc | 26 |

<210> SEQ ID NO 120
<211> LENGTH: 28
<212> TYPE: DNA
<213> ORGANISM: Homo sapiens

<400> SEQUENCE: 120

| | |
|---|---|
| cttgtacatt cccttatctg ctatgtgg | 28 |

<210> SEQ ID NO 121
<211> LENGTH: 28
<212> TYPE: DNA
<213> ORGANISM: Homo sapiens

<400> SEQUENCE: 121

| | |
|---|---|
| ctctctttgg agttttatgt gttgctac | 28 |

<210> SEQ ID NO 122
<211> LENGTH: 28
<212> TYPE: DNA
<213> ORGANISM: Homo sapiens

<400> SEQUENCE: 122

| | |
|---|---|
| ctctgatgat gtgcaagaaa ggtaggta | 28 |

<210> SEQ ID NO 123
<211> LENGTH: 29
<212> TYPE: DNA
<213> ORGANISM: Homo sapiens

<400> SEQUENCE: 123

| | |
|---|---|
| tcagactatg ttttaaggag actatgagg | 29 |

<210> SEQ ID NO 124
<211> LENGTH: 28
<212> TYPE: DNA
<213> ORGANISM: Homo sapiens

<400> SEQUENCE: 124
ctaagtatct accaatgtgc tacgtacc                                              28

<210> SEQ ID NO 125
<211> LENGTH: 26
<212> TYPE: DNA
<213> ORGANISM: Homo sapiens

<400> SEQUENCE: 125
cacgtggatg atatggtttc tcaagg                                                26

<210> SEQ ID NO 126
<211> LENGTH: 28
<212> TYPE: DNA
<213> ORGANISM: Homo sapiens

<400> SEQUENCE: 126
agcacctata tattatacct gaaagcat                                              28

<210> SEQ ID NO 127
<211> LENGTH: 28
<212> TYPE: DNA
<213> ORGANISM: Homo sapiens

<400> SEQUENCE: 127
cccatgattt tcttgtggtg agaatttc                                              28

<210> SEQ ID NO 128
<211> LENGTH: 28
<212> TYPE: DNA
<213> ORGANISM: Homo sapiens

<400> SEQUENCE: 128
caccctctgt actttaattt gacttccc                                              28

<210> SEQ ID NO 129
<211> LENGTH: 27
<212> TYPE: DNA
<213> ORGANISM: Homo sapiens

<400> SEQUENCE: 129
gtttttcttc attcccatgt tgtgtac                                               27

<210> SEQ ID NO 130
<211> LENGTH: 26
<212> TYPE: DNA
<213> ORGANISM: Homo sapiens

<400> SEQUENCE: 130
cactcttctg aatcctggtc aacaac                                                26

<210> SEQ ID NO 131
<211> LENGTH: 28
<212> TYPE: DNA
<213> ORGANISM: Homo sapiens

<400> SEQUENCE: 131
caagttatat catagagtct acgacccc                                              28

<210> SEQ ID NO 132
<211> LENGTH: 28
<212> TYPE: DNA

```
<400> SEQUENCE: 132
ctgcaactat cagtctctgc ccttattc                                          28

<210> SEQ ID NO 133
<211> LENGTH: 28
<212> TYPE: DNA
<213> ORGANISM: Homo sapiens

<400> SEQUENCE: 133
gatgtgtctc aaactgttta ttgtgagg                                          28

<210> SEQ ID NO 134
<211> LENGTH: 28
<212> TYPE: DNA
<213> ORGANISM: Homo sapiens

<400> SEQUENCE: 134
gaactcattt atccagagac ctgttctc                                          28

<210> SEQ ID NO 135
<211> LENGTH: 28
<212> TYPE: DNA
<213> ORGANISM: Homo sapiens

<400> SEQUENCE: 135
cataatacaa cctgtctttg gagttact                                          28

<210> SEQ ID NO 136
<211> LENGTH: 28
<212> TYPE: DNA
<213> ORGANISM: Homo sapiens

<400> SEQUENCE: 136
gtgaccagta gttctatgag caagtatg                                          28

<210> SEQ ID NO 137
<211> LENGTH: 28
<212> TYPE: DNA
<213> ORGANISM: Homo sapiens

<400> SEQUENCE: 137
ccacattgta tggtttttag gcaccatg                                          28

<210> SEQ ID NO 138
<211> LENGTH: 28
<212> TYPE: DNA
<213> ORGANISM: Homo sapiens

<400> SEQUENCE: 138
ctaataagtg ggacagttaa gagaaggc                                          28

<210> SEQ ID NO 139
<211> LENGTH: 27
<212> TYPE: DNA
<213> ORGANISM: Homo sapiens

<400> SEQUENCE: 139
caagacaagc gattgaaaga agtggat                                           27

<210> SEQ ID NO 140
<211> LENGTH: 28
<212> TYPE: DNA
```

<213> ORGANISM: Homo sapiens

<400> SEQUENCE: 140
ccttgtcaat ctttctacca gagggtaa                                               28

<210> SEQ ID NO 141
<211> LENGTH: 25
<212> TYPE: DNA
<213> ORGANISM: Homo sapiens

<400> SEQUENCE: 141
gaatcatagc ttgtgttggt caggg                                                  25

<210> SEQ ID NO 142
<211> LENGTH: 27
<212> TYPE: DNA
<213> ORGANISM: Homo sapiens

<400> SEQUENCE: 142
gaattacaag tatttgcatc ccagcct                                                27

<210> SEQ ID NO 143
<211> LENGTH: 28
<212> TYPE: DNA
<213> ORGANISM: Homo sapiens

<400> SEQUENCE: 143
gaccaacttg gctttaacag atgcaaat                                               28

<210> SEQ ID NO 144
<211> LENGTH: 28
<212> TYPE: DNA
<213> ORGANISM: Homo sapiens

<400> SEQUENCE: 144
tccttacctt taagactttt cctatttg                                               28

<210> SEQ ID NO 145
<211> LENGTH: 28
<212> TYPE: DNA
<213> ORGANISM: Homo sapiens

<400> SEQUENCE: 145
cattatctcg tcatacttcc ctgtcttg                                               28

<210> SEQ ID NO 146
<211> LENGTH: 28
<212> TYPE: DNA
<213> ORGANISM: Homo sapiens

<400> SEQUENCE: 146
gcatcaaatt caccagtgaa attattga                                               28

<210> SEQ ID NO 147
<211> LENGTH: 28
<212> TYPE: DNA
<213> ORGANISM: Homo sapiens

<400> SEQUENCE: 147
atgagtacat tattcaactg ttttggag                                               28

<210> SEQ ID NO 148
<211> LENGTH: 28

```
<212> TYPE: DNA
<213> ORGANISM: Homo sapiens

<400> SEQUENCE: 148
cagccatgtt gtaaacattt ttacggtc                                          28

<210> SEQ ID NO 149
<211> LENGTH: 28
<212> TYPE: DNA
<213> ORGANISM: Homo sapiens

<400> SEQUENCE: 149
gcacattcta agaactggtg attctatc                                          28

<210> SEQ ID NO 150
<211> LENGTH: 28
<212> TYPE: DNA
<213> ORGANISM: Homo sapiens

<400> SEQUENCE: 150
gctagaaaaa gctgagatag ctgtgaag                                          28

<210> SEQ ID NO 151
<211> LENGTH: 26
<212> TYPE: DNA
<213> ORGANISM: Homo sapiens

<400> SEQUENCE: 151
ccttgaagct cattctttgt tgtccc                                            26

<210> SEQ ID NO 152
<211> LENGTH: 28
<212> TYPE: DNA
<213> ORGANISM: Homo sapiens

<400> SEQUENCE: 152
ctggacacca gaccaaaaac aaataacc                                          28

<210> SEQ ID NO 153
<211> LENGTH: 27
<212> TYPE: DNA
<213> ORGANISM: Homo sapiens

<400> SEQUENCE: 153
gtaattagag ggcagtgagg cttttaa                                           27

<210> SEQ ID NO 154
<211> LENGTH: 28
<212> TYPE: DNA
<213> ORGANISM: Homo sapiens

<400> SEQUENCE: 154
ctccagaagc tactgggata ttaattag                                          28

<210> SEQ ID NO 155
<211> LENGTH: 28
<212> TYPE: DNA
<213> ORGANISM: Homo sapiens

<400> SEQUENCE: 155
tgagccaaat cagcaatata ataggact                                          28

<210> SEQ ID NO 156
```

```
<211> LENGTH: 28
<212> TYPE: DNA
<213> ORGANISM: Homo sapiens

<400> SEQUENCE: 156
cctagaacca caattatctg tctttggc                                              28

<210> SEQ ID NO 157
<211> LENGTH: 28
<212> TYPE: DNA
<213> ORGANISM: Homo sapiens

<400> SEQUENCE: 157
ccattgattc tctacagttc tgcaggta                                              28

<210> SEQ ID NO 158
<211> LENGTH: 28
<212> TYPE: DNA
<213> ORGANISM: Homo sapiens

<400> SEQUENCE: 158
ctccacactt tatacaggtg aaatctga                                              28

<210> SEQ ID NO 159
<211> LENGTH: 28
<212> TYPE: DNA
<213> ORGANISM: Homo sapiens

<400> SEQUENCE: 159
catttttctc tccttctgtc tcaccttc                                              28

<210> SEQ ID NO 160
<211> LENGTH: 28
<212> TYPE: DNA
<213> ORGANISM: Homo sapiens

<400> SEQUENCE: 160
gcttctcttt cccttatgta tctctctc                                              28

<210> SEQ ID NO 161
<211> LENGTH: 28
<212> TYPE: DNA
<213> ORGANISM: Homo sapiens

<400> SEQUENCE: 161
ggcttttgaa gaaaaacact aacctgtc                                              28

<210> SEQ ID NO 162
<211> LENGTH: 26
<212> TYPE: DNA
<213> ORGANISM: Homo sapiens

<400> SEQUENCE: 162
cacctatggg ctcttcttat ttctcc                                                26

<210> SEQ ID NO 163
<211> LENGTH: 28
<212> TYPE: DNA
<213> ORGANISM: Homo sapiens

<400> SEQUENCE: 163
catttgatag ccatttgggt tgtttcca                                              28
```

<210> SEQ ID NO 164
<211> LENGTH: 28
<212> TYPE: DNA
<213> ORGANISM: Homo sapiens

<400> SEQUENCE: 164
ccatcacact atcctgacat gaacaaat                                    28

<210> SEQ ID NO 165
<211> LENGTH: 26
<212> TYPE: DNA
<213> ORGANISM: Homo sapiens

<400> SEQUENCE: 165
gaagatttgc atcccagtga aagcac                                      26

<210> SEQ ID NO 166
<211> LENGTH: 28
<212> TYPE: DNA
<213> ORGANISM: Homo sapiens

<400> SEQUENCE: 166
gcacttcata aagaatcagt caggatgc                                    28

<210> SEQ ID NO 167
<211> LENGTH: 28
<212> TYPE: DNA
<213> ORGANISM: Homo sapiens

<400> SEQUENCE: 167
ggagaatcag gaaatagtca cttcctac                                    28

<210> SEQ ID NO 168
<211> LENGTH: 28
<212> TYPE: DNA
<213> ORGANISM: Homo sapiens

<400> SEQUENCE: 168
catttgacct tctagccaaa tgaagtac                                    28

<210> SEQ ID NO 169
<211> LENGTH: 28
<212> TYPE: DNA
<213> ORGANISM: Homo sapiens

<400> SEQUENCE: 169
ggaatttctg agaataacat tgcctctc                                    28

<210> SEQ ID NO 170
<211> LENGTH: 28
<212> TYPE: DNA
<213> ORGANISM: Homo sapiens

<400> SEQUENCE: 170
catatgttgg gggagctaaa cctaatga                                    28

<210> SEQ ID NO 171
<211> LENGTH: 27
<212> TYPE: DNA
<213> ORGANISM: Homo sapiens

<400> SEQUENCE: 171
cactgtgacc acagcatctt ttaactc                                     27

```
<210> SEQ ID NO 172
<211> LENGTH: 28
<212> TYPE: DNA
<213> ORGANISM: Homo sapiens

<400> SEQUENCE: 172
gggtaaagaa atattcagca catccaaa                                              28

<210> SEQ ID NO 173
<211> LENGTH: 28
<212> TYPE: DNA
<213> ORGANISM: Homo sapiens

<400> SEQUENCE: 173
gagtatccct tatctaaaat gctggtcc                                              28

<210> SEQ ID NO 174
<211> LENGTH: 28
<212> TYPE: DNA
<213> ORGANISM: Homo sapiens

<400> SEQUENCE: 174 cttttctct taccggaact tcaacgac                                               28

<210> SEQ ID NO 175
<211> LENGTH: 28
<212> TYPE: DNA
<213> ORGANISM: Homo sapiens

<400> SEQUENCE: 175
cctcattaat atgaccaagg ctcctctg                                              28

<210> SEQ ID NO 176
<211> LENGTH: 28
<212> TYPE: DNA
<213> ORGANISM: Homo sapiens

<400> SEQUENCE: 176
tgactctaat tggggatgtg gtaattag                                              28

<210> SEQ ID NO 177
<211> LENGTH: 25
<212> TYPE: DNA
<213> ORGANISM: Homo sapiens

<400> SEQUENCE: 177
gacctaacct ggagaaaacc ggaga                                                 25

<210> SEQ ID NO 178
<211> LENGTH: 28
<212> TYPE: DNA
<213> ORGANISM: Homo sapiens

<400> SEQUENCE: 178
gtttctcttc tctgaacctt tgtctcag                                              28

<210> SEQ ID NO 179
<211> LENGTH: 28
<212> TYPE: DNA
<213> ORGANISM: Homo sapiens

<400> SEQUENCE: 179
gcaaacacac aaagataggt tcgagttt                                              28
```

```
<210> SEQ ID NO 180
<211> LENGTH: 28
<212> TYPE: DNA
<213> ORGANISM: Homo sapiens

<400> SEQUENCE: 180
catatcaagt gctttctgtt gacatttg                                          28

<210> SEQ ID NO 181
<211> LENGTH: 28
<212> TYPE: DNA
<213> ORGANISM: Homo sapiens

<400> SEQUENCE: 181
ctgaaaagtg ctacgtaaga ggtcattg                                          28

<210> SEQ ID NO 182
<211> LENGTH: 25
<212> TYPE: DNA
<213> ORGANISM: Homo sapiens

<400> SEQUENCE: 182
catctgagtg tgagaagagc ctcaa                                             25

<210> SEQ ID NO 183
<211> LENGTH: 28
<212> TYPE: DNA
<213> ORGANISM: Homo sapiens

<400> SEQUENCE: 183
cccagcaaaa acttcttttc tccagtaa                                          28

<210> SEQ ID NO 184
<211> LENGTH: 28
<212> TYPE: DNA
<213> ORGANISM: Homo sapiens

<400> SEQUENCE: 184
gctaggaaag ttttctctct ggttcaca                                          28

<210> SEQ ID NO 185
<211> LENGTH: 27
<212> TYPE: DNA
<213> ORGANISM: Homo sapiens

<400> SEQUENCE: 185
gaatatctat gagcaggcag ttagcag                                           27

<210> SEQ ID NO 186
<211> LENGTH: 28
<212> TYPE: DNA
<213> ORGANISM: Homo sapiens

<400> SEQUENCE: 186
ctaatcagtg tcactatgtg tgagctat                                          28

<210> SEQ ID NO 187
<211> LENGTH: 28
<212> TYPE: DNA
<213> ORGANISM: Homo sapiens

<400> SEQUENCE: 187
```
catcatacag actcaaggag cttagctg                                          28

<210> SEQ ID NO 188
<211> LENGTH: 28
<212> TYPE: DNA
<213> ORGANISM: Homo sapiens

<400> SEQUENCE: 188
ctttccaagc cttggaaaac acagaaaa                                          28

<210> SEQ ID NO 189
<211> LENGTH: 27
<212> TYPE: DNA
<213> ORGANISM: Homo sapiens

<400> SEQUENCE: 189
gtaccttata aatcacggag tgcagac                                           27

<210> SEQ ID NO 190
<211> LENGTH: 27
<212> TYPE: DNA
<213> ORGANISM: Homo sapiens

<400> SEQUENCE: 190
caagtggtaa gagatgactg aggtcaa                                           27

<210> SEQ ID NO 191
<211> LENGTH: 28
<212> TYPE: DNA
<213> ORGANISM: Homo sapiens

<400> SEQUENCE: 191
cttcttctct tagaaggaca ctggtcag                                          28

<210> SEQ ID NO 192
<211> LENGTH: 27
<212> TYPE: DNA
<213> ORGANISM: Homo sapiens

<400> SEQUENCE: 192
gttatggagg attggtaaga accagag                                           27

<210> SEQ ID NO 193
<211> LENGTH: 28
<212> TYPE: DNA
<213> ORGANISM: Homo sapiens

<400> SEQUENCE: 193
gagctgttta agggtaaagg ggtagtta                                          28

<210> SEQ ID NO 194
<211> LENGTH: 28
<212> TYPE: DNA
<213> ORGANISM: Homo sapiens

<400> SEQUENCE: 194
gcagacaaaa ccatgacaat gatcttag                                          28

<210> SEQ ID NO 195
<211> LENGTH: 28
<212> TYPE: DNA
<213> ORGANISM: Homo sapiens

<400> SEQUENCE: 195
cccatgatga aacagtttgc actaaatg                                           28

<210> SEQ ID NO 196
<211> LENGTH: 27
<212> TYPE: DNA
<213> ORGANISM: Homo sapiens

<400> SEQUENCE: 196
ctcaattttc ttgtccctgc tttcatg                                            27

<210> SEQ ID NO 197
<211> LENGTH: 28
<212> TYPE: DNA
<213> ORGANISM: Homo sapiens

<400> SEQUENCE: 197
ttagaaattc cagatagagc taaaactg                                           28

<210> SEQ ID NO 198
<211> LENGTH: 25
<212> TYPE: DNA
<213> ORGANISM: Homo sapiens

<400> SEQUENCE: 198
gttaggaaaa gaacccaggt gtttt                                              25

<210> SEQ ID NO 199
<211> LENGTH: 27
<212> TYPE: DNA
<213> ORGANISM: Homo sapiens

<400> SEQUENCE: 199
gcaaaagtaa atacaaaggc atacttt                                            27

<210> SEQ ID NO 200
<211> LENGTH: 28
<212> TYPE: DNA
<213> ORGANISM: Homo sapiens

<400> SEQUENCE: 200
caatgcaaaa gaaaggtcct tactcgac                                           28

<210> SEQ ID NO 201
<211> LENGTH: 28
<212> TYPE: DNA
<213> ORGANISM: Homo sapiens

<400> SEQUENCE: 201
catttctaaa ctctaaaaca aacatttg                                           28

<210> SEQ ID NO 202
<211> LENGTH: 28
<212> TYPE: DNA
<213> ORGANISM: Homo sapiens

<400> SEQUENCE: 202
ggtccttaac ctattaaatt ttaatgag                                           28

<210> SEQ ID NO 203
<211> LENGTH: 28
<212> TYPE: DNA
<213> ORGANISM: Homo sapiens

```
<400> SEQUENCE: 203
gactttcaat ttatgtcagc atttaaaa                                              28

<210> SEQ ID NO 204
<211> LENGTH: 27
<212> TYPE: DNA
<213> ORGANISM: Homo sapiens

<400> SEQUENCE: 204
cctcttggtt gcattggatt ctcattg                                               27

<210> SEQ ID NO 205
<211> LENGTH: 27
<212> TYPE: DNA
<213> ORGANISM: Homo sapiens

<400> SEQUENCE: 205
tctccatgaa acttgggtta attttgc                                               27

<210> SEQ ID NO 206
<211> LENGTH: 25
<212> TYPE: DNA
<213> ORGANISM: Homo sapiens

<400> SEQUENCE: 206
tgtctggaag ttcgtcaaat tgcag                                                 25

<210> SEQ ID NO 207
<211> LENGTH: 28
<212> TYPE: DNA
<213> ORGANISM: Homo sapiens

<400> SEQUENCE: 207
gtagcataaa acattccaaa aattcaat                                              28

<210> SEQ ID NO 208
<211> LENGTH: 30
<212> TYPE: DNA
<213> ORGANISM: Homo sapiens

<400> SEQUENCE: 208
tgctttaaag atacaggtta tctgtattac                                            30

<210> SEQ ID NO 209
<211> LENGTH: 26
<212> TYPE: DNA
<213> ORGANISM: Homo sapiens

<400> SEQUENCE: 209
ctctccgtta ctttcttcct gccttt                                                26

<210> SEQ ID NO 210
<211> LENGTH: 26
<212> TYPE: DNA
<213> ORGANISM: Homo sapiens

<400> SEQUENCE: 210
gatcctgaga ttcacctcta gtccct                                                26

<210> SEQ ID NO 211
<211> LENGTH: 26
<212> TYPE: DNA
<213> ORGANISM: Homo sapiens
```

```
<400> SEQUENCE: 211
ccgtaccagg tacctagcta tgtact                                          26

<210> SEQ ID NO 212
<211> LENGTH: 27
<212> TYPE: DNA
<213> ORGANISM: Homo sapiens

<400> SEQUENCE: 212
ctttctgttt tgtccatctg aaattct                                         27

<210> SEQ ID NO 213
<211> LENGTH: 27
<212> TYPE: DNA
<213> ORGANISM: Homo sapiens

<400> SEQUENCE: 213
caaagttaag tatcaccatc cagctgg                                         27

<210> SEQ ID NO 214
<211> LENGTH: 28
<212> TYPE: DNA
<213> ORGANISM: Homo sapiens

<400> SEQUENCE: 214
atagggatag ctgataagaa acatgacc                                        28

<210> SEQ ID NO 215
<211> LENGTH: 25
<212> TYPE: DNA
<213> ORGANISM: Homo sapiens

<400> SEQUENCE: 215
cttaataaga cgctgcatct gccca                                           25

<210> SEQ ID NO 216
<211> LENGTH: 28
<212> TYPE: DNA
<213> ORGANISM: Homo sapiens

<400> SEQUENCE: 216
tccaggagac atttgttcat ataagtga                                        28

<210> SEQ ID NO 217
<211> LENGTH: 28
<212> TYPE: DNA
<213> ORGANISM: Homo sapiens

<400> SEQUENCE: 217
agacactttt cagtatccat ttagaaac                                        28

<210> SEQ ID NO 218
<211> LENGTH: 25
<212> TYPE: DNA
<213> ORGANISM: Homo sapiens

<400> SEQUENCE: 218
gtttcacatg tgcatgcttt tgggt                                           25

<210> SEQ ID NO 219
<211> LENGTH: 26
<212> TYPE: DNA
```

<213> ORGANISM: Homo sapiens

<400> SEQUENCE: 219
ccaaagctat tctctctttt gggtgc                                    26

<210> SEQ ID NO 220
<211> LENGTH: 27
<212> TYPE: DNA
<213> ORGANISM: Homo sapiens

<400> SEQUENCE: 220
gaaagttcac ttcagatgtt caaagcc                                   27

<210> SEQ ID NO 221
<211> LENGTH: 26
<212> TYPE: DNA
<213> ORGANISM: Homo sapiens

<400> SEQUENCE: 221
gggtttcagt ctgcaacaag atcttg                                    26

<210> SEQ ID NO 222
<211> LENGTH: 28
<212> TYPE: DNA
<213> ORGANISM: Homo sapiens

<400> SEQUENCE: 222
tggagatcaa tatttagcct taacatat                                  28

<210> SEQ ID NO 223
<211> LENGTH: 28
<212> TYPE: DNA
<213> ORGANISM: Homo sapiens

<400> SEQUENCE: 223
gactgtttct catcctgtta ttatttgt                                  28

<210> SEQ ID NO 224
<211> LENGTH: 25
<212> TYPE: DNA
<213> ORGANISM: Homo sapiens

<400> SEQUENCE: 224
aacacacaga aacatcaagc tgagc                                     25

<210> SEQ ID NO 225
<211> LENGTH: 27
<212> TYPE: DNA
<213> ORGANISM: Homo sapiens

<400> SEQUENCE: 225
ttcctgacat tctccttctt ctatctg                                   27

<210> SEQ ID NO 226
<211> LENGTH: 26
<212> TYPE: DNA
<213> ORGANISM: Homo sapiens

<400> SEQUENCE: 226
tatgacgcct ggattttcac aacaac                                    26

<210> SEQ ID NO 227
<211> LENGTH: 28

```
<212> TYPE: DNA
<213> ORGANISM: Homo sapiens

<400> SEQUENCE: 227
cagagactat ggatggtatt taggtcaa                                        28

<210> SEQ ID NO 228
<211> LENGTH: 25
<212> TYPE: DNA
<213> ORGANISM: Homo sapiens

<400> SEQUENCE: 228
actttgtgtg gctgagagag agaaa                                           25

<210> SEQ ID NO 229
<211> LENGTH: 30
<212> TYPE: DNA
<213> ORGANISM: Homo sapiens

<400> SEQUENCE: 229
tgagtgttct ctgtattttc ttactctaag                                      30

<210> SEQ ID NO 230
<211> LENGTH: 27
<212> TYPE: DNA
<213> ORGANISM: Homo sapiens

<400> SEQUENCE: 230
atttttggtc attgttgaca cttcacc                                         27

<210> SEQ ID NO 231
<211> LENGTH: 25
<212> TYPE: DNA
<213> ORGANISM: Homo sapiens

<400> SEQUENCE: 231
ggtgttaggg agacaggcat gaatg                                           25

<210> SEQ ID NO 232
<211> LENGTH: 26
<212> TYPE: DNA
<213> ORGANISM: Homo sapiens

<400> SEQUENCE: 232
tgaaactttt caactctcct accgcc                                          26

<210> SEQ ID NO 233
<211> LENGTH: 28
<212> TYPE: DNA
<213> ORGANISM: Homo sapiens

<400> SEQUENCE: 233
gttaaaattg ccactaatta tgtgtttt                                        28

<210> SEQ ID NO 234
<211> LENGTH: 27
<212> TYPE: DNA
<213> ORGANISM: Homo sapiens

<400> SEQUENCE: 234
aactgatcct atgcagcaag atctttg                                         27

<210> SEQ ID NO 235
```

```
<211> LENGTH: 27
<212> TYPE: DNA
<213> ORGANISM: Homo sapiens

<400> SEQUENCE: 235
gatgcttgca aacaaagact gaaaagg                                           27

<210> SEQ ID NO 236
<211> LENGTH: 28
<212> TYPE: DNA
<213> ORGANISM: Homo sapiens

<400> SEQUENCE: 236
gtctgtgtgt cctctgagat gatgaatg                                          28

<210> SEQ ID NO 237
<211> LENGTH: 26
<212> TYPE: DNA
<213> ORGANISM: Homo sapiens

<400> SEQUENCE: 237
gggaggaaga aaacagagag tcttga                                            26

<210> SEQ ID NO 238
<211> LENGTH: 28
<212> TYPE: DNA
<213> ORGANISM: Homo sapiens

<400> SEQUENCE: 238
agtttgttgg cttcttttga gaagtatc                                          28

<210> SEQ ID NO 239
<211> LENGTH: 28
<212> TYPE: DNA
<213> ORGANISM: Homo sapiens

<400> SEQUENCE: 239
ggcagatgaa gtagtagata tctggctg                                          28

<210> SEQ ID NO 240
<211> LENGTH: 27
<212> TYPE: DNA
<213> ORGANISM: Homo sapiens

<400> SEQUENCE: 240
gttcagtgtc aattttgacc agatatt                                           27

<210> SEQ ID NO 241
<211> LENGTH: 28
<212> TYPE: DNA
<213> ORGANISM: Homo sapiens

<400> SEQUENCE: 241
agacatagga cacaccattt tattgtct                                          28

<210> SEQ ID NO 242
<211> LENGTH: 28
<212> TYPE: DNA
<213> ORGANISM: Homo sapiens

<400> SEQUENCE: 242
tcaaaatatt tggctaaact attgccgg                                          28
```

```
<210> SEQ ID NO 243
<211> LENGTH: 31
<212> TYPE: DNA
<213> ORGANISM: Homo sapiens

<400> SEQUENCE: 243
ctggagttat taataaattg gattatatag c                             31

<210> SEQ ID NO 244
<211> LENGTH: 27
<212> TYPE: DNA
<213> ORGANISM: Homo sapiens

<400> SEQUENCE: 244
ttacctgttt tccttttgtg attccac                                  27

<210> SEQ ID NO 245
<211> LENGTH: 26
<212> TYPE: DNA
<213> ORGANISM: Homo sapiens

<400> SEQUENCE: 245
accaagtcaa gagctctgag agacat                                   26

<210> SEQ ID NO 246
<211> LENGTH: 28
<212> TYPE: DNA
<213> ORGANISM: Homo sapiens

<400> SEQUENCE: 246
acagtgaatg atattcagaa tattgtgc                                 28

<210> SEQ ID NO 247
<211> LENGTH: 28
<212> TYPE: DNA
<213> ORGANISM: Homo sapiens

<400> SEQUENCE: 247
gaacaaggtc aagatatcag ctttcacc                                 28

<210> SEQ ID NO 248
<211> LENGTH: 26
<212> TYPE: DNA
<213> ORGANISM: Homo sapiens

<400> SEQUENCE: 248
aggtcataca atgaatggtg tgatgt                                   26

<210> SEQ ID NO 249
<211> LENGTH: 27
<212> TYPE: DNA
<213> ORGANISM: Homo sapiens

<400> SEQUENCE: 249
atccacccat gagaaatata tccacaa                                  27

<210> SEQ ID NO 250
<211> LENGTH: 31
<212> TYPE: DNA
<213> ORGANISM: Homo sapiens

<400> SEQUENCE: 250
acaattcaaa ttaatgtaaa aactgcaagt g                             31
```

<210> SEQ ID NO 251
<211> LENGTH: 25
<212> TYPE: DNA
<213> ORGANISM: Homo sapiens

<400> SEQUENCE: 251
tagttctagt gtgggatctg actcc                                25

<210> SEQ ID NO 252
<211> LENGTH: 27
<212> TYPE: DNA
<213> ORGANISM: Homo sapiens

<400> SEQUENCE: 252
gaacatctgt tcaggtttct ctccatc                              27

<210> SEQ ID NO 253
<211> LENGTH: 27
<212> TYPE: DNA
<213> ORGANISM: Homo sapiens

<400> SEQUENCE: 253
gaaaggacta aattgttgaa cactggt                              27

<210> SEQ ID NO 254
<211> LENGTH: 25
<212> TYPE: DNA
<213> ORGANISM: Homo sapiens

<400> SEQUENCE: 254
tgtgtgtttt aaagccaggt ttgtt                                25

<210> SEQ ID NO 255
<211> LENGTH: 25
<212> TYPE: DNA
<213> ORGANISM: Homo sapiens

<400> SEQUENCE: 255
gatggactgg aactgaggat tttca                                25

<210> SEQ ID NO 256
<211> LENGTH: 29
<212> TYPE: DNA
<213> ORGANISM: Homo sapiens

<400> SEQUENCE: 256
agctttagaa aggcatatcg tattaactg                            29

<210> SEQ ID NO 257
<211> LENGTH: 25
<212> TYPE: DNA
<213> ORGANISM: Homo sapiens

<400> SEQUENCE: 257
ttatagtgag taaaggacag gcccc                                25

<210> SEQ ID NO 258
<211> LENGTH: 29
<212> TYPE: DNA
<213> ORGANISM: Homo sapiens

<400> SEQUENCE: 258
acacatctgt tgacagtaat gaaatatcc                            29

<210> SEQ ID NO 259
<211> LENGTH: 28
<212> TYPE: DNA
<213> ORGANISM: Homo sapiens

<400> SEQUENCE: 259
gtttaaactt ggataccatc cccaagac                                    28

<210> SEQ ID NO 260
<211> LENGTH: 25
<212> TYPE: DNA
<213> ORGANISM: Homo sapiens

<400> SEQUENCE: 260
atgagattgc tgggagatgc agatg                                       25

<210> SEQ ID NO 261
<211> LENGTH: 26
<212> TYPE: DNA
<213> ORGANISM: Homo sapiens

<400> SEQUENCE: 261
cacatttccc tcttgcggtt acatac                                      26

<210> SEQ ID NO 262
<211> LENGTH: 25
<212> TYPE: DNA
<213> ORGANISM: Homo sapiens

<400> SEQUENCE: 262
gacaagcctc gcttgagttt tcttt                                       25

<210> SEQ ID NO 263
<211> LENGTH: 25
<212> TYPE: DNA
<213> ORGANISM: Homo sapiens

<400> SEQUENCE: 263
tgtgagagtg tcaccgaatt caacg                                       25

<210> SEQ ID NO 264
<211> LENGTH: 27
<212> TYPE: DNA
<213> ORGANISM: Homo sapiens

<400> SEQUENCE: 264
aaatagcaat ggctcgtcta tggttag                                     27

<210> SEQ ID NO 265
<211> LENGTH: 27
<212> TYPE: DNA
<213> ORGANISM: Homo sapiens

<400> SEQUENCE: 265
tgctaagtaa ggtgagtggt ataatca                                     27

<210> SEQ ID NO 266
<211> LENGTH: 27
<212> TYPE: DNA
<213> ORGANISM: Homo sapiens

<400> SEQUENCE: 266

```
ataaatatga tgtggctact ccctcat                                           27

<210> SEQ ID NO 267
<211> LENGTH: 29
<212> TYPE: DNA
<213> ORGANISM: Homo sapiens

<400> SEQUENCE: 267
gctacacctc catagtaata atgtaagag                                         29

<210> SEQ ID NO 268
<211> LENGTH: 26
<212> TYPE: DNA
<213> ORGANISM: Homo sapiens

<400> SEQUENCE: 268
tgaagcagct agagaactct gtacgt                                            26

<210> SEQ ID NO 269
<211> LENGTH: 31
<212> TYPE: DNA
<213> ORGANISM: Homo sapiens

<400> SEQUENCE: 269
ttttgtctct gttatattag tcacctatct c                                      31

<210> SEQ ID NO 270
<211> LENGTH: 26
<212> TYPE: DNA
<213> ORGANISM: Homo sapiens

<400> SEQUENCE: 270
atagccctgc attcaaatcc caagtg                                            26

<210> SEQ ID NO 271
<211> LENGTH: 26
<212> TYPE: DNA
<213> ORGANISM: Homo sapiens

<400> SEQUENCE: 271
tccattttta taccactgca ctgaag                                            26

<210> SEQ ID NO 272
<211> LENGTH: 28
<212> TYPE: DNA
<213> ORGANISM: Homo sapiens

<400> SEQUENCE: 272
gcagtaaaac attttcatca aatttcca                                          28

<210> SEQ ID NO 273
<211> LENGTH: 27
<212> TYPE: DNA
<213> ORGANISM: Homo sapiens

<400> SEQUENCE: 273
tctgggtgca aactagctga atatcag                                           27

<210> SEQ ID NO 274
<211> LENGTH: 27
<212> TYPE: DNA
<213> ORGANISM: Homo sapiens

<400> SEQUENCE: 274
```

-continued gaaaatctgg aggcaattca tgatgcc                                27

<210> SEQ ID NO 275
<211> LENGTH: 26
<212> TYPE: DNA
<213> ORGANISM: Homo sapiens

<400> SEQUENCE: 275
atacaatgat gatcacacgg gaccct                                 26

<210> SEQ ID NO 276
<211> LENGTH: 27
<212> TYPE: DNA
<213> ORGANISM: Homo sapiens

<400> SEQUENCE: 276
ccatgaagat ggagtcaaca ttttaca                                27

<210> SEQ ID NO 277
<211> LENGTH: 26
<212> TYPE: DNA
<213> ORGANISM: Homo sapiens

<400> SEQUENCE: 277
tcctaacccc tagtacgtta gatgtg                                 26

<210> SEQ ID NO 278
<211> LENGTH: 25
<212> TYPE: DNA
<213> ORGANISM: Homo sapiens

<400> SEQUENCE: 278
gaggtgattt ctgtgaggaa cgtcg                                  25

<210> SEQ ID NO 279
<211> LENGTH: 28
<212> TYPE: DNA
<213> ORGANISM: Homo sapiens

<400> SEQUENCE: 279
gtacattcac ttaacaggct ctctttcc                               28

<210> SEQ ID NO 280
<211> LENGTH: 25
<212> TYPE: DNA
<213> ORGANISM: Homo sapiens

<400> SEQUENCE: 280
aattcatgag ctggtgtcca aggag                                  25

<210> SEQ ID NO 281
<211> LENGTH: 29
<212> TYPE: DNA
<213> ORGANISM: Homo sapiens

<400> SEQUENCE: 281
ataacagtct ccagagtata ttagcttag                              29

<210> SEQ ID NO 282
<211> LENGTH: 25
<212> TYPE: DNA
<213> ORGANISM: Homo sapiens

```
<400> SEQUENCE: 282
gttcctctgg gatgcaacat gagag                                          25

<210> SEQ ID NO 283
<211> LENGTH: 28
<212> TYPE: DNA
<213> ORGANISM: Homo sapiens

<400> SEQUENCE: 283
gaaaggatga agagggtgga tattggag                                       28

<210> SEQ ID NO 284
<211> LENGTH: 28
<212> TYPE: DNA
<213> ORGANISM: Homo sapiens

<400> SEQUENCE: 284
ccaaacctca tcatctctta cctggatt                                       28

<210> SEQ ID NO 285
<211> LENGTH: 28
<212> TYPE: DNA
<213> ORGANISM: Homo sapiens

<400> SEQUENCE: 285
gtccaaagtc aagtgcaagt atagttgg                                       28

<210> SEQ ID NO 286
<211> LENGTH: 28
<212> TYPE: DNA
<213> ORGANISM: Homo sapiens

<400> SEQUENCE: 286
acaatctttt ctgaatctga acagcttc                                       28

<210> SEQ ID NO 287
<211> LENGTH: 28
<212> TYPE: DNA
<213> ORGANISM: Homo sapiens

<400> SEQUENCE: 287
caaaggaagg catttcctaa tgatcttc                                       28

<210> SEQ ID NO 288
<211> LENGTH: 28
<212> TYPE: DNA
<213> ORGANISM: Homo sapiens

<400> SEQUENCE: 288
ctttgctttg cttttcttct tcagggaa                                       28

<210> SEQ ID NO 289
<211> LENGTH: 28
<212> TYPE: DNA
<213> ORGANISM: Homo sapiens

<400> SEQUENCE: 289
ctgcttcaag tgtatataaa ctcacagt                                       28

<210> SEQ ID NO 290
<211> LENGTH: 28
<212> TYPE: DNA
<213> ORGANISM: Homo sapiens
```

```
<400> SEQUENCE: 290
cctaggaaag cagtaactaa ttcaggag                                            28

<210> SEQ ID NO 291
<211> LENGTH: 28
<212> TYPE: DNA
<213> ORGANISM: Homo sapiens

<400> SEQUENCE: 291
gcaatttgtt cacttttagt ttcgtagc                                            28

<210> SEQ ID NO 292
<211> LENGTH: 28
<212> TYPE: DNA
<213> ORGANISM: Homo sapiens

<400> SEQUENCE: 292
ggcctaatat gcatgtgttc atgtctct                                            28

<210> SEQ ID NO 293
<211> LENGTH: 28
<212> TYPE: DNA
<213> ORGANISM: Homo sapiens

<400> SEQUENCE: 293
cagagtttct catctacgaa agaggagt                                            28

<210> SEQ ID NO 294
<211> LENGTH: 26
<212> TYPE: DNA
<213> ORGANISM: Homo sapiens

<400> SEQUENCE: 294
atcctagacc tccaggtgga atgatc                                              26

<210> SEQ ID NO 295
<211> LENGTH: 28
<212> TYPE: DNA
<213> ORGANISM: Homo sapiens

<400> SEQUENCE: 295
cttggctgtc tcaatatttt ggagtaag                                            28

<210> SEQ ID NO 296
<211> LENGTH: 28
<212> TYPE: DNA
<213> ORGANISM: Homo sapiens

<400> SEQUENCE: 296
gagtaaatga gctgtggttt ctctctta                                            28

<210> SEQ ID NO 297
<211> LENGTH: 28
<212> TYPE: DNA
<213> ORGANISM: Homo sapiens

<400> SEQUENCE: 297
ctttccatgt ggacccttta acattcag                                            28

<210> SEQ ID NO 298
<211> LENGTH: 28
<212> TYPE: DNA
```

<213> ORGANISM: Homo sapiens

<400> SEQUENCE: 298
gcatagtgag ctgttgatag agcttttg                                                28

<210> SEQ ID NO 299
<211> LENGTH: 28
<212> TYPE: DNA
<213> ORGANISM: Homo sapiens

<400> SEQUENCE: 299
ctagaacaaa atcattggct ctcctagt                                                28

<210> SEQ ID NO 300
<211> LENGTH: 27
<212> TYPE: DNA
<213> ORGANISM: Homo sapiens

<400> SEQUENCE: 300
gtctggtgag tactggctga atgtaaa                                                 27

<210> SEQ ID NO 301
<211> LENGTH: 28
<212> TYPE: DNA
<213> ORGANISM: Homo sapiens

<400> SEQUENCE: 301
ccagaggatg ctgctaaaca ttctacaa                                                28

<210> SEQ ID NO 302
<211> LENGTH: 28
<212> TYPE: DNA
<213> ORGANISM: Homo sapiens

<400> SEQUENCE: 302
gctcatgcct ggaattcacc tttatttt                                                28

<210> SEQ ID NO 303
<211> LENGTH: 28
<212> TYPE: DNA
<213> ORGANISM: Homo sapiens

<400> SEQUENCE: 303
ctaactagac atttgggcca ccttactt                                                28

<210> SEQ ID NO 304
<211> LENGTH: 28
<212> TYPE: DNA
<213> ORGANISM: Homo sapiens

<400> SEQUENCE: 304
gtctatggtg cctatagaat gtacaggt                                                28

<210> SEQ ID NO 305
<211> LENGTH: 28
<212> TYPE: DNA
<213> ORGANISM: Homo sapiens

<400> SEQUENCE: 305
ccctctcaag tttgtgagca aatatcac                                                28

<210> SEQ ID NO 306
<211> LENGTH: 26

```
<212> TYPE: DNA
<213> ORGANISM: Homo sapiens

<400> SEQUENCE: 306
ctctatcttg ctgcaatgga ctttcc                                          26

<210> SEQ ID NO 307
<211> LENGTH: 28
<212> TYPE: DNA
<213> ORGANISM: Homo sapiens

<400> SEQUENCE: 307
cctagaaaca gattttgaag ggctcttg                                        28

<210> SEQ ID NO 308
<211> LENGTH: 25
<212> TYPE: DNA
<213> ORGANISM: Homo sapiens

<400> SEQUENCE: 308
aaatgagggg catagggata aggga                                           25

<210> SEQ ID NO 309
<211> LENGTH: 28
<212> TYPE: DNA
<213> ORGANISM: Homo sapiens

<400> SEQUENCE: 309
cctagaaatc tgatacgtta tcctatga                                        28

<210> SEQ ID NO 310
<211> LENGTH: 28
<212> TYPE: DNA
<213> ORGANISM: Homo sapiens

<400> SEQUENCE: 310
aggagagata tattcaacat gaacccaa                                        28

<210> SEQ ID NO 311
<211> LENGTH: 28
<212> TYPE: DNA
<213> ORGANISM: Homo sapiens

<400> SEQUENCE: 311
gaacatctct gaccagaaat ttccagta                                        28

<210> SEQ ID NO 312
<211> LENGTH: 28
<212> TYPE: DNA
<213> ORGANISM: Homo sapiens

<400> SEQUENCE: 312
gtgtagtgaa atccttagac ttaggtaa                                        28

<210> SEQ ID NO 313
<211> LENGTH: 28
<212> TYPE: DNA
<213> ORGANISM: Homo sapiens

<400> SEQUENCE: 313
aatacatgaa aaagtaatac atggggca                                        28

<210> SEQ ID NO 314
```

```
<211> LENGTH: 28
<212> TYPE: DNA
<213> ORGANISM: Homo sapiens

<400> SEQUENCE: 314
attaaatgtt tacttctatc tacaagga                                    28

<210> SEQ ID NO 315
<211> LENGTH: 28
<212> TYPE: DNA
<213> ORGANISM: Homo sapiens

<400> SEQUENCE: 315
cattttgtga aatgcaaagg gcaaatct                                    28

<210> SEQ ID NO 316
<211> LENGTH: 28
<212> TYPE: DNA
<213> ORGANISM: Homo sapiens

<400> SEQUENCE: 316
gctgagaggc ttaattccat caagatga                                    28

<210> SEQ ID NO 317
<211> LENGTH: 28
<212> TYPE: DNA
<213> ORGANISM: Homo sapiens

<400> SEQUENCE: 317
cccatcctaa acttagtttt atgggcag                                    28

<210> SEQ ID NO 318
<211> LENGTH: 27
<212> TYPE: DNA
<213> ORGANISM: Homo sapiens

<400> SEQUENCE: 318
gtaacacatt ctctttggga agctagc                                     27

<210> SEQ ID NO 319
<211> LENGTH: 28
<212> TYPE: DNA
<213> ORGANISM: Homo sapiens

<400> SEQUENCE: 319
cttagcttca gtgaaaatgg ttcctctc                                    28

<210> SEQ ID NO 320
<211> LENGTH: 28
<212> TYPE: DNA
<213> ORGANISM: Homo sapiens

<400> SEQUENCE: 320
ctttcttagc tcctctccat ttctcttc                                    28

<210> SEQ ID NO 321
<211> LENGTH: 28
<212> TYPE: DNA
<213> ORGANISM: Homo sapiens

<400> SEQUENCE: 321
gtctatgcag tgcttcactg aggattat                                    28
```

```
<210> SEQ ID NO 322
<211> LENGTH: 28
<212> TYPE: DNA
<213> ORGANISM: Homo sapiens

<400> SEQUENCE: 322
ctctatctgc tcagagcctg cttaaaag                                        28

<210> SEQ ID NO 323
<211> LENGTH: 28
<212> TYPE: DNA
<213> ORGANISM: Homo sapiens

<400> SEQUENCE: 323
ggaaaggata cagtgttgag caagatag                                        28

<210> SEQ ID NO 324
<211> LENGTH: 28
<212> TYPE: DNA
<213> ORGANISM: Homo sapiens

<400> SEQUENCE: 324
gccaacttga ttctctttca aatgcttg                                        28

<210> SEQ ID NO 325
<211> LENGTH: 25
<212> TYPE: DNA
<213> ORGANISM: Homo sapiens

<400> SEQUENCE: 325
agatggggtt taccatgttt cccag                                           25

<210> SEQ ID NO 326
<211> LENGTH: 28
<212> TYPE: DNA
<213> ORGANISM: Homo sapiens

<400> SEQUENCE: 326
gtacagtagt tagtttccag actgatga                                        28

<210> SEQ ID NO 327
<211> LENGTH: 28
<212> TYPE: DNA
<213> ORGANISM: Homo sapiens

<400> SEQUENCE: 327
gtaaatatct aactgtgttt ccctcagt                                        28

<210> SEQ ID NO 328
<211> LENGTH: 28
<212> TYPE: DNA
<213> ORGANISM: Homo sapiens

<400> SEQUENCE: 328
gaaccaaaag gaattaagag actagggg                                        28

<210> SEQ ID NO 329
<211> LENGTH: 27
<212> TYPE: DNA
<213> ORGANISM: Homo sapiens

<400> SEQUENCE: 329
ctgcttttac ggcttcttcc tttcttc                                         27
```

<210> SEQ ID NO 330
<211> LENGTH: 26
<212> TYPE: DNA
<213> ORGANISM: Homo sapiens

<400> SEQUENCE: 330
cccacatcct tcccatttat aggcaa        26

<210> SEQ ID NO 331
<211> LENGTH: 25
<212> TYPE: DNA
<213> ORGANISM: Homo sapiens

<400> SEQUENCE: 331
tacatgatcc taagggcagc aggaa         25

<210> SEQ ID NO 332
<211> LENGTH: 25
<212> TYPE: DNA
<213> ORGANISM: Homo sapiens

<400> SEQUENCE: 332
gtttggtgca tcctctttct ctctc         25

<210> SEQ ID NO 333
<211> LENGTH: 25
<212> TYPE: DNA
<213> ORGANISM: Homo sapiens

<400> SEQUENCE: 333
gactgtagtc accccttctc caaca         25

<210> SEQ ID NO 334
<211> LENGTH: 31
<212> TYPE: DNA
<213> ORGANISM: Homo sapiens

<400> SEQUENCE: 334
agagtgaaat acatagaaaa gaaacttaaa g        31

<210> SEQ ID NO 335
<211> LENGTH: 28
<212> TYPE: DNA
<213> ORGANISM: Homo sapiens

<400> SEQUENCE: 335
atttgcgaga aacagataaa tattgaag       28

<210> SEQ ID NO 336
<211> LENGTH: 28
<212> TYPE: DNA
<213> ORGANISM: Homo sapiens

<400> SEQUENCE: 336
acaggaacaa agaatttgtt cttcatgg      28

<210> SEQ ID NO 337
<211> LENGTH: 25
<212> TYPE: DNA
<213> ORGANISM: Homo sapiens

<400> SEQUENCE: 337
ccttggattg tctcaggatg ttgca          25

```
<210> SEQ ID NO 338
<211> LENGTH: 25
<212> TYPE: DNA
<213> ORGANISM: Homo sapiens

<400> SEQUENCE: 338
ctgggatgtt tgttttggct ttgtg                                    25

<210> SEQ ID NO 339
<211> LENGTH: 30
<212> TYPE: DNA
<213> ORGANISM: Homo sapiens

<400> SEQUENCE: 339
attggtagta cactaatgga tatatgtgag                               30

<210> SEQ ID NO 340
<211> LENGTH: 27
<212> TYPE: DNA
<213> ORGANISM: Homo sapiens

<400> SEQUENCE: 340
gaataaagtg aggaaaacac ggagttg                                  27

<210> SEQ ID NO 341
<211> LENGTH: 25
<212> TYPE: DNA
<213> ORGANISM: Homo sapiens

<400> SEQUENCE: 341
gagagaggca gaaaggaggg atgaa                                    25

<210> SEQ ID NO 342
<211> LENGTH: 28
<212> TYPE: DNA
<213> ORGANISM: Homo sapiens

<400> SEQUENCE: 342
tactctgtct tcagtagctg tttcttgg                                 28

<210> SEQ ID NO 343
<211> LENGTH: 28
<212> TYPE: DNA
<213> ORGANISM: Homo sapiens

<400> SEQUENCE: 343
ttagactcac caagatcaag atgaatgc                                 28

<210> SEQ ID NO 344
<211> LENGTH: 29
<212> TYPE: DNA
<213> ORGANISM: Homo sapiens

<400> SEQUENCE: 344
atctcaataa agctgttcaa aacagaaag                                29

<210> SEQ ID NO 345
<211> LENGTH: 26
<212> TYPE: DNA
<213> ORGANISM: Homo sapiens

<400> SEQUENCE: 345
```
taaagaaaat gccatgggct gtaccc                                          26

<210> SEQ ID NO 346
<211> LENGTH: 26
<212> TYPE: DNA
<213> ORGANISM: Homo sapiens

<400> SEQUENCE: 346
attgtgcagc agaacagagt gtagtg                                          26

<210> SEQ ID NO 347
<211> LENGTH: 28
<212> TYPE: DNA
<213> ORGANISM: Homo sapiens

<400> SEQUENCE: 347
attctttgca tagctcacga aatttccc                                        28

<210> SEQ ID NO 348
<211> LENGTH: 26
<212> TYPE: DNA
<213> ORGANISM: Homo sapiens

<400> SEQUENCE: 348
aaaatgagac ctcgtatctt tgcagc                                          26

<210> SEQ ID NO 349
<211> LENGTH: 26
<212> TYPE: DNA
<213> ORGANISM: Homo sapiens

<400> SEQUENCE: 349
aaatgcagaa ctgccaaaag aaaccc                                          26

<210> SEQ ID NO 350
<211> LENGTH: 25
<212> TYPE: DNA
<213> ORGANISM: Homo sapiens

<400> SEQUENCE: 350
gagaatctgt gaatgccagg gtctg                                           25

<210> SEQ ID NO 351
<211> LENGTH: 27
<212> TYPE: DNA
<213> ORGANISM: Homo sapiens

<400> SEQUENCE: 351
atggattcat gtttcagaca tctaatt                                         27

<210> SEQ ID NO 352
<211> LENGTH: 28
<212> TYPE: DNA
<213> ORGANISM: Homo sapiens

<400> SEQUENCE: 352
atcactagaa agaaaagagt tcctattc                                        28

<210> SEQ ID NO 353
<211> LENGTH: 27
<212> TYPE: DNA
<213> ORGANISM: Homo sapiens

<400> SEQUENCE: 353
gaagtttaaa agagtgggaa catgggg 27

<210> SEQ ID NO 354
<211> LENGTH: 26
<212> TYPE: DNA
<213> ORGANISM: Homo sapiens

<400> SEQUENCE: 354
ctacgtaagc aaaaatgatc acgcac 26

<210> SEQ ID NO 355
<211> LENGTH: 25
<212> TYPE: DNA
<213> ORGANISM: Homo sapiens

<400> SEQUENCE: 355
aacctgatgg ccctcattag tcctt 25

<210> SEQ ID NO 356
<211> LENGTH: 28
<212> TYPE: DNA
<213> ORGANISM: Homo sapiens

<400> SEQUENCE: 356
caccagattt ctaggaatag catgtgag 28

<210> SEQ ID NO 357
<211> LENGTH: 25
<212> TYPE: DNA
<213> ORGANISM: Homo sapiens

<400> SEQUENCE: 357
aagagcatag tgagggtta gacct 25

<210> SEQ ID NO 358
<211> LENGTH: 29
<212> TYPE: DNA
<213> ORGANISM: Homo sapiens

<400> SEQUENCE: 358
ctttatattt agtgtagaga tcagtctcc 29

<210> SEQ ID NO 359
<211> LENGTH: 27
<212> TYPE: DNA
<213> ORGANISM: Homo sapiens

<400> SEQUENCE: 359
tgagtccttt acctaatctt ggttgtc 27

<210> SEQ ID NO 360
<211> LENGTH: 27
<212> TYPE: DNA
<213> ORGANISM: Homo sapiens

<400> SEQUENCE: 360
aatccaaagc aactctcttt tcaccac 27

<210> SEQ ID NO 361
<211> LENGTH: 26
<212> TYPE: DNA
<213> ORGANISM: Homo sapiens

<400> SEQUENCE: 361
tttactggaa ccctgatttt gttgga                                    26

<210> SEQ ID NO 362
<211> LENGTH: 26
<212> TYPE: DNA
<213> ORGANISM: Homo sapiens

<400> SEQUENCE: 362
tgccactgat atatcagtac ctgagt                                    26

<210> SEQ ID NO 363
<211> LENGTH: 27
<212> TYPE: DNA
<213> ORGANISM: Homo sapiens

<400> SEQUENCE: 363
acaatctcaa tccccttaa tgttttc                                    27

<210> SEQ ID NO 364
<211> LENGTH: 25
<212> TYPE: DNA
<213> ORGANISM: Homo sapiens

<400> SEQUENCE: 364
gtgggcagag agagtaagag aacct                                     25

<210> SEQ ID NO 365
<211> LENGTH: 28
<212> TYPE: DNA
<213> ORGANISM: Homo sapiens

<400> SEQUENCE: 365
caaaccagat tctggcagaa tagttagc                                  28

<210> SEQ ID NO 366
<211> LENGTH: 25
<212> TYPE: DNA
<213> ORGANISM: Homo sapiens

<400> SEQUENCE: 366
cttctctccc atcctccttc tccac                                     25

<210> SEQ ID NO 367
<211> LENGTH: 27
<212> TYPE: DNA
<213> ORGANISM: Homo sapiens

<400> SEQUENCE: 367
agatcaaggg atctgtggga caataac                                   27

<210> SEQ ID NO 368
<211> LENGTH: 26
<212> TYPE: DNA
<213> ORGANISM: Homo sapiens

<400> SEQUENCE: 368
ggggagtgat ttcaagcatc ctgatt                                    26

<210> SEQ ID NO 369
<211> LENGTH: 27
<212> TYPE: DNA
<213> ORGANISM: Homo sapiens

```
<400> SEQUENCE: 369
catgagtttg aggtaagatg aaggaga                                              27

<210> SEQ ID NO 370
<211> LENGTH: 26
<212> TYPE: DNA
<213> ORGANISM: Homo sapiens

<400> SEQUENCE: 370
tctctctcat cctagtgaat gccatc                                               26

<210> SEQ ID NO 371
<211> LENGTH: 26
<212> TYPE: DNA
<213> ORGANISM: Homo sapiens

<400> SEQUENCE: 371
gggtgatgat ctaccttgca ggtata                                               26

<210> SEQ ID NO 372
<211> LENGTH: 25
<212> TYPE: DNA
<213> ORGANISM: Homo sapiens

<400> SEQUENCE: 372
ctcaaggccc tgggtctgaa attac                                                25

<210> SEQ ID NO 373
<211> LENGTH: 28
<212> TYPE: DNA
<213> ORGANISM: Homo sapiens

<400> SEQUENCE: 373
acatctccag ttaataattt ccactaac                                             28

<210> SEQ ID NO 374
<211> LENGTH: 27
<212> TYPE: DNA
<213> ORGANISM: Homo sapiens

<400> SEQUENCE: 374
tggattgctc aacaaatagt gctaaaa                                              27

<210> SEQ ID NO 375
<211> LENGTH: 27
<212> TYPE: DNA
<213> ORGANISM: Homo sapiens

<400> SEQUENCE: 375
catgcgacat ccaggtagct aaaatac                                              27

<210> SEQ ID NO 376
<211> LENGTH: 28
<212> TYPE: DNA
<213> ORGANISM: Homo sapiens

<400> SEQUENCE: 376
atggataaaa atgaactttt caagagaa                                             28

<210> SEQ ID NO 377
<211> LENGTH: 28
<212> TYPE: DNA
```

```
<213> ORGANISM: Homo sapiens

<400> SEQUENCE: 377
gttttatgta aagcttcgtc atatggct                                  28

<210> SEQ ID NO 378
<211> LENGTH: 28
<212> TYPE: DNA
<213> ORGANISM: Homo sapiens

<400> SEQUENCE: 378
gttccaactt agtcataaag ttccctgg                                  28

<210> SEQ ID NO 379
<211> LENGTH: 28
<212> TYPE: DNA
<213> ORGANISM: Homo sapiens

<400> SEQUENCE: 379
gggtcttgat gttgtattga tgaggaag                                  28

<210> SEQ ID NO 380
<211> LENGTH: 28
<212> TYPE: DNA
<213> ORGANISM: Homo sapiens

<400> SEQUENCE: 380
cctaacagaa agtcactgtt tgtatctg                                  28

<210> SEQ ID NO 381
<211> LENGTH: 26
<212> TYPE: DNA
<213> ORGANISM: Homo sapiens

<400> SEQUENCE: 381
tcactctggc ttgtactctc tctgtg                                    26

<210> SEQ ID NO 382
<211> LENGTH: 28
<212> TYPE: DNA
<213> ORGANISM: Homo sapiens

<400> SEQUENCE: 382
ggctggtttc agtctggaga ctttattt                                  28

<210> SEQ ID NO 383
<211> LENGTH: 27
<212> TYPE: DNA
<213> ORGANISM: Homo sapiens

<400> SEQUENCE: 383
cttcacctcg atgacgatga tgatgat                                   27

<210> SEQ ID NO 384
<211> LENGTH: 28
<212> TYPE: DNA
<213> ORGANISM: Homo sapiens

<400> SEQUENCE: 384
gacaataaca gcacaaagga tggaaaag                                  28

<210> SEQ ID NO 385
<211> LENGTH: 25
```

<212> TYPE: DNA
<213> ORGANISM: Homo sapiens

<400> SEQUENCE: 385
gaaccagacc acacaatatc accac                                    25

<210> SEQ ID NO 386
<211> LENGTH: 28
<212> TYPE: DNA
<213> ORGANISM: Homo sapiens

<400> SEQUENCE: 386
tctacctctt tgatgtcccc ttcgatag                                 28

<210> SEQ ID NO 387
<211> LENGTH: 28
<212> TYPE: DNA
<213> ORGANISM: Homo sapiens

<400> SEQUENCE: 387
cagagtttct catctacgaa agaggagt                                 28

<210> SEQ ID NO 388
<211> LENGTH: 28
<212> TYPE: DNA
<213> ORGANISM: Homo sapiens

<400> SEQUENCE: 388
cccagctttg aaaagtatgc ctagaact                                 28

<210> SEQ ID NO 389
<211> LENGTH: 28
<212> TYPE: DNA
<213> ORGANISM: Homo sapiens

<400> SEQUENCE: 389
ctgcttcaag tgtatataaa ctcacagt                                 28

<210> SEQ ID NO 390
<211> LENGTH: 28
<212> TYPE: DNA
<213> ORGANISM: Homo sapiens

<400> SEQUENCE: 390
ttgtttcatc cactttggtg ggtaaaag                                 28

<210> SEQ ID NO 391
<211> LENGTH: 27
<212> TYPE: DNA
<213> ORGANISM: Homo sapiens

<400> SEQUENCE: 391
taattaagct ctgtgtttag ggttttt                                  27

<210> SEQ ID NO 392
<211> LENGTH: 28
<212> TYPE: DNA
<213> ORGANISM: Homo sapiens

<400> SEQUENCE: 392
caattctttg ttctttaggt cagtatat                                 28

<210> SEQ ID NO 393

```
<211> LENGTH: 25
<212> TYPE: DNA
<213> ORGANISM: Homo sapiens

<400> SEQUENCE: 393
tactcttcct cagtcccttc tctgc                                              25

<210> SEQ ID NO 394
<211> LENGTH: 25
<212> TYPE: DNA
<213> ORGANISM: Homo sapiens

<400> SEQUENCE: 394
tgagacagag catgatgatc atggc                                              25

<210> SEQ ID NO 395
<211> LENGTH: 26
<212> TYPE: DNA
<213> ORGANISM: Homo sapiens

<400> SEQUENCE: 395
gcacaagtct aggaactact ttgcac                                             26

<210> SEQ ID NO 396
<211> LENGTH: 25
<212> TYPE: DNA
<213> ORGANISM: Homo sapiens

<400> SEQUENCE: 396
gaagtatttg aaccatacgg agccc                                              25

<210> SEQ ID NO 397
<211> LENGTH: 26
<212> TYPE: DNA
<213> ORGANISM: Homo sapiens

<400> SEQUENCE: 397
tgaggaacac atccaaacta tgacac                                             26

<210> SEQ ID NO 398
<211> LENGTH: 25
<212> TYPE: DNA
<213> ORGANISM: Homo sapiens

<400> SEQUENCE: 398
tttctcgccc tcatcatctg caatg                                              25

<210> SEQ ID NO 399
<211> LENGTH: 27
<212> TYPE: DNA
<213> ORGANISM: Homo sapiens

<400> SEQUENCE: 399
tcagttgatt tcatgtgatc ctcacag                                            27

<210> SEQ ID NO 400
<211> LENGTH: 27
<212> TYPE: DNA
<213> ORGANISM: Homo sapiens

<400> SEQUENCE: 400
gaataaagtg aggaaaacac ggagttg                                            27
```

```
<210> SEQ ID NO 401
<211> LENGTH: 28
<212> TYPE: DNA
<213> ORGANISM: Homo sapiens

<400> SEQUENCE: 401
attaccttct ttctaataca agcatatg                                28

<210> SEQ ID NO 402
<211> LENGTH: 28
<212> TYPE: DNA
<213> ORGANISM: Homo sapiens

<400> SEQUENCE: 402
acaggaacaa agaatttgtt cttcatgg                                28

<210> SEQ ID NO 403
<211> LENGTH: 21
<212> TYPE: DNA
<213> ORGANISM: Artificial Sequence
<220> FEATURE:
<223> OTHER INFORMATION: Adapter i5 tag sequence

<400> SEQUENCE: 403
tacacgacgc tcttccgatc t                                       21

<210> SEQ ID NO 404
<211> LENGTH: 20
<212> TYPE: DNA
<213> ORGANISM: Artificial Sequence
<220> FEATURE:
<223> OTHER INFORMATION: Adapter i7 tag sequence

<400> SEQUENCE: 404
cttggcaccc gagaattcca                                         20

<210> SEQ ID NO 405
<211> LENGTH: 52
<212> TYPE: DNA
<213> ORGANISM: Homo sapiens

<400> SEQUENCE: 405
tagatagata gatagataga tagatagata gatagataga tagatagata ga     52

<210> SEQ ID NO 406
<211> LENGTH: 52
<212> TYPE: DNA
<213> ORGANISM: Homo sapiens

<400> SEQUENCE: 406
tagatcgata gatagataga tagatagata gatagataga tagatagata ga     52

<210> SEQ ID NO 407
<211> LENGTH: 76
<212> TYPE: DNA
<213> ORGANISM: Homo sapiens

<400> SEQUENCE: 407
tgcctgcctg cctgcctgcc tgcctgcctg ccttccttcc ttccttcctt        60
ttccttcctt ccttcc                                             76

<210> SEQ ID NO 408
<211> LENGTH: 76
<212> TYPE: DNA
```

```
<213> ORGANISM: Homo sapiens

<400> SEQUENCE: 408
tgcctgcctg cctgcctgcc tgcctgcctt ccttccttcc ttccttcctt ccttccttcc    60
ttccttcctt ccttcc                                                   76

<210> SEQ ID NO 409
<211> LENGTH: 56
<212> TYPE: DNA
<213> ORGANISM: Homo sapiens

<400> SEQUENCE: 409
tctatctatc tgtctatcta tcatctatc tatctatcta tctatctatc tatcta        56

<210> SEQ ID NO 410
<211> LENGTH: 56
<212> TYPE: DNA
<213> ORGANISM: Homo sapiens

<400> SEQUENCE: 410
tctatctgtc tatctatcta tctatctatc tatctatcta tctatctatc tatcta       56

<210> SEQ ID NO 411
<211> LENGTH: 52
<212> TYPE: DNA
<213> ORGANISM: Homo sapiens

<400> SEQUENCE: 411
tctatctatc tgtctatcta tctatctatc tatctatcta tctatctatc ta           52

<210> SEQ ID NO 412
<211> LENGTH: 52
<212> TYPE: DNA
<213> ORGANISM: Homo sapiens

<400> SEQUENCE: 412
tctatctgtc tatctatcta tctatctatc tatctatcta tctatctatc ta           52

<210> SEQ ID NO 413
<211> LENGTH: 76
<212> TYPE: DNA
<213> ORGANISM: Homo sapiens

<400> SEQUENCE: 413
tgcctgcctg cctgcctgcc tgcctgcctt ccttccttcc ttccttcctt ccttccttcc    60
ttccttcctt ccttcc                                                   76

<210> SEQ ID NO 414
<211> LENGTH: 76
<212> TYPE: DNA
<213> ORGANISM: Homo sapiens

<400> SEQUENCE: 414
tgcctgcctg cctgcctgcc tgccttcctt ccttccttcc ttccttcctt ccttccttcc    60
ttccttcctt ccttcc                                                   76

<210> SEQ ID NO 415
<211> LENGTH: 52
<212> TYPE: DNA
<213> ORGANISM: Homo sapiens

<400> SEQUENCE: 415
```

```
tctatctatc tatctatcta tctatctatc tatctatcta tctatctatc ta        52

<210> SEQ ID NO 416
<211> LENGTH: 52
<212> TYPE: DNA
<213> ORGANISM: Homo sapiens

<400> SEQUENCE: 416
tctatctgtc tatctatcta tctatctatc tatctatcta tctatctatc ta        52

<210> SEQ ID NO 417
<211> LENGTH: 48
<212> TYPE: DNA
<213> ORGANISM: Homo sapiens

<400> SEQUENCE: 417
tagatagata gatagataga tagatagata gatagataga tagataga             48

<210> SEQ ID NO 418
<211> LENGTH: 48
<212> TYPE: DNA
<213> ORGANISM: Homo sapiens

<400> SEQUENCE: 418
tagatcgata gatagataga tagatagata gatagataga tagataga             48

<210> SEQ ID NO 419
<211> LENGTH: 48
<212> TYPE: DNA
<213> ORGANISM: Homo sapiens

<400> SEQUENCE: 419
tagatagata gatagataga tagatagata gatagataga tagataga             48

<210> SEQ ID NO 420
<211> LENGTH: 48
<212> TYPE: DNA
<213> ORGANISM: Homo sapiens

<400> SEQUENCE: 420
tagatcgata gatagataga tagatagata gatagataga tagataga             48

<210> SEQ ID NO 421
<211> LENGTH: 48
<212> TYPE: DNA
<213> ORGANISM: Homo sapiens

<400> SEQUENCE: 421
tctatctatc tgtctatcta tctatctatc tatctatcta tctatcta             48

<210> SEQ ID NO 422
<211> LENGTH: 52
<212> TYPE: DNA
<213> ORGANISM: Homo sapiens

<400> SEQUENCE: 422
tctatctatc tgtctatcta tctatctatc tatctatcta tctatctatc ta        52

<210> SEQ ID NO 423
<211> LENGTH: 52
<212> TYPE: DNA
<213> ORGANISM: Homo sapiens
```

```
<400> SEQUENCE: 423
tctatctatc tatctatcta tctatctatc tatctatcta tctatctatc ta            52

<210> SEQ ID NO 424
<211> LENGTH: 52
<212> TYPE: DNA
<213> ORGANISM: Homo sapiens

<400> SEQUENCE: 424
tctatctgtc tatctatcta tctatctatc tatctatcta tctatctatc ta            52

<210> SEQ ID NO 425
<211> LENGTH: 40
<212> TYPE: DNA
<213> ORGANISM: Homo sapiens

<400> SEQUENCE: 425
tctatctatc tatctatcta tctatctatc tatctatcta                          40

<210> SEQ ID NO 426
<211> LENGTH: 52
<212> TYPE: DNA
<213> ORGANISM: Homo sapiens

<400> SEQUENCE: 426
tatctatcta tctatctatc tatctatcta tctatctatc tatcaatcaa tc            52

<210> SEQ ID NO 427
<211> LENGTH: 56
<212> TYPE: DNA
<213> ORGANISM: Homo sapiens

<400> SEQUENCE: 427
tatctatcta tctatctatc tatctatcta tctatctatc tatctatcaa tcaatc        56

<210> SEQ ID NO 428
<211> LENGTH: 52
<212> TYPE: DNA
<213> ORGANISM: Homo sapiens

<400> SEQUENCE: 428
tatctatcta tctatctatc tatctatcta tctatctatc tatctatcaa tc            52

<210> SEQ ID NO 429
<211> LENGTH: 56
<212> TYPE: DNA
<213> ORGANISM: Homo sapiens

<400> SEQUENCE: 429
tatctatcta tctatctatc tatctatcta tctatctatc tatctatcta tcaatc        56
```

METHODS AND COMPOSITIONS FOR DNA PROFILING

RELATED APPLICATIONS

This application claims priority to U.S. Provisional Application No. 62/103,524 filed Jan. 14, 2015, U.S. Provisional Application No. 62/043,060 filed Aug. 28, 2014, and U.S. Provisional Application No. 61/940,942 filed Feb. 18, 2014, the contents of which are incorporated herein by reference in their entireties.

REFERENCE TO SEQUENCE LISTING, TABLE, OR COMPUTER PROGRAM LISTING

The present application is being filed along with a Sequence Listing in electronic format. The Sequence Listing is provided as a file entitled IP-1192-US_SL.txt, created Mar. 7, 2018, which is 59,789 bytes in size. The information in the electronic format of the Sequence Listing is incorporated herein by reference in its entirety.

FIELD OF THE DISCLOSURE

Embodiments provided herein relate to methods and compositions for DNA profiling. Some embodiments relate to methods of amplification of target sequences of variant sizes in a single reaction, followed by subsequent sequencing of the library.

BACKGROUND OF THE DISCLOSURE

Historically, the use of a subset of markers in a human genome has been utilized to determine an individual's personal identity, or DNA fingerprint or profile. These markers include locations or loci of short tandem repeated sequences (STRs) and intermediate tandem repeated sequences (ITRs) which in combination are useful in identifying one individual from another on a genetic level. The analysis of these markers has become standardized in the analysis of DNA found at crime scenes. For example, in the United States a number of these repeated sequences have been combined to create a Combined DNA Index System (CODIS), which serve as the laboratory standard for DNA profiling in criminal cases. Other countries similarly have adopted a standard system for DNA profiling. These systems have also been utilized to determine paternity and familial relationships. However, the current systems are all based on size separation of these repeated loci on an electrophoretic system and are thus limited to the number of loci that can be differentiated in such a system. For example, some of the current commercial systems for DNA profiling for forensics purposes differentiate only 16 markers due to the limitations of the electrophoretic detection methods.

SUMMARY OF THE DISCLOSURE

Embodiments relate to systems and methods that are not content limited and that bring different pieces of genetic information about an individual together to provide a comprehensive, more complete DNA profile of an individual. The present disclosure describes methods and compositions that enable this profile of an individual, thereby advancing the fields of personal and forensic genomics.

DNA profiling currently uses selected biological markers for determining the identity of a DNA sample. For example, the most common analysis for determining a DNA profile is to determine the profile for a number of short tandem repeated (STRs) sequences found in an organism's genome. The analysis consists of amplifying defined STR sequences that can be up to 400 bp long that can be differentiated by size on an electrophoretic gel or by using capillary electrophoresis (CE). Electrophoresis is used to detect size changes due to differences in the number of repeated STRs at a given locus and as such the length of the PCR amplicons, which for the CE system is between 50-500 bp. To help overcome the limits imposed by size differentiation methodologies (i.e., STRs of overlapping amplicon size cannot be differentiated), current methods of DNA profiling utilize different sets of labelled primers such that amplicons that overlap in size can be labelled with different fluorescent dyes whereon, upon excitation, the emission spectra differ thereby allowing for overlapping amplicons to be differentiated using differences in the dye excitation and emission spectra. Using differentiated labeling, current methods allow for the multiplexing of 24 different STR loci using 6 differently detectable dyes in one DNA profiling run.

There are many limitations to the current DNA profiling methodologies. As previously mentioned, size differentiated systems limit the number of loci that can be discretely determined at a given time. Another limitation of the established methods for DNA profiling is that the DNA to be analyzed oftentimes is degraded and the size range of some of the markers does not accommodate degraded DNA, for example the amplicons can be larger than the size of the fragments of the degraded DNA. For degraded DNA, amplicons of 400 bp are considered very long and can result in loss of amplification of those longer loci. When DNA analysts amplify degraded DNA samples to identify their STR profile, for example a sample found at a crime scene, oftentimes they are unable to detect all the loci resulting in a partial profile which can make matching a suspect in a crime scene to a crime sample difficult or impossible. As a default with such samples, a DNA analyst has little choice and if any sample is left over, additional assays need to be performed to identify other markers which might give a clue as to the identity of the individual, such as single nucleotide polymorphisms (SNPs), mini-STRs, or mitochondrial DNA (mtDNA) analysis. However, precious sample must be expended on each assay with no certainty of success in finally identifying an individual. FIG. 1A demonstrates the potential different paths to DNA identification, all of which are separate workflows and require aliquots of precious samples. When one or more simple workflows need to be combined and potentially repeated multiple times then the resulting process is no longer simple or an effective use of a precious sample.

Embodiments described in the present application provide methods, compositions and systems for determining the DNA profile of an individual or organism by next generation sequencing (NGS) thereby providing a solution to the problems and limitations of current methodologies for DNA profiling. FIG. 1B shows an exemplary workflow of the disclosed methods in one embodiment. Disclosed herein are methods and compositions for combining a multitude of forensically relevant markers into one assay including, but not limited to, short tandem repeats (STRs), intermediate tandem repeats (ITRs), identity informative single nucleotide polymorphisms (iSNPs), ancestry informative single nucleotide polymorphisms (aSNPs) and phenotypic informative single nucleotide polymorphisms (pSNPs).

The present disclosure describes assays that overcome the limitations of current methodologies for DNA profiling. Disclosed embodiments provide methods and compositions for multiplex amplification, library preparation and sequencing of combined STRs, ITRs, iSNPs, aSNPs, and pSNPs from one nucleic acid sample in a single multiplex reaction. Disclosed methods analyze a plurality of markers in one experimental assay with minimal sample handling, using low amounts of sample DNA including degraded DNA. Some embodiments described can be utilized for databanking DNA profiles and/or DNA profiles that can be used for criminal casework. Some embodiments provide PCR methods and compositions developed to be sensitive enough to detect sub-nanogram amounts of DNA. Further, the unconventional primer design parameters allow for highly multiplexed PCR for the identification of STRs, ITRs and SNPs in one multiplex reaction. For criminal casework, the present methods and compositions incorporate unique molecule identifiers (UMIs) which aide in removal of, for example, PCR and sequencing errors, stutter and the like from sequencing results. See Kivioja et al., Nat. Meth. 9, 72-74 (2012). As well, the results from the methods and compositions disclosed herein are compatible with existing databases.

Therefore, embodiments disclosed herein provide methods for constructing a DNA profile comprising: providing a nucleic acid sample, amplifying the nucleic acid sample with a plurality of primers that specifically hybridize to at least one target sequence comprising a single nucleotide polymorphism (SNP) and at least one target sequence comprising a tandem repeat in a multiplex reaction to generate amplification products, and determining the genotypes of the at least one SNP and the at least one tandem repeat in the amplification products, thereby constructing the DNA profile of the nucleic acid sample.

In some embodiments, the methods comprise generating a nucleic acid library from the amplification products. In some embodiments, the methods comprise determining the sequences of the nucleic acid library. In some embodiments, the nucleic acid sample is from a human. In some embodiments, the nucleic acid sample is from an environmental sample, a plant, a non-human animal, a bacterium, archaea, a fungus, or a virus. In some embodiments, the DNA profile is used for one or more of disease diagnostics or prognosis, cancer biomarker identification, genetic anomaly identification or genetic diversity analysis. In some embodiments, the DNA profile is used for one or more of databanking, forensics, criminal case work, paternity or personal identification. In some embodiments, the at least one SNP indicates the ancestry or a phenotypic characteristic of the source of the nucleic acid sample. In some embodiments, each of the plurality of primers has a low melting temperature and/or has a length of at least 24 nucleotides. In some embodiments, each of the plurality of primers has a melting temperature that is less than 60 degrees C. In some embodiments, each of the plurality of primers has a melting temperature that is about 50 degrees C. to about 60 degrees C. In some embodiments, each of the plurality of primers has a length of at least 24 nucleotides. In some embodiments, each of the plurality of primers has a length of about 24 nucleotides to about 38 nucleotides. In some embodiments, each of the plurality of primers comprises a homopolymer nucleotide sequence. In some embodiments, the nucleic acid sample is amplified by polymerase chain reaction (PCR). In some embodiments, the nucleic acid sample is amplified in an amplification buffer having a salt concentration that is increased compared to the salt concentration of an amplification buffer used in conjunction with conventionally designed primers. In some embodiments, the salt comprises KCl, LiCl, NaCl, or a combination thereof. In some embodiments, the salt comprises KCl. In some embodiments, the concentration of KCl in the amplification buffer is about 100 mM to about 200 mM. In some embodiments, the concentration of KCl in the amplification buffer is less than about 150 mM. In some embodiments, the concentration of KCl in the amplification buffer is about 145 mM. In some embodiments, the SNP is an ancestry SNP, a phenotypic SNP, an identity SNP, or a combination thereof. In some embodiments, the plurality of primers specifically hybridize to at least 30 SNPs. In some embodiments, the plurality of primers specifically hybridize to at least 50 SNPs. In some embodiments, the tandem repeat is a short tandem repeats (STR), an intermediate tandem repeat (ITR), or a variant thereof. In some embodiments, the plurality of primers specifically hybridize to at least 24 tandem repeat sequences. In some embodiments, the plurality of primers specifically hybridize to at least 60 tandem repeat sequences. In some embodiments, the nucleic acid sample comprises about 100 pg to about 100 ng DNA. In some embodiments, the nucleic acid sample comprises about 10 pg to about 100 pg DNA. In some embodiments, the nucleic acid sample comprises about 5 pg to about 10 pg DNA. In some embodiments, the nucleic acid sample comprises genomic DNA. In some embodiments, the genomic DNA is from a forensic sample. In some embodiments, the genomic DNA comprises degraded DNA. In some embodiments, at least 50% of the genotypes of the at least one SNP and at least one tandem repeat are determined. In some embodiments, at least 80% of the genotypes of the at least one SNP and at least one tandem repeat are determined. In some embodiments, at least 90% of the genotypes of the at least one SNP and at least one tandem repeat are determined. In some embodiments, at least 95% of the genotypes of the at least one SNP and at least one tandem repeat are determined. In some embodiments, each of the plurality of primers comprises one or more tag sequences. In some embodiments, the one or more tag sequences comprise a primer tag, a capture tag, a sequencing tag, a unique molecular identifier tag, or a combination thereof. In some embodiments, the one or more tag sequences comprise a primer tag. In some embodiments, the one or more tag sequences comprise a unique molecular identifier tag.

Embodiments disclosed herein provide methods of constructing a nucleic acid library comprising: providing a nucleic acid sample, and amplifying the nucleic acid sample with a plurality of primers that specifically hybridize to at least one target sequence comprising a single nucleotide polymorphism (SNP) and at least one target sequence comprising a tandem repeat sequence in a multiplex reaction to generate amplification products.

In some embodiments, the nucleic acid sample is not fragmented prior to the amplification. In some embodiments, the target sequences are not enriched prior to the amplification. In some embodiments, the at least one SNP indicates the ancestry or a phenotypic characteristic of the source of the nucleic acid sample. In some embodiments, each of the plurality of primers comprises one or more tag sequences. In some embodiments, the one or more tag sequences comprise a primer tag, a capture tag, a sequencing tag, or a unique molecular identifier tag, or a combination thereof. In some embodiments, the methods include amplifying the amplification products with a second plurality of primers. In some embodiments, each of the second plurality of primers comprises a portion corresponding to the primer tag of the plurality of primers and one or more tag sequences. In some embodiments, the one or more tag sequences of the second plurality of primers comprise a capture tag, or a sequencing tag, or a combination thereof. In some embodiments, the methods include adding single stranded-binding protein (SSB) to the amplification products. In some embodiments, the nucleic acid sample and/or the amplification products are amplified by polymerase chain reaction (PCR). In some embodiments, the nucleic acid sample and/or the amplification products are amplified in an amplification buffer having a salt concentration that is increased compared to the salt concentration of an amplification buffer used in conjunction with conventionally designed primers. In some embodiments, the salt comprises KCl, LiCl, NaCl, or a combination thereof. In some embodiments, the salt comprises KCl. In some embodiments, the concentration of KCl in the amplification buffer is about 100 mM to about 200 mM. In some embodiments, the concentration of KCl in the amplification buffer is less than about 150 mM. In some embodiments, the concentration of KCl in the amplification buffer is about 145 mM.

Embodiments disclosed herein provide a nucleic acid library comprising a plurality of nucleic acid molecules, wherein the plurality of nucleic acid molecules comprise at least one tandem repeat sequence flanked by a first pair of tag sequences and at least one single nucleotide polymorphism (SNP) sequence flanked by a second pair of tag sequences. Further provided is a nucleic acid library constructed using the methods and compositions disclosed herein. In some embodiments, the at least one SNP indicates the ancestry or a phenotypic characteristic of the source of the plurality of nucleic acid molecules.

Embodiments disclosed herein provide a plurality of primers that specifically hybridize to at least one short target sequence and at least one long target sequence in a nucleic acid sample, wherein amplifying the nucleic acid sample using the plurality of primers in a single multiplex reaction results in at least one short amplification product and at least one long amplification product, wherein each of the plurality of primers comprises one or more tag sequences.

In some embodiments, the short target sequence comprises a single nucleotide polymorphism (SNP) and the long target sequence comprises a tandem repeat. In some embodiments, the one or more tag sequences comprise a primer tag, a capture tag, a sequencing tag, a unique molecular identifier tag, or a combination thereof. In some embodiments, each of the plurality of primers has a low melting temperature and/or has a length of at least 24 nucleotides. In some embodiments, each of the plurality of primers has a melting temperature that is less than 60 degrees C. In some embodiments, each of the plurality of primers has a melting temperature that is about 50 degrees C. to about 60 degrees C. In some embodiments, each of the plurality of primers has a length of at least 24 nucleotides. In some embodiments, each of the plurality of primers has a length of about 24 nucleotides to about 38 nucleotides. In some embodiments, each of the plurality of primers comprises a homopolymer nucleotide sequence. In some embodiments, the nucleic acid sample is amplified by polymerase chain reaction (PCR). In some embodiments, the SNP is an ancestry SNP, a phenotypic SNP, an identity SNP, or a combination thereof. In some embodiments, the plurality of primers specifically hybridize to at least 30 SNPs. In some embodiments, the plurality of primers specifically hybridize to at least 50 SNPs. In some embodiments, the tandem repeat is a short tandem repeats (STR), an intermediate tandem repeat (ITR), or a variant thereof. In some embodiments, the plurality of primers specifically hybridize to at least 24 tandem repeat sequences. In some embodiments, the plurality of primers specifically hybridize to at least 60 tandem repeat sequences.

Embodiments disclosed herein provide kits comprising at least one container means, wherein the at least one container means comprises a plurality of primers disclosed herein.

In some embodiments, the kits include a reagent for an amplification reaction. In some embodiments, the reagent is an amplification buffer for polymerase chain reaction (PCR). In some embodiments, the amplification buffer comprises a salt concentration that is increased compared to the salt concentration of an amplification buffer used in conjunction with conventionally designed primers. In some embodiments, the salt comprises KCl, LiCl, NaCl, or a combination thereof. In some embodiments, the salt comprises KCl. In some embodiments, the concentration of KCl in the amplification buffer is about 100 mM to about 200 mM. In some embodiments, the concentration of KCl in the amplification buffer is less than about 150 mM. In some embodiments, the concentration of KCl in the amplification buffer is about 145 mM.

BRIEF DESCRIPTION OF THE DRAWINGS

FIG. 1A and FIG. 1B show the differences in the A) current workflow for DNA profiling versus B) that of one exemplary embodiment of the present disclosure.

FIG. 5A, FIG. 5B, FIG. 5C, FIG. 5D and FIG. 5E are box plots showing exemplary results for an experiment following the workflow outlined in FIG. 2, which was used to identify a panel of 56 STRs and mix of 75 identity-informative SNPs (iSNPs), ancestry-informative SNPs (aSNPs) and phenotypic-informative SNPs (pSNPs) in a multiplex amplification and sequencing reaction from a sample. Reported are replicated results demonstrating successful amplification and sequencing of the STR loci from the panel; A) box plot demonstrating intra-locus balance for 25 heterozygous STRs from the panel, B) box plot demonstrating low stutter for the majority of the 56 STR loci, C) box plot demonstrating sequencing coverage for the STR loci, D) box plot demonstrating the sequence coverage for the SNPs, and E) box plot demonstrating balance for 22 heterozygous SNPs from the panel. The lower error bar indicates the minimum value, the upper error bar indicates the maximum value, the lower box reports the $25^{th}$ percentile and the upper box reports the $75^{th}$ percentile with the mean being the intersection between the lower and upper boxes.

FIG. 7A, FIG. 7B, FIG. 7C, FIG. 7D and FIG. 7E are box plots showing exemplary results for an experiment following the workflow outlined in FIG. 3, which was used to identify a panel of 26 STRs and a mix of 94 iSNPs, aSNPs and pSNPs in a multiplex amplification and sequencing reaction from a sample. Reported are replicated results demonstrating successful amplification and sequencing of the STRs from the panel; A) box plot demonstrating intra-locus balance for 21 heterozygous STR loci from the panel, B) box plot demonstrating low stutter for the 26 STR loci (39 of the 47 alleles of the 26 loci showed no stutter), C) box plot demonstrating sequencing coverage for the STR loci (read numbers normalized using the UMIs), D) box plot demonstrating the sequence coverage for the SNPs and E) box plot demonstrating balance for 21 heterozygous iSNPs from the panel. The lower error bar indicates the minimum value, the upper error bar indicates the maximum value, the lower box reports the $25^{th}$ percentile and the upper box reports the $75^{th}$ percentile with the mean being the intersection between the lower and upper boxes.

FIG. 10A and FIG. 10B show exemplary results from an experiment where the DNA ratio was 90:10 female:male. A) a subset of STR loci call results for STR loci when using current capillary electrophoresis DNA profiling methods, and B) several STR loci call results for several STR loci when using the methods of the present application. Both the CE methods and the methods of the present application did detect the low level of male DNA contamination.

FIG. 12 is a table that shows exemplary high level sequencing results from an experiment using 12 sample individuals and a reference individual, demonstrating consistency of STR and SNP calls between two replications.

FIG. 13 is a table that shows exemplary population statistics from the experiment shown in FIG. 12.

FIG. 14 is a table that shows exemplary phenotype predictions based on genotype of pSNPs from the experiment shown in FIG. 12.

FIG. 16A, FIG. 16B, FIG. 16C, FIG. 16D and FIG. 16E are bar charts showing the exemplary STR loci plots from the experiment of FIG. 12.

FIG. 20 is a table that shows exemplary isometric heterozygotes in STR loci from the experiment of FIG. 12. Sequences represented include Sample 3/Locus D9S1122/Repeat Number 13 (TAGATAGATAGATAGATAGATAGA-TAGATAGATAGATAGATAGATAGATAGA) (SEQ ID NO:405); Sample 3/Locus D9S1122/Repeat Number 13 (TAGATCGATAGATAGATAGATAGATAGATAGATA-GATAGATAGATAGATAGA) (SEQ ID NO:406); Sample 7/D2S1338/Repeat Number 19 (TGCCTGCCTGCCTGC-CTGCCTGCCTGCCTGCCTTCCTTCCTTCCTTCCTTC-CTTCC TTCCTTCCTTCCTTCCTTCC) (SEQ ID NO: 407); Sample 7/D2S1338/Repeat Number 19 (TGCCTGC-CTGCCTGCCTGCCTGCCTTCCTTCCTTCCTTC-CTTCCTTCCTTCC TTCCTTCCTTCCTTCC) (SEQ ID NO: 408); Sample 13/D8S1179/Repeat Number 14 (TCTATCTATCTGTCTATCTATCTATCTATCTATCTATC-TATCTATCTATCTATCTA) (SEQ ID NO:409); Sample 13/D8S1179/Repeat Number 14 (TCTATCT[[A]]GTC-TATCTATCTATCTATCTATCTATCTATCTATCTATC-TATCTAT CTA) (SEQ ID NO:410); Sample 14/D8S1179/ Repeat Number 13 (TCTATCTATCTGTCTATCTATCTATCTATCTATCTATC-TATCTATCTATCTA (SEQ ID NO:411); Sample 14/D8S1179/Repeat Number 13 (TCTATCTGTCTATC-TATCTATCTATCTATCTATCTATCTATCTATCTA (SEQ ID NO:412); Sample 15/D2S1338/Repeat Number 19 (TGCCTGCCTGCCTGCCTGCCTGCCTGCCTTCCTTC-CTTCCTTCCTTCCTTCCTTCC TTCCTTCCTTCCTTCC-CTTCC) (SEQ ID NO:413); Sample 15/D2S1338/Repeat Number 19 (TGCCTGCCTGCCTGCCTGCCTGCCTTC-CTTCCTTCCTTCCTTCCTTCCTTCCTTCCT TCCTTC-CTTCCTTCC) (SEQ ID NO:414); Sample 17/D8S1179/Repeat Number 13 (TCTATCTATCTATC-TATCTATCTATCTATCTATCTATCTATCTATCTATCTA) (SEQ ID NO:415); Sample 17/D8S1179/Repeat Number 13 (TCTATCTGTCTATCTATCTATCTATCTATCTATCTATC-TATCTATCTATCTA) (SEQ ID NO:416); Sample 17/D9S1122/Repeat Number 12 (TAGATAGATAGATA-GATAGATAGATAGATAGATAGATAGATAGATAGA) (SEQ ID NO:417); Sample 17/D9S1122/Repeat Number 12 (TAGATCGATAGATAGATAGATAGATAGATAGATA-GATAGATAGA) (SEQ ID NO:418); 2800M/ D9S1122/Repeat Number 12 (TAGATAGATAGATAGATA-GATAGATAGATAGATAGATAGATAGATAGA) (SEQ ID NO:419); 2800M/D9S1122/Repeat Number 12 (TAGATC-GATAGATAGATAGATAGATAGATAGATAGATAGATA-GATAGA) (SEQ ID NO:420).

[AATC]2 (SEQ ID NO:427); [TATC]11 TATCAATC (SEQ ID NO:428); [TATC]12 TATCAATC (SEQ ID NO:429).

FIG. 23 is a table that shows exemplary genotyping results using degraded DNA.

Figures 24A, 24B:
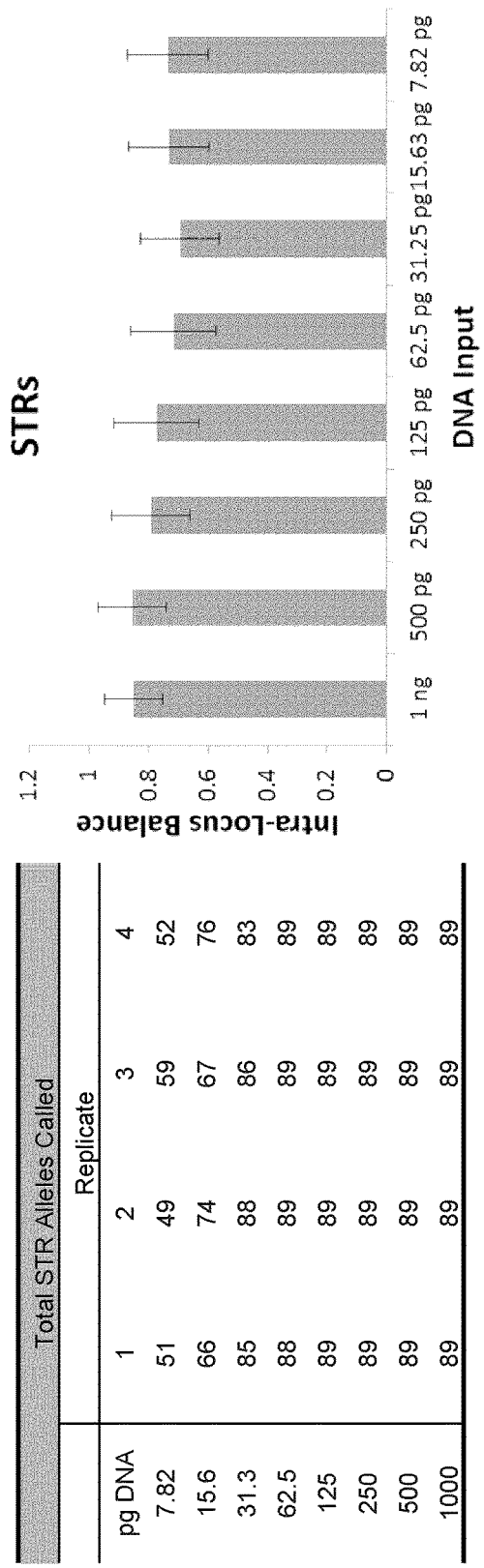

FIG. 24A and FIG. 24B show exemplary STR genotyping results and intro-locus balance at difference DNA inputs.

Figures 25A, 25B:
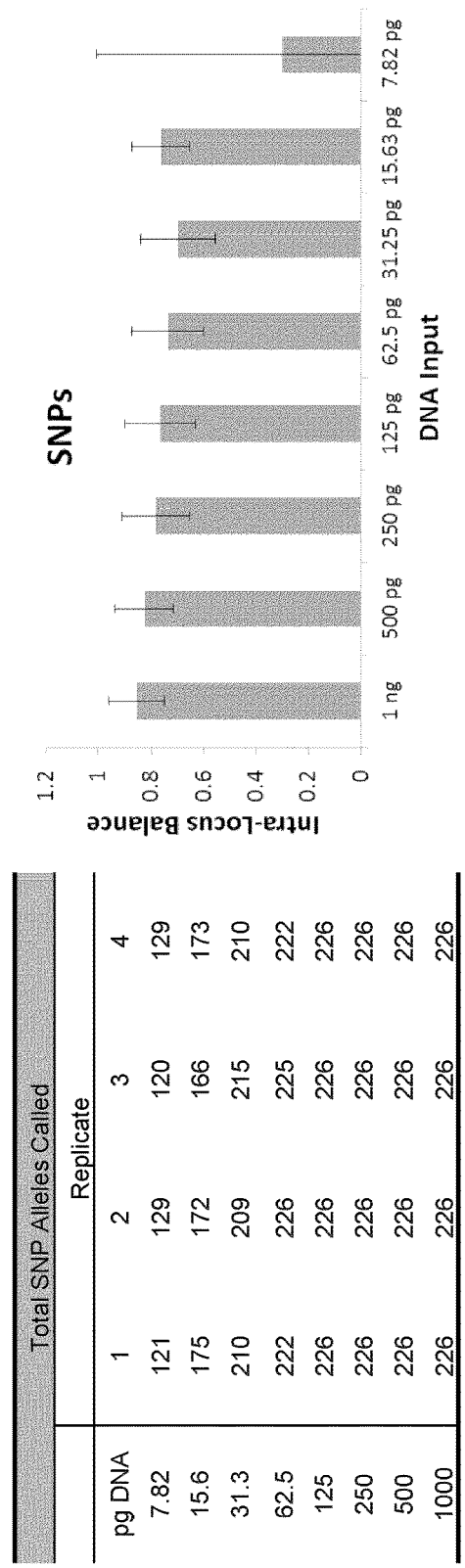

FIG. 25A and FIG. 25B show exemplary SNP genotyping results and intro-locus balance at difference DNA inputs.

DETAILED DESCRIPTION

Definitions

All patents, applications, published applications and other publications referred to herein are incorporated by reference to the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the singular forms "a", "an", and "the" include plural references unless indicated otherwise, expressly or by context. For example, "a" dimer includes one or more dimers, unless indicated otherwise, expressly or by context.

As used herein, the terms "DNA profile," "genetic fingerprint," and "genotypic profile" are used interchangeably herein to refer to the allelic variations in a collection of polymorphic loci, such as a tandem repeat, a single nucleotide polymorphism (SNP), etc. A DNA profile is useful in forensics for identifying an individual based on a nucleic acid sample. DNA profile as used herein may also be used for other applications, such as diagnosis and prognosis of diseases including cancer, cancer biomarker identification, inheritance analysis, genetic diversity analysis, genetic anomaly identification, databanking, forensics, criminal case work, paternity, personal identification, etc.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, "sequence identity" or "identity" or "homology" in the context of two nucleotide sequences includes reference to the residues in the two sequences which are the same when aligned for maximum correspondence over a specified comparison window. The portion of the nucleotide sequence in the comparison window may comprise additions or deletions (i.e., gaps) as compared to the reference sequence for optimal alignment of the two sequences. The percentage is calculated by determining the number of positions at which the identical nucleic acid base residue occurs in both sequences to yield the number of matched positions, dividing the number of matched positions by the total number of positions in the window of comparison and multiplying the result by 100 to yield the percentage of sequence identity.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Methods for Constructing a DNA Profile

Established methodologies for determining the DNA profile are limited in a number of ways. For example, current methods detect size changes of amplified loci which differ due to changes in lengths of tandem repeated sequences found in a DNA sample. To multiplex STR amplifications for visualization, the amplifications have to be designed to space the different amplicons sizes within the size separation limits of the electrophoretic system, which for CE is from about 50-500 bp. As such, only a limited number of the repeated sequences can be visualized in one assay. For example, the GLOBALFILER PCR amplification kit (APPLIED BIOSYSTEMS) is reportedly able to differentiate 24 STR loci by using 6 different dyes. Further, such methods have issues when sample DNA is degraded as is common with DNA samples from a crime scene, such that longer amplification products are not possible resulting in an incomplete DNA profile. Current methods are also oftentimes not sensitive enough to detect small amounts of contaminating DNA so a mixed sample can go undetected and unreported, which could be critical for criminal casework. As such, current methods can lead to incomplete results which lead to inconclusive results, which can be detrimental for DNA profiling.

Additionally, current targets do not include information about sample ancestry, phenotypic traits such as possible eye color and other individualized sample information. Some sequencing methodologies have attempted to include both STR and SNP detection. For example, library preparation followed by custom enrichment for STRs and SNPs has been attempted, however not all STRs are completely covered as library preparation methods typically involve sample shearing that can obliterate the targeted sequence. Further, established primer design methods and protocols can provide primer sets for amplifying long sequences (e.g., STRs) or short sequences (e.g., SNPs), but the combinations of both in one reaction have not met with success.

The present disclosure describes solutions to the problems and limitations of the current DNA profiling systems. Methods and compositions described herein allow for the combination of STRs and SNPs into one assay using PCR to amplify the targets and generate libraries for sequencing. While developing the present assays, it was unexpectedly discovered that, for example, when utilizing unconventional and counterintuitive primer design, both STRs and SNPs can be amplified in one reaction which allows the sequence for all targeted loci to be determined. Surprisingly, when designing amplification primers using parameters contrary to the current dogma surrounding primer design, primers were created that allowed for the longer STR regions to be amplified and the short SNP regions to be amplified in a more or less balanced manner thereby allowing for both STRs and SNPs to be multiplex amplified together.

The methods and compositions disclosed herein for determining the DNA profile of an organism can be used whenever differently sized sets of amplicons are desired from one amplification reaction outside of DNA profiling. For example, if targets of interest for PCR include both large gene regions and short SNP regions which may result in amplicons that vary in size from hundreds to thousands of base pairs versus amplicons of less than 100 base pairs, respectively, then the methods and compositions described herein could allow for successful simultaneous amplification of the gene and SNP targets which would not have been possible without practicing the disclosed methods. Further, the methods and compositions disclosed herein may apply to any organism, for example humans, non-human primates, animals, plants, viruses, bacteria, fungi and the like. As such, the present methods and compositions are not only useful for DNA profiling (e.g., forensics, paternity, individual identification, etc.) and humans as a target genome, but could also be used for other targets such as cancer and disease markers, genetic anomaly markers and/or when the target genome is not human based.

Therefore, embodiments disclosed herein provide methods for constructing a DNA profile comprising: providing a nucleic acid sample, amplifying the nucleic acid sample with a plurality of primers that specifically hybridize to at least one target sequence comprising a single nucleotide polymorphism (SNP) and at least one target sequence comprising a tandem repeat, and determining the genotypes of the at least one SNP and at least one tandem repeat in the amplification products, thereby constructing the DNA profile of the nucleic acid sample.

It would be appreciated by those skilled in the art that any suitable techniques may be used in determining the genotypes of the target sequences including, but not limited to, array-based hybridization, sequencing, or the like. Therefore, in some embodiments, the methods disclosed herein may comprise generating a nucleic acid library, such as a sequencing library, from the amplification products, and determining the sequences of the nucleic acid library.

In some embodiments, the present disclosure provides methods and compositions for DNA profiling that comprise the concurrent identification of STRs and iSNPs, for example for use in population or personal databanking. In such databanks, personal data is not necessarily needed as the individuals are typically known. However, if additional information is desired then additional information targets can be added for concurrent identification. Short tandem repeats are well known in the art, and consist of repeated di- or tri nucleotide sequences. Intermediate tandem repeats are typically considered repeated sequences of between 4 to 7 nucleotide sequences. SNPs utilized herein can be of any form that might offer insight into a person's physical characteristics. Those exemplified herein are SNPs that provide clues for ancestry or heritage (aSNPs) and those that provide clues for phenotypic characteristics (phenotypic-informative SNPs). In methods described herein, a DNA profile assay might include any number of these SNPs in combination with STR and ITR loci determinations.

For example, the present disclosure provides additional methods and compositions where, along with STRs and iSNPS, additional targets are included. If more information about an individual is desired, for example when a sample belongs to an unknown individual or group of individuals as can be the case for criminal casework, the other information markers can be added to the STR and iSNPs, such as SNPs related to ancestry (aSNPs) and SNPs related to phenotypic variants (phenotypic-informative SNPs). The additional information can then be used to aid investigators, for example, by providing insight into an unknown individual's heritage, eye color, hair color, and the like. As such, the addition of all the combined information can provide a more complete DNA profile of an individual that was not previously known using current methods of DNA profiling.

The methods and compositions disclosed herein are designed to be sensitive enough to detect sub-nanogram amounts of nucleic acid molecules. Further, the methods and compositions disclosed herein may be useful to amplify a nucleic acid sample made having low-quality nucleic acid molecules, such as degraded and/or fragmented genomic DNA from a forensic sample. The nucleic acid sample may be a purified sample or a crude DNA containing lysate, for example derived from a buccal swap, paper, fabric or other substrate that may be impregnated with saliva, blood, or other bodily fluids. As such, in some embodiments, the nucleic acid sample may comprise low amounts of, or fragmented portions of DNA, such as genomic DNA. For example, the nucleic acid sample may comprise an amount of nucleic acid (e.g., genomic DNA) that is, is about, or is less than, 1 pg, 2 pg, 3 pg, 4 pg, 5 pg, 6 pg, 7 pg, 8 pg, 9 pg, 10 pg, 11 pg, 12 pg, 13 pg, 14 pg, 15 pg, 16 pg, 17 pg, 18 pg, 19 pg, 20 pg, 30 pg, 40 pg, 50 pg, 60 pg, 70 pg, 80 pg, 90 pg, 100 pg, 200 pg, 300 pg, 400 pg, 500 pg, 600 pg, 700 pg, 800 pg, 900 pg, 1 ng, 10 ng, 100 ng, or is in a range defined by any two of these values, for example, 10 pg to 100 pg, 10 pg to 1 ng, 100 pg to 1 ng, 1 ng to 10 ng, 10 ng to 100 ng, etc. In some embodiments, the nucleic acid sample may comprise an amount of nucleic acid (e.g., genomic DNA) that is about 100 pg to about 1 ng. In some embodiments, the nucleic acid sample may comprise an amount of nucleic acid (e.g., genomic DNA) that is more than about 62.5 pg. In some embodiments, additional fragmentation steps, such as sonication or endonuclease digestion, are not included in the fragmentation procedures.

In some embodiments, the methods and compositions disclosed herein are capable of successfully determining the genotypes of one or more of the target sequences, for example, SNPs, STRs, etc., even with sub-nanogram amounts of and/or degraded nucleic acid samples. For example, the methods and compositions disclosed herein are capable of successfully determining the genotype that is, is about, or is more than, 10%, 20%, 30%, 40%, 50%, 60%, 70%, 80%, 90%, 95%, 96%, 97%, 98%, 99%, 100%, or a range between any two of the above values, of the target sequences. In some embodiments, the methods and compositions disclosed herein are capable of successfully determining the genotype of more than about 50%, 80%, 90%, 95%, 98% or more of the target sequences. In some embodiments, the methods and compositions disclosed herein are capable of achieve an intra-locus balance of more than about 10%, 20%, 30%, 40%, 50%, 60%, 70%, 80%, 90%, 95%, 96%, 97%, 98%, 99%, 100%, or a range between any two of the above values, of the target sequences.

For forensic investigation, the plurality of primers may incorporate unique molecule identifiers (UMIs) which aide in removal of, for example, PCR and sequencing errors, stutter and the like from sequencing results. See Kivioja et al., supra. As discussed in further detail elsewhere in this disclosure, inclusion of UMI in the primers also allows the identification of variants within tandem repeat loci, further enhancing the usefulness of the current methods and compositions for DNA profiling and other purposes such as inherence analysis.

Accordingly, in some embodiments, the genotypes of the tandem repeat sequences as disclosed herein may include sequence variants within the tandem repeat loci. Therefore, a homozygote for a tandem repeat (e.g., 13, 13 for D9S1122) using the traditional method may be identified as an isometric heterozygote based on sequence variants within the tandem repeat. As would be appreciated by those skilled in the art, taking into account the intra-locus sequence variants would greatly enhance the usefulness of the methods disclosed herein, for example, for inheritance analysis.

Methods for Constructing a Nucleic Acid Library

Embodiments disclosed herein provide methods of constructing a nucleic acid library comprising: providing a nucleic acid sample, and amplifying the nucleic acid sample with a plurality of primers that specifically hybridize to at least one target sequence comprising a single nucleotide polymorphism (SNP) and at least one target sequence comprising a tandem repeat sequence.

The methods and compositions disclosed herein are designed to be sensitive enough to detect sub-nanogram amounts of nucleic acid molecules. Further, the methods and compositions disclosed herein may be useful to amplify a nucleic acid sample that consists of low-quality nucleic acid molecules, such as degraded and/or fragmented genomic DNA from a forensic sample. The nucleic acid sample may be either purified or a crude DNA containing lysate, for example derived from a buccal swap, paper, fabric or other substrate that may be impregnated with saliva, blood, or other bodily fluids. As such, in some embodiments, the nucleic acid sample may comprise low amount of or fragmented DNA, such as genomic DNA. For example, the nucleic acid sample may comprise an amount of nucleic acid (e.g., genomic DNA) that is, is about, or is less than, 1 pg, 2 pg, 3 pg, 4 pg, 5 pg, 6 pg, 7 pg, 8 pg, 9 pg, 10 pg, 11 pg, 12 pg, 13 pg, 14 pg, 15 pg, 16 pg, 17 pg, 18 pg, 19 pg, 20 pg, 30 pg, 40 pg, 50 pg, 60 pg, 70 pg, 80 pg, 90 pg, 100 pg, 200 pg, 300 pg, 400 pg, 500 pg, 600 pg, 700 pg, 800 pg, 900 pg, 1 ng, 10 ng, 100 ng, or is in a range defined by any two of these values, for example, 10 pg to 100 pg, 10 pg to 1 ng, 100 pg to 1 ng, 1 ng to 10 ng, 10 ng to 100 ng, etc. In some embodiments, the nucleic acid sample may comprise an amount of nucleic acid (e.g., genomic DNA) that is about 100 pg to about 1 ng. In some embodiments, the nucleic acid sample may comprise an amount of nucleic acid (e.g., genomic DNA) that is more than about 62.5 pg. In some embodiments, additional fragmentation steps, such as sonication or endonuclease digestion, are not included.

In some embodiments, methods disclosed herein comprise amplification and library preparation in anticipation of downstream parallel sequencing. An assay may include two PCR mastermixes, two thermostable polymerases, two primer mixes and library adaptors. In some embodiments, a sample of DNA may be amplified for a number of cycles by using a first set of amplification primers that comprise target specific regions and non-target specific tag regions and a first PCR mastermix. The tag region can be any sequence, such as a universal tag region, a capture tag region, an amplification tag region, a sequencing tag region, a UMI tag region, and the like. For example, a tag region can be the template for amplification primers utilized in a second or subsequent round of amplification, for example for library preparation. In some embodiments, the methods comprise adding single stranded-binding protein (SSB) to the first amplification products. An aliquot of the first amplified sample can be removed and amplified a second time using a second set of amplification primers that are specific to the tag region, e.g., a universal tag region or an amplification tag region, of the first amplification primers which may comprise of one or more additional tag sequences, such as sequence tags specific for one or more downstream sequencing workflows, and the same or a second PCR mastermix. As such, a library of the original DNA sample is ready for sequencing.

An alternative method could comprise the first amplification being performed in a small volume (e.g., 15 ul) and instead of transferring an aliquot to a new location for a second round of amplification, additional reagents to perform a second round of amplification could be added to the tube.

Once the library is created, it can be purified and quantitated. In some examples, purification can be performed by processing the sample through a substrate such as AMPURE XP Beads (Beckman Coulter) which serves to purify the DNA fragments away from reaction components. Another method could be the incorporation of a purification moiety, such as a hapten moiety, into the second set of amplification primers. For example, if a biotin was incorporated into one the primers of the second amplification primer set then the library fragments could be capturing using a streptavidin moiety on a bead for example. Utilizing the capture strategy the libraries could also be normalized and quantitated using Bead Based Normalization (BBN). However, libraries can be purified and quantitated, or pooled and quantitated if multiple reactions are being performed, without the use of BBN. For example, libraries could also be quantitated by gel electrophoretic methods, BioAnalyzer, qPCR, spectrophotometric methods, quantitation kits (e.g., PicoGreen, etc.) and the like as known in the art. Following quantitation, the library can then be sequenced by parallel sequencing.

In some embodiments, the first set of amplification primers used to amplify a target DNA is provided in such a limited concentration that when an aliquot of the first amplification reaction is added to a new tube and the reagents from the second amplification reaction are added there is minimal to undetectable carryover amplification resulting from the first set of amplification primers and a cleanup step between the first amplification reaction and the second amplification reaction is not required. In some examples, the concentration of the amplification primers for a first PCR is, is about, or is less than, 0.5 nM, 0.6 nM, 0.7 nM, 0.8 nM, 0.9 nM, 1.0 nM, 1.5 nM, 2.0 nM, 3.0 nM, 4.0 nM, 5.0 nM, 6.0 nM, 7.0 nM, 8.0 nM, 9.0 nm 10.0 nM, 11.0 nM 12.0 nM, or a range between any of these values, for example, 0.5 nM to 1.0 nM, 1.0 nM to 12 nM, 0.8 nM to 1.5 nM, etc. In some embodiments, the concentration of amplification primers for a first PCR is about 0.9 nM to about 10 nM.

Figure 2:
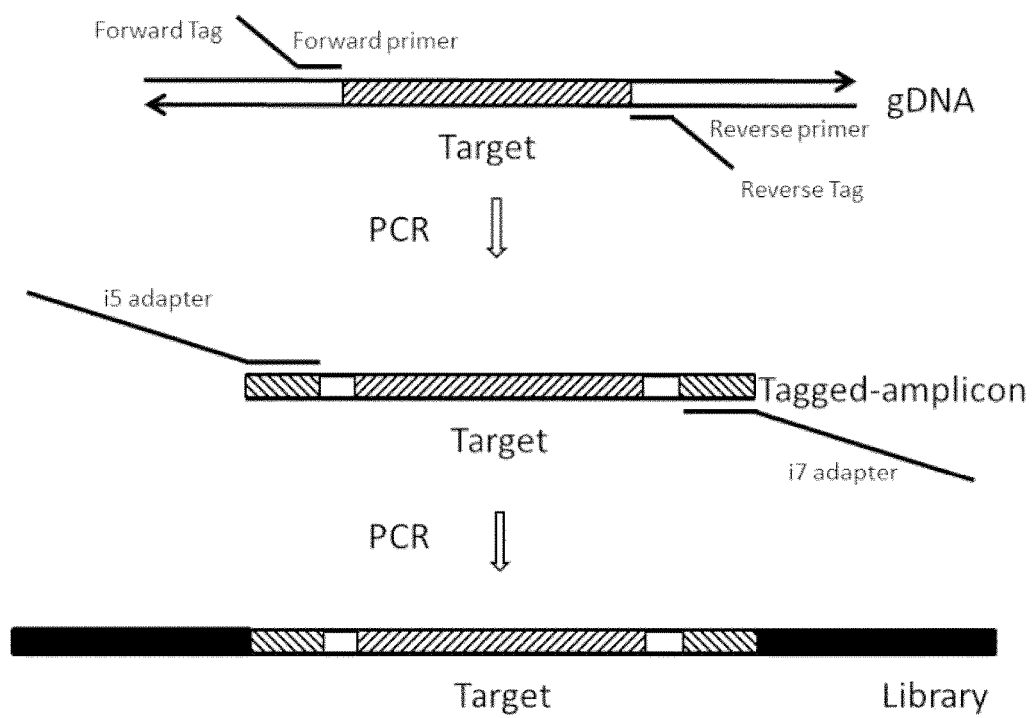
FIG. 2 shows one exemplary embodiment of a method for creating a library useful for DNA profiling.

FIG. 2 shows an exemplary workflow of the presently disclosed methods in one embodiment. A target genomic DNA sequence is amplified using a first set of primers comprising a region that flanks the target sequence and amplification tag regions (which may be the same or different) resulting in amplicons comprising the target sequence and tags on both ends. An aliquot of the amplicons from the first PCR is further amplified using a second set of primers specific to the first tag sequences further comprising sequencing primer sequences (i5 and i7 adapter sequences), thereby generating a library comprising the target DNA sequence flanked by sequences used in parallel sequencing, in this case i5 and i7 sequences are utilized in sequence by synthesis methods popularized by Illumina, Inc.

Figure 3:
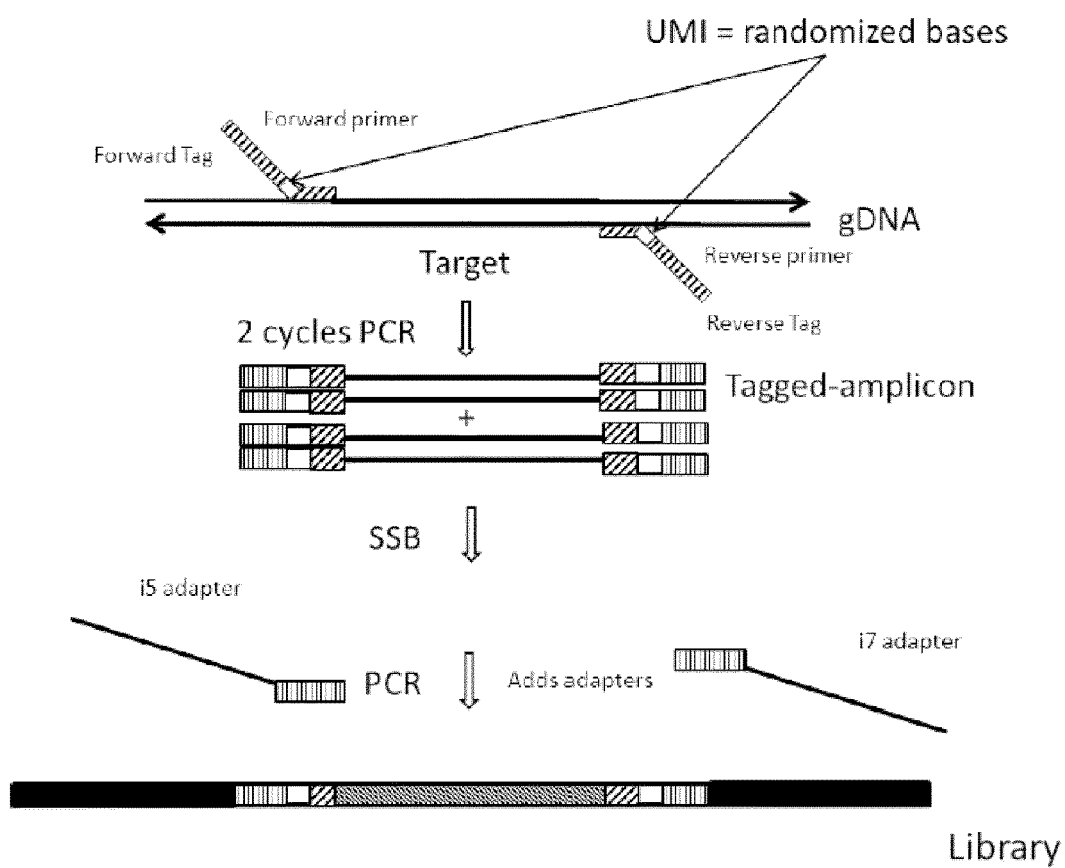
FIG. 3 shows another exemplary embodiment of a method for creating a library useful for DNA profiling.

An example of an alternative workflow for determining a DNA profile from a sample is described in FIG. 3. In this example, a DNA target is amplified with a first primer pair that comprises sequences that flank the target sequence, non-target tag sequences (the same or different) and further unique molecular identifier sequences or UMIs, which comprise randomized bases. The UMIs can be used, for example, to bioinformatically decrease or eliminate errors that occur during the library preparation processes (e.g., PCR artifacts or misincorporations, etc.). Use of UMIs can be important for DNA profiling, but are of particular importance for use in helping to eliminate errors when samples are sequenced for criminal casework. In this example, the first round of amplification is performed for 2 cycles, which is followed by addition of a single stranded binding protein (SSB) and incubation at 37 degree C. for 15 min following by a 95 degree C./5 min inactivation which effectively quenches further amplification of the first set of amplification primers during the second round of amplification. Although the mechanism is unknown, it is contemplated that adding the SSB irreversibly binds the single stranded first amplification primers and prevents them from participating in subsequent amplification reactions. Following SSB incubation, a second set of primers comprising sequence tags and a second PCR mix is added resulting in the sequencing library.

Nucleic Acid Library

Embodiments disclosed herein provide nucleic acid libraries, which may be used for sequencing. In some embodiments, the nucleic acid libraries disclosed herein may comprise a plurality of nucleic acid molecules, wherein the plurality of nucleic acid molecules comprise at least one tandem repeat sequence flanked by a first pair of tag sequences and at least one single nucleotide polymorphism (SNP) sequence flanked by a second pair of tag sequences.

As outlined herein, the size of the nucleic acid molecules may vary greatly using the methods and compositions disclosed herein. It would be appreciated by those skilled in the art that the nucleic acid molecules amplified from a target sequence comprising a tandem repeat (e.g., STR) may have a large size, while the nucleic acid molecules amplified from a target sequence comprising a SNP may have a small size. For example, the nucleic acid molecules may comprise from less than a hundred nucleotides to hundreds or even thousands of nucleotides. Therefore, the size of the nucleic acid molecules may have a range that is between any two values of about 50 bp, about 60 bp, about 70 bp, about 80 bp, about 90 bp, about 100 bp, about 110 bp, about 120 bp, about 130 bp, about 140 bp, about 150 bp, about 200 bp, about 300 bp, about 400 bp, about 500 bp, about 600 bp, about 700 bp, about 800 bp, about 900 bp, about 1 kb, or more. In some embodiments, the minimal size of the nucleic acid molecules may be a length that is, is about, or is less than, 50 bp, 60 bp, 70 bp, 80 bp, 90 bp, or 100 bp. In some embodiments, the maximum size of the nucleic acid molecules may be a length that is, is about, or is more than, 100 bp, 150 bp, 200 bp, 250 bp, 300 bp, 350 bp, 400 bp, 450 bp, 500 bp, or 1 kb.

For cluster generation, the library fragments are immobilized on a substrate, for example a slide, which comprises homologous oligonucleotide sequences for capturing and immobilizing the DNA library fragments. The immobilized DNA library fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized. However, the methods described herein are not limited to any particular sequencing preparation methodology or sequencing platform and can be amenable to other parallel sequencing platform preparation methods and associated sequencing platforms.

Primers

Embodiments disclosed herein provide a plurality of primers that specifically hybridize to at least one short target sequence and at least one long target sequence in a nucleic acid sample, wherein amplifying the nucleic acid sample using the plurality of primers in a single multiplex reaction results in at least one short amplification product and at least one long amplification product, wherein each of the plurality of primers comprises one or more tag sequences. Further disclosed herein is a plurality of primers that have the sequences set forth in Tables 1-2.

For multiplex amplification of large target sequence (e.g., STRs, ITRs) and small target sequence (e.g., SNPs), primers are designed that would allow for balanced amplification across all the target types. The methods and compositions disclosed herein may be used to amplify multiple tandem repeat target sequences in a single multiplex reaction. For example, the plurality of primers may specifically hybridize to a number of tandem repeat sequences that is, is about, or is more than 4, 6, 8, 10, 12, 14, 16, 18, 24, 30, 40, 50, 60, 70, 80, 90, 100, or a range between any of the two values, such as 4 to 12, 10 to 24, 30 to 100, etc. In some embodiments, the plurality of primers may specifically hybridize to at least 24 tandem repeat sequences. In some embodiments, the plurality of primers may specifically hybridize to at least 60 tandem repeat sequences. The methods and compositions disclosed herein may be used to amplify multiple SNP target sequences in a single reaction. For example, the plurality of primers may specifically hybridize to a number of SNP sequences that is, is about, or is more than 4, 6, 8, 10, 12, 14, 16, 18, 24, 30, 40, 50, 60, 70, 80, 90, 100, or a range between any of the two values, such as 4 to 12, 10 to 24, 30 to 100, etc. In some embodiments, the plurality of primers may specifically hybridize to at least 30 SNP sequences. In some embodiments, the plurality of primers may specifically hybridize to at least 50 SNP sequences.

It was discovered during experimentation that the short SNP target sequences preferentially amplified over the longer STR target sequences when using primers that were designing following established criteria and wisdom for successful primer design. Further, at least in the sequence by synthesis workflow where clusters are generated and the clusters are themselves sequenced (for example, when following sequence by synthesis (SBS, disclosed herein elsewhere) associated with the Illumina, Inc. sequencers) preferential cluster amplification of the shorter library SNP fragments also occurred. To overcome these two biases, a new strategy was needed for primer design that would allow for balanced amplification between the short SNP target sequences and the long STR target sequences.

One of the strategies included designing primers for STR amplification. With STRs, the repeated sequences are often embedded within larger repeated regions; therefore designing specific primers for STR amplification can be problematic. Further, STRs and their flanking regions are oftentimes AT rich. In one instance, primers were designed to the problematic regions using a design strategy contrary to conventional and well established PCR design criteria. The established criteria for PCR primer design states that, among other criteria, 1) optimal length for primers is 18-22 nucleotides, 2) the Tm should be in the range of 55-58 degrees C., 3) GC content should be around 40-60%, 4) and repeated AT dinucleotide regions should be avoided, with <4 dinucleotide AT repeats being the maximum. Primers were designed that were longer than typical PCR primers, for example 23-35 nucleotides long instead of 18-22 nucleotides, they had low melting temperatures (Tm), for example around 54 degrees C. instead of around 58 degrees C., and the primers were AT rich, three parameters that conventional established PCR criteria teach should be avoided for optimal primer design. In effect, non-optimal primers were designed. Surprisingly, it was discovered that these long, AT rich, low Tm primers actually multiplexed the STRs better than the short, high Tm low AT containing primers. Without being bound to any theory, it is contemplated that the shorter primers that were designed following established PCR design criteria might form dimers that had high melting temperatures and thus formed dimers efficiently under normal PCR conditions, whereas the longer, low Tm primers might form dimers under really low Tm and thus would not be stable for dimer formation, thereby allowing for increased participation of the longer, low Tm primers under normal amplification conditions compared to the short, high Tm primers (e.g., 18-22 nucleotides, Tm of 60 degrees C., 50% GC content).

The longer, low Tm, AT rich primers for STR amplification were then multiplexed with the conventionally designed, high Tm shorter primers that targeted SNPs. However, the multiplex amplification reactions were once again unsuccessful in providing a balanced amplification of both STRs and SNPs in one multiplex reaction. It was contemplated that perhaps applying the unconventional primer design to amplify non-problematic targets, for example to amplify the SNP targets, might yield successful multiplex amplifications. As such, the same criteria used to design non-optimal primers for STRs were applied to primer design for SNPs (long, low Tm, AT rich). Surprisingly, the new designed primers resulted in better balance between amplification of STRs and SNPs in a multiplex reaction.

Figure 4:
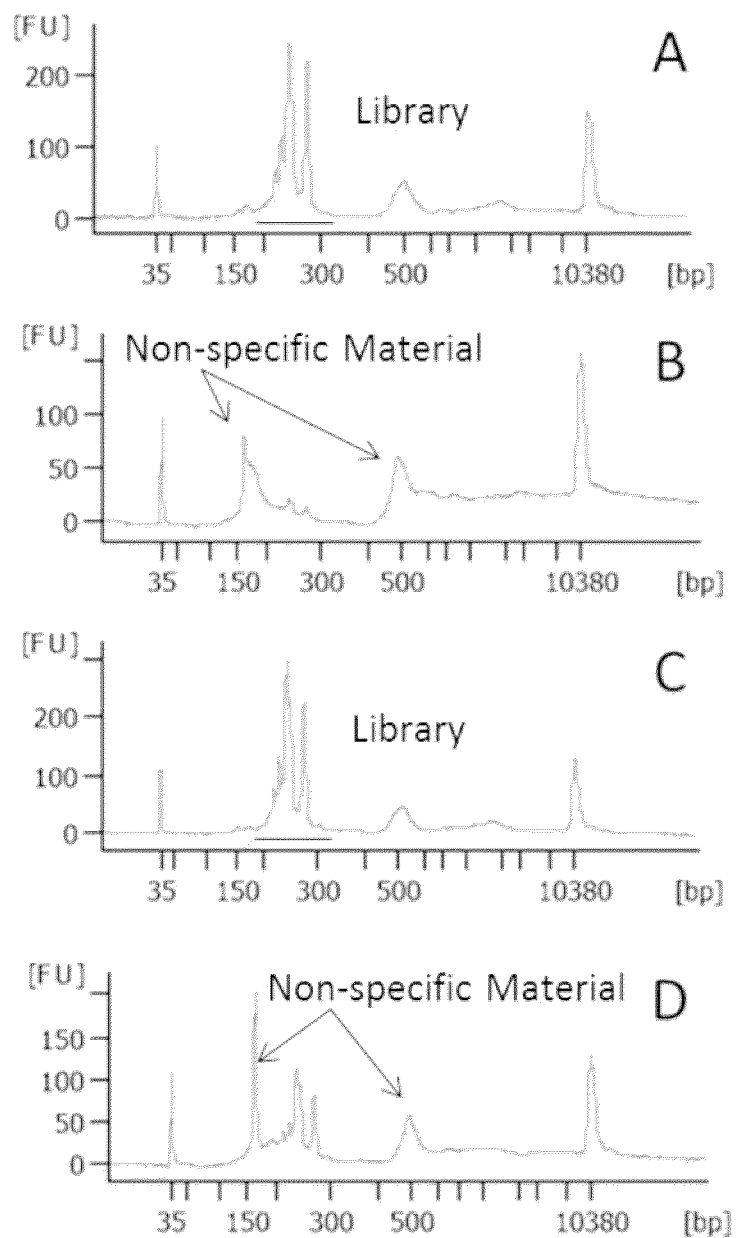
FIG. 4A, FIG. 4B, FIG. 4C and FIG. 4D are line graphs illustrating electropherogram results of how a primer pair designed by traditional methods and following established PCR primer design protocols and limitations can cause non-specific amplification of genomic targets and obscuration of desired amplicons detection when combined with primers designed following methods of the present disclosure; A) 10 primer pairs designed by methods of the present disclosure directed to SNP loci, B) and D) the 10 primers plus an additional primer pair designed by traditional methods demonstrating that the additional primer pair interferes with the 10 primer pairs during amplification, and C) the 10 primer pairs plus an additional primer pair, wherein the additional primer pair was also designed by following the methods of the present disclosure resulting in a successful amplification of all the targeted SNPs. The X-axis is the size of the library fragments (bp) and the Y axis is fluorescence units of (FU) of the amplified peaks of the amplified fragments.

FIG. 4 shows examples of the interplay between the conventional and unconventional designed primers in a multiplex reaction. In FIG. 4A a multiplex reaction of 10 SNP targets shows expected amplification in the desired range of around 200-350 bp for the library. The primers used to amplify the 10 SNPs in the multiplex were designed to be longer, have lower Tm and be more AT rich that is advised by established PCR primer design criteria. When an 11th primer pair is designed using the established PCR design criteria, that is the primers are short, have high Tm and are not AT rich, and added to the 10 pairs the resulting multiplex shows non-specific amplification of the target DNA. As seen in FIGS. 4B and 4D, the addition of an 11th conventionally designed primer pair interferes with the 10 plex of unconventional primer pairs and results in an unsuccessful multiplex amplification of targeted SNPs. However, the addition of an 11th primer pair that is also unconventionally designed following the same criteria as the 10 plex of primer pairs results in the successful amplification of the SNP targets (FIG. 4C).

Accordingly, in some embodiments, each of the plurality of primers has a low melting temperature, e.g., less than 60 degrees C. or about 50 degrees C. to about 60 degrees C., and/or has a length of at least 24 nucleotides, e.g., about 24 nucleotides to about 38 nucleotides. In some embodiments, each of the plurality of primers comprises a homopolymer nucleotide sequence.

In some examples, the unconventionally designed primers comprise sequences that flank the targeted STRs and SNPs and additional non-template sequences. The additional sequences can be, for example tag sequences that serve a purpose during library preparation or sequencing methodologies. For example, a tag sequence can be a capture sequence such as a hapten moiety than can be captured by an immobilized partner moiety for purifying library fragments. An example of a hapten moiety is biotin which can be captured by streptavidin for isolated library fragments from reaction components and the like. A tag sequence could also be an amplification sequence, for example that is complementary to an amplification primer and is used in one or more amplification reactions. FIGS. 2 and 3 show examples of tag sequences that are used in a second round of amplification following a first round of amplification. A tag sequence could also be a sequence tag. FIGS. 2 and 3 also show examples of sequence tags, i5 adapter and i7 adapter are used in sequencing as hybridization, cluster generation and sequencing primers during the sequence by synthesis reactions as described herein. Another example of a tag sequence is a unique molecular identifier, or UMI, as shown in FIG. 3.

A UMI comprises a random stretch of nucleotides that can be used during sequencing to correct for PCR and sequencing errors, thereby adding an additional layer of error correction to sequencing results. UMIs could be from, for example 3-10 nucleotides long, however the number will depend on the amount of input DNA. For example, if ing DNA is used to target around 250 sites, then it is anticipated that approximately 350 copies×250 targets would be needed, so approximately 90,000 different UMIs. If more DNA is utilized, for example 10 ng, then approximately 1 million different UMIs could be needed. All PCR duplicates from the same PCR reaction would have the same UMI sequence, as such the duplicates can be compared and any errors in the sequence such as single base substitutions, deletions, insertions (i.e., stutter in PCR) can be excluded from the sequencing results bioinformatically. Unique molecular identifiers can also be used in analysis for a mixed sample. Mixed samples, for example a female DNA sample that is contaminated with male DNA, can be deconvoluted to report both the female and male DNA contributions using UMI sequences. For example, there could be a total of four different repeated numbers for two mixed DNAs; however there could be less than four if the mixture of two samples shares alleles at a particular locus. These shared alleles can be distinguished and approximate percentages determined using the UMIs for determining the number of different alleles in the initial population of DNA molecules. For example, the initial molecules could be counted and if a minor contributor was present at, for example 5%, then 5% of the UMIs would identify one genotype and 95% would identify a second genotype. After PCR, if one of the alleles (or perhaps more) was biased upon amplification then that 5:95 ratio would not be seen. However, using UMIs a biased ratio could be corrected after PCR duplicates are condensed using UMI detection and correction. This is important when trying to differentiate from a stutter artifact from PCR and a true minor contributor.

A primer of the present methods can comprise one or more tag sequences. The tag sequences can be one or more of primer sequences that are not homologous to the target sequence, but for example can be used as templates for one or more amplification reactions. The tag sequence can be a capture sequence, for example a hapten sequence such as biotin that can be used to purify amplicons away from reaction components. The tag sequences can be sequences such as adaptor sequences that are advantageous for capturing the library amplicons on a substrate for example for bridge amplification in anticipation of sequence by synthesis technologies as described herein. Further, tag sequences can be unique molecular identifier tags of typically between, for example, 3-10 nucleotides comprised of a randomized stretch of nucleotides that can be used for error correction during library preparation and/or sequencing methods.

Additionally, it is advantageous for a multiplexed PCR reaction to contain oligonucleotide primers to substantially all of the targets pooled together into one mix. However, as disclosed herein, the oligonucleotides are uncharacteristically longer than primers designed using traditional parameters. Further addition of tag sequences to the primers, such as the addition of UMIs that append a gene target specific sequence create still longer primer sequences. In some embodiments, glycine betaine (approximately 1.5M) may be added to the plurality of primers. For example, in some embodiments the amplification buffers used in amplification reactions with unconventional primers as disclosed herein comprise a betaine concentration that is, is about, or is more than, 100 mM, 200 mM, 300 mM, 400 mM, 500 mM, 600 mM, 700 mM, 800 mM, 900 mM, 1 M, 1.2 M, 1.3 M, 1.4 M, 1.5 M, 1.6 M, 1.7 M, 1.8 M, 1.9 M, 2 M, 3 M, 4 M, 5 M, 6 M, 7 M, 8 M, 9 M, 10 M, or a range between any two of these values, for example, from 500 mM to 2 M, from 1 M to 1.5 M, etc. As such, a primer mix as described herein supplemented with betaine, for example at approximately 1.5M, would be advantageous when practicing methods of the present disclosure. In some embodiments, glycerol may be added to the plurality of primers. For example, in some embodiments the amplification buffers used in amplification reactions with unconventional primers as disclosed herein comprise a glycerol concentration that is, is about, or is more than, 100 mM, 200 mM, 300 mM, 400 mM, 500 mM, 600 mM, 700 mM, 800 mM, 900 mM, 1 M, 1.2 M, 1.3 M, 1.4 M, 1.5 M, 1.6 M, 1.7 M, 1.8 M, 1.9 M, 2 M, 3 M, 4 M, 5 M, 6 M, 7 M, 8 M, 9 M, 10 M, or a range between any two of these values, for example, from 500 mM to 2 M, from 1 M to 1.5 M, etc. As such, a primer mix as described herein supplemented with glycerol, for example at approximately 1.5M, would be advantageous when practicing methods of the present disclosure.

In some embodiments, buffers associated with unconventional primer design used in amplification methods of the present disclosure may also be modified. For example, in some embodiments the salt concentrations, such as KCl, LiCl, NaCl, or a combination thereof, of the amplification buffer are increased compared to the salt concentration of an amplification buffer used in conjunction with conventionally designed primers. In some embodiments, amplification buffers used in amplification reactions with unconventional primers as disclosed herein comprise a KCl concentration that is, is about, or is more than, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 250 mM, 300 mM, 400 mM, 500 mM, or a range between any two of these values, for example, from 60 mM to 200 mM, from 100 mM to 250 mM, etc. In some embodiments, amplification buffers used in amplification reactions with unconventional primers as disclosed herein comprise a KCl concentration that is about 145 mM. In some embodiments, amplification buffers used in amplification reactions with unconventional primers as disclosed herein comprise a LiCl concentration that is, is about, or is more than, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 250 mM, 300 mM, 400 mM, 500 mM, or a range between any two of these values, for example, from 60 mM to 200 mM, from 100 mM to 250 mM, etc. In some embodiments, amplification buffers used in amplification reactions with unconventional primers as disclosed herein comprise a LiCl concentration that is about 145 mM. In some embodiments, amplification buffers used in amplification reactions with unconventional primers as disclosed herein comprise a NaCl concentration that is, is about, or is more than, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 250 mM, 300 mM, 400 mM, 500 mM, or a range between any two of these values, for example, from 60 mM to 200 mM, from 100 mM to 250 mM, etc. In some embodiments, amplification buffers used in amplification reactions with unconventional primers as disclosed herein comprise a NaCl concentration that is about 145 mM.

In some embodiments, amplification buffers used in amplification reactions with unconventional primers as disclosed herein may comprise $MgSO_4$, $MgCl_2$, or a combination thereof.

Kits

Embodiments disclosed herein provide kits comprising at least one container means, wherein the at least one container means comprises a plurality of primers as disclosed herein. In some embodiments, the container means may be a tube, a well, a microtiter plate, etc. In some embodiments, the plurality of primers may specifically hybridize to a number of tandem repeat sequences that is, is about, or is more than 4, 6, 8, 10, 12, 14, 16, 18, 24, 30, 40, 50, 60, 70, 80, 90, 100, or a range between any of the two values, such as 4 to 12, 10 to 24, 30 to 100, etc. In some embodiments, the plurality of primers may specifically hybridize to at least 24 tandem repeat sequences. In some embodiments, the plurality of primers may specifically hybridize to at least 60 tandem repeat sequences. The methods and compositions disclosed herein may be used to amplify multiple SNP target sequences in a single reaction. For example, the plurality of primers may specifically hybridize to a number of SNP sequences that is, is about, or is more than 4, 6, 8, 10, 12, 14, 16, 18, 24, 30, 40, 50, 60, 70, 80, 90, 100, or a range between any of the two values, such as 4 to 12, 10 to 24, 30 to 100, etc. In some embodiments, the plurality of primers may specifically hybridize to at least 30 SNP sequences. In some embodiments, the plurality of primers may specifically hybridize to at least 50 SNP sequences.

In some embodiments, the at least one container means comprises an amplification buffer. In some embodiments, buffers associated with unconventional primer design used in amplification methods of the present disclosure may also be modified. For example, in some embodiments the salt concentrations, such as KCl, LiCl, NaCl, or a combination thereof, of the amplification buffer are increased compared to the salt concentration of an amplification buffer used in conjunction with conventionally designed primers. In some embodiments, amplification buffers used in amplification reactions with unconventional primers as disclosed herein comprise a KCl, NaCl or LiCl concentration that is, is about, or is more than, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 250 mM, 300 mM, 400 mM, 500 mM, or a range between any two of these values, for example, from 60 mM to 200 mM, from 100 mM to 250 mM, etc. In some embodiments, amplification buffers used in amplification reactions with unconventional primers as disclosed herein comprise a KCl, NaCl or LiCl concentration that is about 145 mM.

In some embodiments, amplification buffers used in amplification reactions with unconventional primers as disclosed herein may comprise $MgSO_4$, $MgCl_2$, or a combination thereof.

Sequencing Methods

The present methods are not limited to any particular sequencing platform, however are being exemplified here in regards to SBS, or sequence by synthesis, type of parallel sequencing. Particularly applicable techniques are those wherein nucleic acids are attached at fixed locations in an array such that their relative positions do not change and wherein the array is repeatedly imaged. Examples in which images are obtained in different color channels, for example, coinciding with different labels used to distinguish one nucleotide base type from another are particularly applicable.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In some examples where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Some examples include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another example of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides. Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some examples can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some examples can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some examples can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some examples can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods of the present disclosure utilize the Illumina, Inc. technology for sequencing the DNA profile libraries created by practicing the methods described herein. The MiSeq sequencing instrument was used for clustering and sequencing for the examples described herein. However, as previously stated and as understood by a skilled artisan, the present methods are not limited by the type of sequencing platform used.

EXAMPLES

The following examples disclose several methods and materials for DNA profiling. These methods and materials can be modified while maintaining the spirit and scope of the invention. Such modifications will become apparent to those skilled in the art from a consideration of this disclosure or practice of the methods disclosed here. Consequently, it is not intended that these methods or materials be limited to the specific examples disclosed herein, but that it cover all modifications and alternatives that fall within the scope and spirit of the present disclosure.

Example 1—Unconventional Primer Design

The computer design program DesignStudio from Illumina, Inc. (San Diego, Calif.) was modified and used for primer design. A skilled artisan would of course understand that alternative primer design programs such as Primer3 can also be used and the default parameters reset to mimic the intent of the modified parameters for primer design. The settings are typically reset in the config.xml file that comes with the software, however this may differ when using different software and consulting the specific materials for accessing default parameters for each software is typical practice. The following parameters can be reset in the primer design software:

1) The desired minimum length amplicon reset to >60<
2) The desired maximum length amplicon reset to >120<
3) The tight candidate spacing reset to >3<(default is 30 bp)
4) The % GC Max probe reset to >60< to allow for increased number of AT rich repeat stretches
5) The mean Tm reset to >57<(default 59 C) to lower the mean Tm
6) The maximum Tm reset to >60<(default 71)
7) The minimum Tm reset to >51<(default 55)
8) The mean probe length reset to >28<(default 27)
9) The maximum probe length reset to >38<(default 30)
10) The minimum probe length reset to >25<(default 22)

For designing the SNP primers, the range to target for the 3' end of the primer was set to "small" to keep the primers around 1bp away for the targeted SNP. Once all the parameters are reset, the primer design program can be run on the sequence to determine the primer pair candidates that fall under the new parameters. For example, a user of the software can generate a targets list that tells the software where to look in the genome for designing the primers. In the present example, the targeted regions were copy and pasted into the graphic user interface application which the DesignStudio software used to orient and target primer design. Once the targeted regions were input into the program, the program directed to Create a Design File to start the tool and create the primer designs. In the present example, the main output was a .txt file that included the primer sequences and/or some of the regions contained failures and were "undesignable", at which point the targeted sequences needed to be redefined and rerun. The software used in this experiment provided the designed primers that were mapped onto the sequence that was specified as the targeted region. Following the reset parameters, primers were designed that did not follow the conventional criteria for primer design for amplification; however which allowed for the multiplex amplification of long STRs and short SNPs.

Examples of designed STR targeted primers advantageous in methods disclosed herein include those listed in Table 1. Examples of SNP targeted primers advantageous in methods disclosed herein include those listed in Table 2.

TABLE 1

| | STR targeted primer without tags and amplicon sizes | | |
|---|---|---|---|
| SEQ ID NO | STR LOCUS PRIMER | EXAMPLES OF STR PRIMERS WITHOUT TAGS | AMPLICON SIZE |
| 1 | AmeIPP_F_T | CCCTGGGCTCTGTAAAGAA | 106, 112 |
| 2 | AmeIPP_R_Sm | ATCAGAGCTTAAACTGGGAAGCTG | |
| 3 | CSF1PO_F1_T | ACAGTAACTGCCTTCATAGATAG | 117 |
| 4 | CSF1PO_R1_Sm | GTGTCAGACCCTGTTCTAAGTA | |
| 5 | D5S818_F2_T | TGATTTTCCTCTTTGGTATCCTTATGTAAT | 112 |
| 6 | D5S818_R2_Sm | ACAACATTTGTATCTTTATCTGTATCCT | |
| 7 | D8S1179_F1_T | TTTGTATTTCATGTGTACATTCGTATC | 110 |
| 8 | D8S1179_R1_Sm | ACCTATCCTGTAGATTATTTTCACTGTG | |

TABLE 1-continued

STR targeted primer without tags and amplicon sizes

| SEQ ID NO | STR LOCUS PRIMER | EXAMPLES OF STR PRIMERS WITHOUT TAGS | AMPLICON SIZE |
|---|---|---|---|
| 9 | D18S51_F1_T | CTCTGAGTGACAAATTGAGACCTT | 184 |
| 10 | D18S51_R1_T | TTAACTTCTCTGGTGTGTGGAGATG | |
| 11 | D19S433_F1_T | TTTGGTGCACCCATTACCCG | 188 |
| 12 | D19S433_R1_Sm | AGGAGGTTGAGGCTGCAAAA | |
| 13 | D7S820_F2_T | CACCAAATATTGGTAATTAAATGTTTACTATAGAC | 167 |
| 14 | D7S820_R2_Sm | TAAAGGGTATGATAGAACACTTGTC | |
| 15 | D16S539_F2_T | CAAAGGCAGATCCCAAGCTCT | 160 |
| 16 | D16S539_R2_Sm | TGTGTGTGCATCTGTAAGCAT | |
| 17 | D3S1358_F2_T | TGGTGTGTATTCCCTGTGCC | 170 |
| 18 | D3S1358_R2_Sm | GCAGTCCAATCTGGGTGACA | |
| 19 | D10S1248_F1_T | CCAATCTGGTCACAAACATATTAATGAA | 148 |
| 20 | D10S1248_R1_Sm | TTTCCCTTGTCTTGTTATTAAAGGAAC | |
| 21 | TH01_F1_T | TTCCCATTGGCCTGTTCCTC | 112 |
| 22 | TH01_R1_Sm | CTGTACACAGGGCTTCCGAG | |
| 23 | FGA_F2_T | GCTGAGTGATTTGTCTGTAATTG | 188 |
| 24 | FGA_R2_Sm | GAACTCACAGATTAAACTGTAACCAAAATAAAATTAG | |
| 25 | D6S1043_F1_T | CAATAGTGTGCAAGGATGGGTG | 175 |
| 26 | D6S1043_R1_Sm | TCTGTGGTTCTCCAGCTTAC | |
| 27 | TPOX_F1_T | CTTAGGGAACCCTCACTGAATG | 77 |
| 28 | TPOX_R1_Sm | GTCCTTGTCAGCGTTTATTTGC | |
| 29 | D13S317_F2_T | TTGGGTTGAGCCATAGGCAG | 162 |
| 30 | D13S317_R2_Sm | GCATCCGTGACTCTCTGGAC | |
| 31 | D21S11_F1_T | GTTATGGGACTTTTCTCAGTCTCCAT | 226 |
| 32 | D21S11_R3_Sm | GAGACTAATAGGAGGTAGATAGACTGG | |
| 33 | D12S391_F1_T | GAGACTGTATTAGTAAGGCTTCTC | 253 |
| 34 | D12S391_R2_Sm | CCTGGACTGAGCCATGCTCC | |
| 35 | D1S1656_F2_T | CAGTCCTGTGTTAGTCAGGATTC | 173 |
| 36 | D1S1656_R1_Sm | TCAAGGGTCAACTGTGTGATGT | |
| 37 | D9S1122_F3_T | CTTCTGAAAGCTTCTAGTTTACCT | 120 |
| 38 | D9S1122_R2_Sm | TTGCTTATTTGTGGGGTATTTCA | |
| 39 | PentaE_F1_T | AAGAATTCTCTTATTTGGGTTATTAATTG | 362 |
| 40 | PentaE_R1_Sm | AAATTGTGGACAGGTGCGGT | |
| 41 | D17S1301_F2_T | CCATGTAAAAATACATGCATGTGTTTATTTATAC | 142 |
| 42 | D17S1301_R2_Sm | TGATTAAAAAGAATGAAGGTAAAAATGTGTATAAC | |
| 43 | D2S441_F2_T | CCAAATGTTTATGATTAATCTTTTAAATTGGAGC | 160 |
| 44 | D2S441_R3_Sm | GTAACAAGGGCTACAGGAATCATGAG | |
| 45 | D4S2408_F3_T | TCATCCACTGAAATGACTGAAAAATAG | 102 |

TABLE 1-continued

STR targeted primer without tags and amplicon sizes

| SEQ ID NO | STR LOCUS PRIMER | EXAMPLES OF STR PRIMERS WITHOUT TAGS | AMPLICON SIZE |
|---|---|---|---|
| 46 | D4S2408_R9_Sm | AGGTACATAACAGTTCAATAGAAAG | |
| 47 | D2S1338_F2_T | GAGTTATTCAGTAAGTTAAAGGATTGCAG | 162 |
| 48 | D2S1338_R2_Sm | GGGAGCCAGTGGATTTGGAAACAG | |
| 49 | PentaD_F3_T | GCATGGTGAGGCTGAAGTAG | 268 |
| 50 | PentaD_R1_Sm | CTAACCTATGGTCATAACGATTTTT | |
| 51 | vWA_F3_T | GATGATAAGAATAATCAGTATGTGACTTGG | 160 |
| 52 | vWA_R3_Sm | ATAGGTTAGATAGAGATAGGACAGATGATA | |
| 53 | SE33_F1_T | CCCTACCGCTATAGTAACTTGC | 380 |
| 54 | SE33_R2_Sm | CACGTCTGTAATTCCAGCTCCTA | |
| 55 | D20S482_F3_T | GGAAGCGTGTACTAGAGTTCTTCAG | 145 |
| 56 | D20S482_R2_Sm | GGACAGCCTCCATATCCACATG | |
| 57 | DXS10074_F1_T | TTCCTACTGCCCCACCTTTATTG | 212 |
| 58 | DXS10074_R1_sm | TTTATGGTCTCAGTGCCCCTCAGA | |
| 59 | DXS10103_F1_sm | TCATAATCACATATCACATGAGC | 177 |
| 60 | DXS10103_R1_T | AAACAGAACCAGGGGAATGAA | |
| 61 | DXS10135_F1_T | TGAAACTAAAGTCAAATGGGGCTAC | 268 |
| 62 | DXS10135_R1_sm | TAAGGGGTGACACCTCTCTGGATA | |
| 63 | DXS8377_F2_sm | CCCAGCCTACATCTACCACTTCATG | 276 |
| 64 | DXS8377_R2_T | CTAATGTTCGTATGGACCTTTGGAAAGC | |
| 65 | DXS7423_F1_sm | GTCTCCAGTACCCAGCTAGCTTAG | 191 |
| 66 | DXS7423_R1_T | TCTCCCAACCTGCCCTTTATCA | |
| 67 | DXS8378_F1_sm | TTTGGGCTGACACAGTGGCT | 442 |
| 68 | DXS8378_R1_T | TTGATCAACACAGGAGGTTTGACC | |
| 69 | HPRTB_F1_sm | TATACCACTTTGATGTTGACACTAGTTTAC | 213 |
| 70 | HPRTB_R1_T | CCTGTCTATGGTCTCGATTCAAT | |
| 71 | DXS10148_F3_sm | TGCATGACAGAGGGAGATTCT | 256 |
| 72 | DXS10148_R3_T | AGAGGGGAAATAGTAGAATGAGGATG | |
| 73 | DXS7132_F3_sm | GCCAAACTCTATTAGTCAACGTTC | 204 |
| 74 | DXS7132_R4_T | CTGGTTCTCTAGCTCACATACAGT | |
| 75 | DYF387S1ab_F2_T | TTTACCCCTAACAAGAAAAAAGAAGAA | 227, 231 |
| 76 | DYF387S1ab_R2_Sm | CAGTGTGAGAAGTGTGAGAAGTGC | |
| 77 | DYS385a_b_F1_T | GACACCATGCCAAACAACAAC | 260, 248 |
| 78 | DYS385a_b_R1_Sm | ATCTATCTATTCCAATTACATAGTCC | |
| 79 | DYS389I_II_F3_T | TCATTATACCTACTTCTGTATCCAACTCTC | 183, 303 |
| 80 | DYS389I_II_R3_Sm | GGAACACAATTATCCCTGAGTAGCAG | |
| 81 | DYS390_F2_T | GGTAGCATAATAGAAATTTATGAGTGGG | 318 |
| 82 | DYS390_R2_Sm | GAAGACAGACTTCAATATCACAGAACATCG | |

TABLE 1-continued

STR targeted primer without tags and amplicon sizes

| SEQ ID NO | STR LOCUS PRIMER | EXAMPLES OF STR PRIMERS WITHOUT TAGS | AMPLICON SIZE |
|---|---|---|---|
| 83 | DYS391_F1_T | GTGTATCTATTCATTCAATCATACACCC | 143 |
| 84 | DYS391_R1_Sm | CTCCCTGGTTGCAAGCAATTGCC | |
| 85 | DYS438_F1_T | CCAAAATTAGTGGGGAATAGTTGAAC | 149 |
| 86 | DYS438_R2_Sm | GTCGAGATCACACCATTGCATTTC | |
| 87 | DYS439_F1_T | GCCTGGCTTGGAATTCTTTTACCC | 195 |
| 88 | DYS439_R1_Sm | TTTAAGTCTTTAATCTATCTTGAATTAATAGATTC | |
| 89 | DYS481_F1_T | CTTTAAGAGGAGTCTGCTAAAAGGAATG | 144 |
| 90 | DYS481_R3_Sm | TCACCAGAAGGTTGCAAGAC | |
| 91 | DYS505_F1_T | TCTGGCGAAGTAACCCAAAC | 174 |
| 92 | DYS505_R1_Sm | TCGAGTCAGTTCACCAGAAGG | |
| 93 | DYS522_F2_T | GGAACCAGTGAGAGCCG | 306 |
| 94 | DYS522_R2_Sm | CTCAGAGTGCTGAACCCAG | |
| 95 | DYS533_F2_T | GTATTTATTCATGATCAGTTCTTAACTCAACC | 206 |
| 96 | DYS533_R2_Sm | CTACCTAATATTTATCTATATCATTCTAATTATGTCTCTTC | |
| 97 | DYS549_F1_T | CTCTAAAGGTTTTTTTGGTGGCATAAG | 222 |
| 98 | DYS549_R1_Sm | GATTAATACAACAAAAATTTGGTAATCTGAAA | |
| 99 | DYS570_F1_T | CAACCTAAGCTGAAATGCAGATATTC | 170 |
| 100 | DYS570_R1_Sm | GTTATGAAACGTAAAATGAATGATGACTAG | |
| 101 | DYS576_F2_T | GCAGTCTCATTTCCTGGAGATGAAGG | 191 |
| 102 | DYS576_R1_Sm | CTTGGGCTGAGGAGTTCAATC | |
| 103 | DYS612_F2_T | GCCAGTAAGAATAAAATTACAGCATGAAG | 287 |
| 104 | DYS612_R2_Sm | GAATAATCTACCAGCAACAATGGCT | |
| 105 | DYS635_F4_T | TGCCCAATGGAATGCTCTCT | 274 |
| 106 | DYS635_R2_Sm | GCTCCATCTCAAACAACAAAAACACAAAAATG | |
| 107 | DYS643_F2_T | GGGTCATTGAACCTCATGCTCTG | 170 |
| 108 | DYS643_R1_Sm | CCCCCCAAAATTCTACTGAAGTAAA | |
| 109 | Y_GATAH4_F2_T | TAACAGGATAAATCACCTATCTATGTAT | 175 |
| 110 | Y_GATAH4_R2_Sm | GCTGAGGAGAATTTCCAAATTTA | |

TABLE 2

SNP targeted primers

| SEQ ID NO | SNP PRIMER | EXAMPLES OF SNP PRIMERS WITHOUT TAGS |
|---|---|---|
| 111 | rs10092491_iSNPI_T_F2 | CCCGCAAACTAACTAGGATAAATCTCTA |
| 112 | rs1015250_iSNPI_T_F | CGACATGGGAAATGTCAGATCATAAGAC |
| 113 | rs1024116_iSNPI_T_F2 | CCAGGGAGTGAAAAATCCTTTTATCATC |
| 114 | rs1028528_iSNPI_T_F2 | GAGGATGAAGGTTAGAGCCAGACCT |

TABLE 2-continued

SNP targeted primers

| SEQ ID NO | SNP PRIMER | EXAMPLES OF SNP PRIMERS WITHOUT TAGS |
|---|---|---|
| 115 | rs1029047_iSNPI_T_F2 | TGTGGAATAAACTGAAGGCTAAAGAAAA |
| 116 | rs1031825_iSNPI_T_F2 | CAAGCCCTATGCCAAGGATATAACAATG |
| 117 | rs10488710_iSNPI_T_F | GAGGTTTTACTGTATTAGGAGTTCCCAC |
| 118 | rs10495407_iSNPI_T_F | CAGATGTGAGATGATAATTTCGTTCTCC |
| 119 | rs1058083_iSNPI_T_F | TTGTTCTTCTCCATCCCATTTCACCC |
| 120 | rs10773760_iSNPI_T_F | CTTGTACATTCCCTTATCTGCTATGTGG |
| 121 | rs1294331_iSNPI_T_F2 | CTCTCTTTGGAGTTTTATGTGTTGCTAC |
| 122 | rs12997453_iSNPI_T_F | CTCTGATGATGTGCAAGAAAGGTAGGTA |
| 123 | rs13182883_iSNPI_T_F | TCAGACTATGTTTTAAGGAGACTATGAGG |
| 124 | rs13218440_iSNPI_T_F | CTAAGTATCTACCAATGTGCTACGTACC |
| 125 | rs1335873_iSNPI_T_F | CACGTGGATGATATGGTTTCTCAAGG |
| 126 | rs1336071_iSNPI_T_F2 | AGCACCTATATATTATACCTGAAAGCAT |
| 127 | rs1355366_iSNPI_T_F | CCCATGATTTTCTTGTGGTGAGAATTTC |
| 128 | rs1357617_iSNPI_T_F | CACCCTCTGTACTTTAATTTGACTTCCC |
| 129 | rs1382387_iSNPI_T_F | GTTTTTCTTCATTCCCATGTTGTGTAC |
| 130 | rs1413212_iSNPI_T_F | CACTCTTCTGAATCCTGGTCAACAAC |
| 131 | rs1454361_iSNPI_T_F | CAAGTTATATCATAGAGTCTACGACCCC |
| 132 | rs1463729_iSNPI_T_F | CTGCAACTATCAGTCTCTGCCCTTATTC |
| 133 | rs1493232_iSNPI_T_F | GATGTGTCTCAAACTGTTTATTGTGAGG |
| 134 | rs1498553_iSNPI_T_F | GAACTCATTTATCCAGAGACCTGTTCTC |
| 135 | rs1523537_iSNPI_T_F | CATAATACAACCTGTCTTTGGAGTTACT |
| 136 | rs1528460_iSNPI_T_F | GTGACCAGTAGTTCTATGAGCAAGTATG |
| 137 | rs159606_iSNPI_T_F | CCACATTGTATGGTTTTTAGGCACCATG |
| 138 | rs1736442_iSNPI_T_F | CTAATAAGTGGGACAGTTAAGAGAAGGC |
| 139 | rs1821380_iSNPI_T_F | CAAGACAAGCGATTGAAAGAAGTGGAT |
| 140 | rs1886510_iSNPI_T_F | CCTTGTCAATCTTTCTACCAGAGGGTAA |
| 141 | rs1979255_iSNPI_T_F | GAATCATAGCTTGTGTTGGTCAGGG |
| 142 | rs2016276_iSNPI_T_F | GAATTACAAGTATTTGCATCCCAGCCT |
| 143 | rs2040411_iSNPI_T_F | GACCAACTTGGCTTTAACAGATGCAAAT |
| 144 | rs2046361_iSNPI_T_F2 | TCCTTACCTTTAAGACTTTTCCTATTTG |
| 145 | rs2056277_iSNPI_T_F2 | CATTATCTCGTCATACTTCCCTGTCTTG |
| 146 | rs2076848_iSNPI_T_F | GCATCAAATTCACCAGTGAAATTATTGA |
| 147 | rs2107612_iSNPI_T_F | ATGAGTACATTATTCAACTGTTTTGGAG |
| 148 | rs2111980_iSNPI_T_F | CAGCCATGTTGTAAACATTTTTACGGTC |
| 149 | rs214955_iSNPI_T_F | GCACATTCTAAGAACTGGTGATTCTATC |
| 150 | rs221956_iSNPI_T_F | GCTAGAAAAGCTGAGATAGCTGTGAAG |
| 151 | rs2342747_iSNPI_T_F | CCTTGAAGCTCATTCTTTGTTGTCCC |

TABLE 2-continued

SNP targeted primers

| SEQ ID NO | SNP PRIMER | EXAMPLES OF SNP PRIMERS WITHOUT TAGS |
|---|---|---|
| 152 | rs2399332_iSNPI_T_F | CTGGACACCAGACCAAAAACAAATAACC |
| 153 | rs251934_iSNPI_T_F | GTAATTAGAGGGCAGTGAGGCTTTTAA |
| 154 | rs279844_iSNPI_T_F | CTCCAGAAGCTACTGGGATATTAATTAG |
| 155 | rs2830795_iSNPI_T_F | TGAGCCAAATCAGCAATATAATAGGACT |
| 156 | rs2831700_iSNPI_T_F | CCTAGAACCACAATTATCTGTCTTTGGC |
| 157 | rs2920816_iSNPI_T_F2 | CCATTGATTCTCTACAGTTCTGCAGGTA |
| 158 | rs321198_iSNPI_T_F | CTCCACACTTTATACAGGTGAAATCTGA |
| 159 | rs338882_iSNPI_T_F | CATTTTTCTCTCCTTCTGTCTCACCTTC |
| 160 | rs354439_iSNPI_T_F | GCTTCTCTTTCCCTTATGTATCTCTCTC |
| 161 | rs3780962_iSNPI_T_F | GGCTTTTGAAGAAAAACACTAACCTGTC |
| 162 | rs430046_iSNPI_T_F | CACCTATGGGCTCTTCTTATTTCTCC |
| 163 | rs4364205_iSNPI_T_F | CATTTGATAGCCATTTGGGTTGTTTCCA |
| 164 | rs445251_iSNPI_T_F | CCATCACACTATCCTGACATGAACAAAT |
| 165 | rs4606077_iSNPI_T_F | GAAGATTTGCATCCCAGTGAAAGCAC |
| 166 | rs560681_iSNPI_T_F | GCACTTCATAAAGAATCAGTCAGGATGC |
| 167 | rs6444724_iSNPI_T_F | GGAGAATCAGGAAATAGTCACTTCCTAC |
| 168 | rs6811238_iSNPI_T_F | CATTTGACCTTCTAGCCAAATGAAGTAC |
| 169 | rs7041158_iSNPI_T_F | GGAATTTCTGAGAATAACATTGCCTCTC |
| 170 | rs717302_iSNPI_T_F | CATATGTTGGGGGAGCTAAACCTAATGA |
| 171 | rs719366_iSNPI_T_F | CACTGTGACCACAGCATCTTTTAACTC |
| 172 | rs722098_iSNPI_T_F2 | GGGTAAAGAAATATTCAGCACATCCAAA |
| 173 | rs722290_iSNPI_T_F | GAGTATCCCTTATCTAAAATGCTGGTCC |
| 174 | rs727811_iSNPI_T_F | CTTTTTCTCTTACCGGAACTTCAACGAC |
| 175 | rs729172_iSNPI_T_F | CCTCATTAATATGACCAAGGCTCCTCTG |
| 176 | rs733164_iSNPI_T_F | TGACTCTAATTGGGGATGTGGTAATTAG |
| 177 | rs735155_iSNPI_T_F | GACCTAACCTGGAGAAAACCGGAGA |
| 178 | rs740598_iSNPI_T_F | GTTTCTCTTCTCTGAACCTTTGTCTCAG |
| 179 | rs740910_iSNPI_T_F | GCAAACACACAAAGATAGGTTCGAGTTT |
| 180 | rs763869_iSNPI_T_F | CATATCAAGTGCTTTCTGTTGACATTTG |
| 181 | rs8037429_iSNPI_T_F | CTGAAAAGTGCTACGTAAGAGGTCATTG |
| 182 | rs8078417_iSNPI_T_F | CATCTGAGTGTGAGAAGAGCCTCAA |
| 183 | rs826472_iSNPI_T_F2 | CCCAGCAAAAACTTCTTTTCTCCAGTAA |
| 184 | rs873196_iSNPI_T_F | GCTAGGAAAGTTTTCTCTCTGGTTCACA |
| 185 | rs876724_iSNPI_T_F | GAATATCTATGAGCAGGCAGTTAGCAG |
| 186 | rs891700_iSNPI_T_F2 | CTAATCAGTGTCACTATGTGTGAGCTAT |
| 187 | rs901398_iSNPI_T_F | CATCATACAGACTCAAGGAGCTTAGCTG |
| 188 | rs907100_iSNPI_T_F | CTTTCCAAGCCTTGGAAAACACAGAAAA |

TABLE 2-continued

SNP targeted primers

| SEQ ID NO | SNP PRIMER | EXAMPLES OF SNP PRIMERS WITHOUT TAGS |
|---|---|---|
| 189 | rs914165_iSNPI_T_F | GTACCTTATAAATCACGGAGTGCAGAC |
| 190 | rs917118_iSNPI_T_F | CAAGTGGTAAGAGATGACTGAGGTCAA |
| 191 | rs938283_iSNPI_T_F | CTTCTTCTCTTAGAAGGACACTGGTCAG |
| 192 | rs964681_iSNPI_T_F | GTTATGGAGGATTGGTAAGAACCAGAG |
| 193 | rs987640_iSNPI_T_F | GAGCTGTTTAAGGGTAAAGGGGTAGTTA |
| 194 | rs9905977_iSNPI_T_F | GCAGACAAAACCATGACAATGATCTTAG |
| 195 | rs993934_iSNPI_T_F | CCCATGATGAAACAGTTTGCACTAAATG |
| 196 | rs9951171_iSNPI_T_F | CTCAATTTTCTTGTCCCTGCTTTCATG |
| 197 | rs10092491_iSNPI_S_R2 | TTAGAAATTCCAGATAGAGCTAAAACTG |
| 198 | rs1015250_iSNPI_S_R | GTTAGGAAAAGAACCCAGGTGTTTT |
| 199 | rs1024116_iSNPI_S_R2 | GCAAAAGTAAATACAAAGGCATACTTT |
| 200 | rs1028528_iSNPI_S_R2 | CAATGCAAAAGAAAGGTCCTTACTCGAC |
| 201 | rs1029047_iSNPI_S_R2 | CATTTCTAAACTCTAAAACAAACATTTG |
| 202 | rs1031825_iSNPI_S_R2 | GGTCCTTAACCTATTAAATTTTAATGAG |
| 203 | rs10488710_iSNPI_S_R | GACTTTCAATTTATGTCAGCATTTAAAA |
| 204 | rs10495407_iSNPI_S_R | CCTCTTGGTTGCATTGGATTCTCATTG |
| 205 | rs1058083_iSNPI_S_R | TCTCCATGAAACTTGGGTTAATTTTGC |
| 206 | rs10773760_iSNPI_S_R | TGTCTGGAAGTTCGTCAAATTGCAG |
| 207 | rs1294331_iSNPI_S_R2 | GTAGCATAAAACATTCCAAAAATTCAAT |
| 208 | rs12997453_iSNPI_S_R | TGCTTTAAAGATACAGGTTATCTGTATTAC |
| 209 | rs13182883_iSNPI_S_R | CTCTCCGTTACTTTCTTCCTGCCTTT |
| 210 | rs13218440_iSNPI_S_R | GATCCTGAGATTCACCTCTAGTCCCT |
| 211 | rs1335873_iSNPI_S_R | CCGTACCAGGTACCTAGCTATGTACT |
| 212 | rs1336071_iSNPI_SR_2 | CTTTCTGTTTTGTCCATCTGAAATTCT |
| 213 | rs1355366_iSNPI_S_R | CAAAGTTAAGTATCACCATCCAGCTGG |
| 214 | rs1357617_iSNPI_S_R | ATAGGGATAGCTGATAAGAAACATGACC |
| 215 | rs1382387_iSNPI_S_R | CTTAATAAGACGCTGCATCTGCCCA |
| 216 | rs1413212_iSNPI_S_R | TCCAGGAGACATTTGTTCATATAAGTGA |
| 217 | rs1454361_iSNPI_S_R | AGACACTTTTCAGTATCCATTTAGAAAC |
| 218 | rs1463729_iSNPI_S_R | GTTTCACATGTGCATGCTTTTGGGT |
| 219 | rs1493232_iSNPI_S_R | CCAAAGCTATTCTCTCTTTTGGGTGC |
| 220 | rs1498553_iSNPI_S_R | GAAAGTTCACTTCAGATGTTCAAAGCC |
| 221 | rs1523537_iSNPI_S_R | GGGTTTCAGTCTGCAACAAGATCTTG |
| 222 | rs1528460_iSNPI_S_R | TGGAGATCAATATTTAGCCTTAACATAT |
| 223 | rs159606_iSNPI_S_R | GACTGTTTCTCATCCTGTTATTATTTGT |
| 224 | rs1736442_iSNPI_S_R | AACACACAGAAACATCAAGCTGAGC |
| 225 | rs1821380_iSNPI_S_R | TTCCTGACATTCTCCTTCTTCTATCTG |

TABLE 2-continued

SNP targeted primers

| SEQ ID NO | SNP PRIMER | EXAMPLES OF SNP PRIMERS WITHOUT TAGS |
|---|---|---|
| 226 | rs1886510_iSNPI_S_R | TATGACGCCTGGATTTTCACAACAAC |
| 227 | rs1979255_iSNPI_S_R | CAGAGACTATGGATGGTATTTAGGTCAA |
| 228 | rs2016276_iSNPI_S_R | ACTTTGTGTGGCTGAGAGAGAGAAA |
| 229 | rs2040411_iSNPI_S_R | TGAGTGTTCTCTGTATTTTCTTACTCTAAG |
| 230 | rs2046361_iSNPI_S_R2 | ATTTTTGGTCATTGTTGACACTTCACC |
| 231 | rs2056277_iSNPI_S_R2 | GGTGTTAGGGAGACAGGCATGAATG |
| 232 | rs2076848_iSNPI_S_R | TGAAACTTTTCAACTCTCCTACCGCC |
| 233 | rs2107612_iSNPI_S_R | GTTAAAATTGCCACTAATTATGTGTTTT |
| 234 | rs2111980_iSNPI_S_R | AACTGATCCTATGCAGCAAGATCTTTG |
| 235 | rs214955_iSNPI_S_R | GATGCTTGCAAACAAAGACTGAAAAGG |
| 236 | rs221956_iSNPI_S_R | GTCTGTGTGTCCTCTGAGATGATGAATG |
| 237 | rs2342747_iSNPI_S_R | GGGAGGAAGAAAACAGAGAGTCTTGA |
| 238 | rs2399332_iSNPI_S_R | AGTTTGTTGGCTTCTTTTGAGAAGTATC |
| 239 | rs251934_iSNPI_S_R | GGCAGATGAAGTAGTAGATATCTGGCTG |
| 240 | rs279844_iSNPI_S_R | GTTCAGTGTCAATTTTGACCAGATATT |
| 241 | rs2830795_iSNPI_S_R | AGACATAGGACACACCATTTTATTGTCT |
| 242 | rs2831700_iSNPI_S_R | TCAAAATATTTGGCTAAACTATTGCCGG |
| 243 | rs2920816_iSNPI_S_R2 | CTGGAGTTATTAATAAATTGGATTATATAGC |
| 244 | rs321198_iSNPI_S_R | TTACCTGTTTTCCTTTTGTGATTCCAC |
| 245 | rs338882_iSNPI_S_R | ACCAAGTCAAGAGCTCTGAGAGACAT |
| 246 | rs354439_iSNPI_S_R | ACAGTGAATGATATTCAGAATATTGTGC |
| 247 | rs3780962_iSNPI_S_R | GAACAAGGTCAAGATATCAGCTTTCACC |
| 248 | rs430046_iSNPI_S_R | AGGTCATACAATGAATGGTGTGATGT |
| 249 | rs4364205_iSNPI_S_R | ATCCACCCATGAGAAATATATCCACAA |
| 250 | rs445251_iSNPI_S_R | ACAATTCAAATTAATGTAAAAACTGCAAGTG |
| 251 | rs4606077_iSNPI_S_R | TAGTTCTAGTGTGGGATCTGACTCC |
| 252 | rs560681_iSNPI_S_R | GAACATCTGTTCAGGTTTCTCTCCATC |
| 253 | rs6444724_iSNPI_S_R | GAAAGGACTAAATTGTTGAACACTGGT |
| 254 | rs6811238_iSNPI_S_R | TGTGTGTTTTAAAGCCAGGTTTGTT |
| 255 | rs7041158_iSNPI_S_R | GATGGACTGGAACTGAGGATTTTCA |
| 256 | rs717302_iSNPI_S_R | AGCTTTAGAAAGGCATATCGTATTAACTG |
| 257 | rs719366_iSNPI_S_R | TTATAGTGAGTAAAGGACAGGCCCC |
| 258 | rs722098_iSNPI_S_R2 | ACACATCTGTTGACAGTAATGAAATATCC |
| 259 | rs722290_iSNPI_S_R | GTTTAAACTTGGATACCATCCCCAAGAC |
| 260 | rs727811_iSNPI_S_R | ATGAGATTGCTGGGAGATGCAGATG |
| 261 | rs729172_iSNPI_S_R | CACATTTCCCTCTTGCGGTTACATAC |
| 262 | rs733164_iSNPI_S_R | GACAAGCCTCGCTTGAGTTTTCTTT |

TABLE 2-continued

SNP targeted primers

| SEQ ID NO | SNP PRIMER | EXAMPLES OF SNP PRIMERS WITHOUT TAGS |
|---|---|---|
| 263 | rs735155_iSNPI_S_R | TGTGAGAGTGTCACCGAATTCAACG |
| 264 | rs740598_iSNPI_S_R | AAATAGCAATGGCTCGTCTATGGTTAG |
| 265 | rs740910_iSNPI_S_R | TGCTAAGTAAGGTGAGTGGTATAATCA |
| 266 | rs763869_iSNPI-S_R | ATAAATATGATGTGGCTACTCCCTCAT |
| 267 | rs8037429_iSNPI_S_R | GCTACACCTCCATAGTAATAATGTAAGAG |
| 268 | rs8078417_iSNPI_S_R | TGAAGCAGCTAGAGAACTCTGTACGT |
| 269 | rs826472_iSNPI_S_R2 | TTTTGTCTCTGTTATATTAGTCACCTATCTC |
| 270 | rs873196_iSNPI_S_R | ATAGCCCTGCATTCAAATCCCAAGTG |
| 271 | rs876724_iSNPI_S_R | TCCATTTTTATACCACTGCACTGAAG |
| 272 | rs891700_iSNPI_S_R2 | GCAGTAAAACATTTTCATCAAATTTCCA |
| 273 | rs901398_iSNPI_S_R | TCTGGGTGCAAACTAGCTGAATATCAG |
| 274 | rs907100_iSNPI_S_R | GAAAATCTGGAGGCAATTCATGATGCC |
| 275 | rs914165_iSNPI_S_R | ATACAATGATGATCACACGGGACCCT |
| 276 | rs917118_iSNPI_S_R | CCATGAAGATGGAGTCAACATTTTACA |
| 277 | rs938283_iSNPI_S_R | TCCTAACCCCTAGTACGTTAGATGTG |
| 278 | rs964681_iSNPI_S_R | GAGGTGATTTCTGTGAGGAACGTCG |
| 279 | rs987640_iSNPI_S_R | GTACATTCACTTAACAGGCTCTCTTTCC |
| 280 | rs9905977_iSNPI_S_R | AATTCATGAGCTGGTGTCCAAGGAG |
| 281 | rs993934_iSNPI_S_R | ATAACAGTCTCCAGAGTATATTAGCTTAG |
| 282 | rs9951171_iSNPI_S_R | GTTCCTCTGGGATGCAACATGAGAG |
| 283 | rs10497191_aSNPI_T_F | GAAAGGATGAAGAGGGTGGATATTGGAG |
| 284 | rs1079597_aSNPI_T_F | CCAAACCTCATCATCTCTTACCTGGATT |
| 285 | rs11652805_aSNPI_T_F | GTCCAAAGTCAAGTGCAAGTATAGTTGG |
| 286 | rs1229984_aSNPI_T_F | ACAATCTTTTCTGAATCTGAACAGCTTC |
| 287 | rs12439433_aSNPI_T_F | CAAAGGAAGGCATTTCCTAATGATCTTC |
| 288 | rs12498138_aSNPI_T_F | CTTTGCTTTGCTTTTCTTCTTCAGGGAA |
| 289 | rs12913832_pSNPI_NU_T_F | CTGCTTCAAGTGTATATAAACTCACAGT |
| 290 | rs1426654_aSNPI_T_F | CCTAGGAAAGCAGTAACTAATTCAGGAG |
| 291 | rs1462906_aSNPI_T_F | GCAATTTGTTCACTTTTAGTTTCGTAGC |
| 292 | rs1572018_aSNPI_T_F | GGCCTAATATGCATGTGTTCATGTCTCT |
| 293 | rs16891982_aSNPI_T_F | CAGAGTTTCTCATCTACGAAAGAGGAGT |
| 294 | rs174570_aSNPI_T_F | ATCCTAGACCTCCAGGTGGAATGATC |
| 295 | rs17642714_aSNPI_T_F | CTTGGCTGTCTCAATATTTTGGAGTAAG |
| 296 | rs1800414_aSNPI_T_F | GAGTAAATGAGCTGTGGTTTCTCTCTTA |
| 297 | rs1834619_aSNPI_T_F | CTTTCCATGTGGACCCTTTAACATTCAG |
| 298 | rs1876482_aSNPI_T_F | GCATAGTGAGCTGTTGATAGAGCTTTTG |
| 299 | rs1919550_aSNPI_T_F | CTAGAACAAAATCATTGGCTCTCCTAGT |

TABLE 2-continued

SNP targeted primers

| SEQ ID NO | SNP PRIMER | EXAMPLES OF SNP PRIMERS WITHOUT TAGS |
|---|---|---|
| 300 | rs192655_aSNPI_T_F | GTCTGGTGAGTACTGGCTGAATGTAAA |
| 301 | rs200354_aSNPI_T_F | CCAGAGGATGCTGCTAAACATTCTACAA |
| 302 | rs2024566_aSNPI_T_F | GCTCATGCCTGGAATTCACCTTTATTTT |
| 303 | rs2042762_aSNPI_T_F | CTAACTAGACATTTGGGCCACCTTACTT |
| 304 | rs2166624_aSNPI_T_F | GTCTATGGTGCCTATAGAATGTACAGGT |
| 305 | rs2196051_aSNPI_T_F | CCCTCTCAAGTTTGTGAGCAAATATCAC |
| 306 | rs2238151_aSNPI_T_F | CTCTATCTTGCTGCAATGGACTTTCC |
| 307 | rs260690_aSNPI_T_F | CCTAGAAACAGATTTTGAAGGGCTCTTG |
| 308 | rs2814778_aSNPI_T_F | AAATGAGGGGCATAGGGATAAGGGA |
| 309 | rs310644_aSNPI_T_F | CCTAGAAATCTGATACGTTATCCTATGA |
| 310 | rs3737576_aSNPI_T_F | AGGAGAGATATATTCAACATGAACCCAA |
| 311 | rs3811801_aSNPI_T_F | GAACATCTCTGACCAGAAATTTCCAGTA |
| 312 | rs3823159_aSNPI_T_F | GTGTAGTGAAATCCTTAGACTTAGGTAA |
| 313 | rs3916235_aSNPI_T_F | AATACATGAAAAAGTAATACATGGGGCA |
| 314 | rs4471745_aSNPI_T_F | ATTAAATGTTTACTTCTATCTACAAGGA |
| 315 | rs4833103_aSNPI_T_F | CATTTTGTGAAATGCAAAGGGCAAATCT |
| 316 | rs4891825_aSNPI_NU_T_F | GCTGAGAGGCTTAATTCCATCAAGATGA |
| 317 | rs4918664_aSNPI_NU_T_F | CCCATCCTAAACTTAGTTTTATGGGCAG |
| 318 | rs6754311_aSNPI_T_F | GTAACACATTCTCTTTGGGAAGCTAGC |
| 319 | rs6990312_aSNPI_NU_T_F | CTTAGCTTCAGTGAAAATGGTTCCTCTC |
| 320 | rs7226659_aSNPI_NU_T_F | CTTTCTTAGCTCCTCTCCATTTCTCTTC |
| 321 | rs7326934_aSNPI_NU_T_F | GTCTATGCAGTGCTTCACTGAGGATTAT |
| 322 | rs735480_aSNPI_NU_T_F | CTCTATCTGCTCAGAGCCTGCTTAAAAG |
| 323 | rs7554936_aSNPI_NU_T_F | GGAAAGGATACAGTGTTGAGCAAGATAG |
| 324 | rs7657799_aSNPI_NU_T_F | GCCAACTTGATTCTCTTTCAAATGCTTG |
| 325 | rs7722456_aSNPI_T_F | AGATGGGGTTTACCATGTTTCCCAG |
| 326 | rs798443_aSNPI_T_F | GTACAGTAGTTAGTTTCCAGACTGATGA |
| 327 | rs7997709_aSNPI_T_F | GTAAATATCTAACTGTGTTTCCCTCAGT |
| 328 | rs870347_aSNPI_T_F | GAACCAAAAGGAATTAAGAGACTAGGGG |
| 329 | rs917115_aSNPI_T_F | CTGCTTTTACGGCTTCTTCCTTTCTTC |
| 330 | rs10497191_aSNPI_S_R | CCCACATCCTTCCCATTTATAGGCAA |
| 331 | rs1079597_aSNPI_S_R | TACATGATCCTAAGGGCAGCAGGAA |
| 332 | rs11652805_aSNPI_S_R | GTTTGGTGCATCCTCTTTCTCTCTC |
| 333 | rs1229984_aSNPI_S_R | GACTGTAGTCACCCCTTCTCCAACA |
| 334 | rs12439433_aSNPI_S_R | AGAGTGAAATACATAGAAAAGAAACTTAAAG |
| 335 | rs12498138_aSNPI_S_R | ATTTGCGAGAAACAGATAAATATTGAAG |
| 336 | rs12913832_pSNPI_NU_S_R | ACAGGAACAAAGAATTTGTTCTTCATGG |

TABLE 2-continued

SNP targeted primers

| SEQ ID NO | SNP PRIMER | EXAMPLES OF SNP PRIMERS WITHOUT TAGS |
|---|---|---|
| 337 | rs1426654_aSNPI_S_R | CCTTGGATTGTCTCAGGATGTTGCA |
| 338 | rs1462906_aSNPI_S_R | CTGGGATGTTTGTTTTGGCTTTGTG |
| 339 | rs1572018_aSNPI_S_R | ATTGGTAGTACACTAATGGATATATGTGAG |
| 340 | rs16891982_aSNPI_S_R | GAATAAAGTGAGGAAAACACGGAGTTG |
| 341 | rs174570_aSNPI_S_R | GAGAGAGGCAGAAAGGAGGGATGAA |
| 342 | rs17642714_aSNPI_S_R | TACTCTGTCTTCAGTAGCTGTTTCTTGG |
| 343 | rs1800414_aSNPI_S_R | TTAGACTCACCAAGATCAAGATGAATGC |
| 344 | rs1834619_aSNPI_S_R | ATCTCAATAAAGCTGTTCAAAACAGAAAG |
| 345 | rs1876482_aSNPI_S_R | TAAAGAAAATGCCATGGGCTGTACCC |
| 346 | rs1919550_aSNPI_S_R | ATTGTGCAGCAGAACAGAGTGTAGTG |
| 347 | rs192655_aSNPI_S_R | ATTCTTTGCATAGCTCACGAAATTTCCC |
| 348 | rs200354_aSNPI_S_R | AAAATGAGACCTCGTATCTTTGCAGC |
| 349 | rs2024566_aSNPI_S_R | AAATGCAGAACTGCCAAAAGAAACCC |
| 350 | rs2042762_aSNPI_S_R | GAGAATCTGTGAATGCCAGGGTCTG |
| 351 | rs2166624_aSNPI_S_R | ATGGATTCATGTTTCAGACATCTAATT |
| 352 | rs2196051_aSNPI_S_R | ATCACTAGAAAGAAAAGAGTTCCTATTC |
| 353 | rs2238151_aSNPI_S_R | GAAGTTTAAAAGAGTGGGAACATGGGG |
| 354 | rs260690_aSNPI_S_R | CTACGTAAGCAAAAATGATCACGCAC |
| 355 | rs2814778_aSNPI_S_R | AACCTGATGGCCCTCATTAGTCCTT |
| 356 | rs310644_aSNPI_S_R | CACCAGATTTCTAGGAATAGCATGTGAG |
| 357 | rs3737576_aSNPI_S_R | AAGAGCATAGTGAGGGGTTAGACCT |
| 358 | rs3811801_aSNPI_S_R | CTTTATATTTAGTGTAGAGATCAGTCTCC |
| 359 | rs3823159_aSNPI_S_R | TGAGTCCTTTACCTAATCTTGGTTGTC |
| 360 | rs3916235_aSNPI_S_R | AATCCAAAGCAACTCTCTTTTCACCAC |
| 361 | rs4471745_aSNPI_S_R | TTTACTGGAACCCTGATTTTGTTGGA |
| 362 | rs4833103_aSNPI_S_R | TGCCACTGATATATCAGTACCTGAGT |
| 363 | rs4891825_aSNPI_NU_S_R | ACAATCTCAATCCCCCTTAATGTTTTC |
| 364 | rs4918664_aSNPI_NU_S_R | GTGGGCAGAGAGAGTAAGAGAACCT |
| 365 | rs6754311_aSNPI_S_R | CAAACCAGATTCTGGCAGAATAGTTAGC |
| 366 | rs6990312_aSNPI_NU_S_R | CTTCTCTCCCATCCTCCTTCTCCAC |
| 367 | rs7226659_aSNPI_NU_S_R | AGATCAAGGGATCTGTGGGACAATAAC |
| 368 | rs7326934_aSNPI_NU_S_R | GGGGAGTGATTTCAAGCATCCTGATT |
| 369 | rs735480_aSNPI_NU_S_R | CATGAGTTTGAGGTAAGATGAAGGAGA |
| 370 | rs7554936_aSNPI_NU_S_R | TCTCTCTCATCCTAGTGAATGCCATC |
| 371 | rs7657799_aSNPI_NU_S_R | GGGTGATGATCTACCTTGCAGGTATA |
| 372 | rs7722456_aSNPI_S_R | CTCAAGGCCCTGGGTCTGAAATTAC |
| 373 | rs798443_aSNPI_S_R | ACATCTCCAGTTAATAATTTCCACTAAC |

TABLE 2-continued

SNP targeted primers

| SEQ ID NO | SNP PRIMER | EXAMPLES OF SNP PRIMERS WITHOUT TAGS |
|---|---|---|
| 374 | rs7997709_aSNPI_S_R | TGGATTGCTCAACAAATAGTGCTAAAA |
| 375 | rs870347_aSNPI_S_R | CATGCGACATCCAGGTAGCTAAAATAC |
| 376 | rs917115_aSNPI_S_R | ATGGATAAAAATGGAACTTTCAAGAGAA |
| 377 | rs12203592_pSNPI_T_F | GTTTTATGTAAAGCTTCGTCATATGGCT |
| 378 | rs12821256_pSNPI_T_F | GTTCCAACTTAGTCATAAAGTTCCCTGG |
| 379 | rs12896399_pSNPI_T_F | GGGTCTTGATGTTGTATTGATGAGGAAG |
| 380 | rs1393350_pSNPI_T_F | CCTAACAGAAAGTCACTGTTTGTATCTG |
| 381 | rs1800407_pSNPI_T_F | TCACTCTGGCTTGTACTCTCTGTG |
| 382 | rs2378249_pSNPI_T_F | GGCTGGTTTCAGTCTGGAGACTTTATTT |
| 383 | rs2402130_pSNPI_T_F | CTTCACCTCGATGACGATGATGATGAT |
| 384 | rs4959270_pSNPI_T_F | GACAATAACAGCACAAAGGATGGAAAAG |
| 385 | rs1805009_pSNPI_T_F | GAACCAGACCACACAATATCACCAC |
| 386 | rs28777_pSNPI_T_F | TCTACCTCTTTGATGTCCCCTTCGATAG |
| 387 | rs16891982_pSNPI_T_F | CAGAGTTTCTCATCTACGAAAGAGGAGT |
| 388 | rs683_pSNPI_T_F | CCCAGCTTTGAAAAGTATGCCTAGAACT |
| 389 | rs12913832_pSNPI_T_F | CTGCTTCAAGTGTATATAAACTCACAGT |
| 390 | rs12203592_pSNPI_S_R | TTGTTTCATCCACTTTGGTGGGTAAAAG |
| 391 | rs12821256_pSNPI_S_R | TAATTAAGCTCTGTGTTTAGGGTTTTT |
| 392 | rs12896399_pSNPI_S_R | CAATTCTTTGTTCTTTAGGTCAGTATAT |
| 393 | rs1393350_pSNPI_S_R | TACTCTTCCTCAGTCCCTTCTCTGC |
| 394 | rs1800407_pSNPI_S_R | TGAGACAGAGCATGATGATCATGGC |
| 395 | rs2378249_pSNPI_S_R | GCACAAGTCTAGGAACTACTTTGCAC |
| 396 | rs2402130_pSNPI_S_R | GAAGTATTTGAACCATACGGAGCCC |
| 397 | rs4959270_pSNPI_S_R | TGAGGAACACATCCAAACTATGACAC |
| 398 | rs1805009_pSNPI_S_R | TTTCTCGCCCTCATCATCTGCAATG |
| 399 | rs28777_pSNPI_S_R | TCAGTTGATTTCATGTGATCCTCACAG |
| 400 | rs16891982_pSNPI_S_R | GAATAAAGTGAGGAAAACACGGAGTTG |
| 401 | rs683_pSNPI_S_R | ATTACCTTCTTTCTAATACAAGCATATG |
| 402 | rs12913832_pSNPI_S_R | ACAGGAACAAAGAATTTGTTCTTCATGG |

Example 2—DNA Profiling for Databanking

This example describes an experiment following the workflow of FIG. 2. This example does not utilize UMIs, as it could be assumed that the samples obtained are from individuals whose identity is already known.

For this experiment, STRs are multiplexed with iSNPs as found in Table 3.

TABLE 3

Identity informative SNPs and STRs

Identity informative SNPs

| rs1005533 | rs1357617 | rs2076848 | rs4530059 | rs763869 |
| rs10092491 | rs1360288 | rs2107612 | rs4606077 | rs8037429 |
| rs1015250 | rs1382387 | rs2111980 | rs560681 | rs8078417 |
| rs1024116 | rs1413212 | rs214955 | rs576261 | rs826472 |

TABLE 3-continued

Identity informative SNPs and STRs

| | | | | |
|---|---|---|---|---|
| rs1028528 | rs1454361 | rs221956 | rs6444724 | rs873196 |
| rs1029047 | rs1463729 | rs2269355 | rs6811238 | rs876724 |
| rs1031825 | rs1490413 | rs2342747 | rs6955448 | rs891700 |
| rs10488710 | rs1493232 | rs2399332 | rs7041158 | rs901398 |
| rs10495407 | rs1498553 | rs251934 | rs717302 | rs907100 |
| rs1058083 | rs1523537 | rs279844 | rs719366 | rs914165 |
| rs10773760 | rs1528460 | rs2830795 | rs722098 | rs917118 |
| rs10776839 | rs159606 | rs2831700 | rs722290 | rs938283 |
| rs1109037 | rs1736442 | rs2920816 | rs727811 | rs964681 |
| rs1294331 | rs1821380 | rs321198 | rs729172 | rs987640 |
| rs12997453 | rs1886510 | rs338882 | rs733164 | rs9905977 |
| rs13182883 | rs1979255 | rs354439 | rs735155 | rs993934 |
| rs13218440 | rs2016276 | rs3780962 | rs737681 | rs9951171 |
| rs1335873 | rs2040411 | rs430046 | rs740598 | |
| rs1336071 | rs2046361 | rs4364205 | rs740910 | |
| rs1355366 | rs2056277 | rs445251 | rs7520386 | |

Autosomal STRs

| | | | | |
|---|---|---|---|---|
| D1S1656 | CSF1PO | vWA | D21S11 | D4S2408 |
| D2S441 | D7S820 | D13S317 | TPOX | D17S1301 |
| D2S1338 | D8S1179 | Penta E | SE33 | D9S1122 |
| D3S1358 | D10S1248 | D16S539 | Penta D | D6S1043 |
| FGA | TH01 | D18S51 | D22S1045 | Amelogenin |
| D5S818 | D12S391 | D19S433 | D20S482 | |

X STRs

| | | | | |
|---|---|---|---|---|
| DXS8378 | DXS8377 | DXS10101 | DXS10148 | DXS10146 |
| DXS7132 | DXS10135 | DXS10134 | DXS10079 | |
| HPRTB | DXS10074 | DXS7423 | DXS10103 | |

Y STRs

| | | | | |
|---|---|---|---|---|
| DYS456 | DYS393 | DYS437 | DYS533 | DYS449 |
| DYS389I/II | DYS391 | DYS438 | DYS518 | DYS522 |
| DYS390 | DYS439 | DYS448 | DYS570 | DYS505 |
| DYS458 | DYS635 | DYS576 | DYS643 | DYS627 |
| DYS19 | DYS392 | DYS481 | DYS460 | DYF387S1a/b |
| DYS385a/b | YGATAH4 | DYS549 | DYS612 | |

Additional SNPs and STRs could of course be added to the above list. Examples of other potential targets include, but are not limited to, those markers found in

TABLE 4

Examples of additional STRs and SNPs for multiplexing

Identity informative SNPs

| | | | | |
|---|---|---|---|---|
| rs1004357 | rs1554472 | rs2567608 | rs521861 | rs9606186 |
| rs1019029 | rs1872575 | rs2811231 | rs5746846 | rs985492 |
| rs1027895 | rs2073383 | rs2833736 | rs590162 | rs9866013 |
| rs10500617 | rs2175957 | rs315791 | rs6591147 | |
| rs10768550 | rs2255301 | rs3744163 | rs689512 | |
| rs12480506 | rs2270529 | rs4288409 | rs7205345 | |
| rs13134862 | rs2272998 | rs464663 | rs7229946 | |
| rs1358856 | rs2291395 | rs4789798 | rs7704770 | |
| rs1410059 | rs2292972 | rs4796362 | rs8070085 | |
| rs1478829 | rs2503107 | rs4847034 | rs9546538 | |

Autosomal STRs

| | | | |
|---|---|---|---|
| D1S1677 | D3S4529 | D18S853 | D10S1435 |
| D11S4463 | D6S1017 | D14S1434 | D5S2500 |
| D1S1627 | D1GATA113 | D2S1776 | |

Primers were designed to contain a gene-specific PCR primer sequence at the 3' end and an adapter tag sequence at the 5' end. In this experiment, the forward primers contain the tag sequence for the TruSeq Custom Amplicon i5 adapters and the reverse primers contain the tag sequence for the TruSeq Small RNA kit i7 adapters. The tags can be used as amplification primer sites as well as sequencing primer sites.

(SEQ ID NO: 403)
Adapter i5 tag sequence 5'TACACGACGCTCTTCCGATCT3'

(SEQ ID NO: 404)
Adapter i7 tag sequence 5'CTTGGCACCCGAGAATTCCA3'

To balance the amplification between the STRs and the SNPs in the multiplex, primer design parameters were modified for the SNPs as described in Example 1. The original set of SNP primers designed using Illumina's Design Studio were classic PCR primers—short sequences with high melting temperatures and little to no secondary structure. Design Studio was used to design TruSeq Custom Amplicon Probes and to create the reverse complement of the down-stream probe to make the reverse PCR primer. These primers, however, did not multiplex well and one bad primer could turn the assay from good to bad (e.g., all primer-dimer and no product) (FIG. 4.) In an attempt to create better primers for multiplexing, Primer3 (shareware) was used that contains a mispriming library feature. It was discovered that the Primer3 designed primers performed even more poorly in the multiplex assay than the Design Studio primers. Surprisingly, data were being generated showing that the STR primers were multiplexing well. It was observed that the poorly designed primer pairs directed to STR targets did not cause multiplex failures as the SNP primers did. The STR primers are long, AT-rich, and have low melting temperatures, contrary to what is known as a "good" primer.

The SNP primers were redesigned following the parameters of Example 1. The primers were mixed together for all of the targets. For this example, primer pairs for 56 STRs were mixed with primer pairs for 75 iSNPs, aSNPs, and phenotypic-informative SNPs. Polymerase (Hot-start Phusion II in this example) was added to a mastermix of all of the components required for PCR and the primers were added. The mix was pipetted into wells of a PCR plate, but the amplification could also be performed in tubes, etc. DNA was added to the plate as purified DNA in 15 microliter volume, however lysed extracts of blood or buccal samples from swabs or non-treated filter paper, or directly from blood or buccal samples on FTA Cards, etc. could also be used. For this experiment, purified control 2800M DNA at 1 ng and 100 pg was used. The reactions were subjected to PCR for a determined number of cycles (in the case of the example, 25 cycles) following the protocol:

| | |
|---|---|
| 95° C. | 3 min |
| 96° C. | 1 min |
| 54° C. | 2 min* |
| 68° C. | 45 sec ** |
| 60° C. | 30 min |
| 4° C. | hold |

*ramp 0.5° C./sec
** ramp 0.2° C./sec

After cycling, the plates were removed from the thermal cycler. The reaction was brought to 50 microliters with polymerase (Kapa HiFi, Kapa Biosystems), PCR mastermix containing all of the components required for PCR, and a pair of adapters (one i7 and one i5 adapter). A second round of PCR was performed for a determined number of cycles (10 cycles in the case of the example) to generate the sequencing libraries, following the protocol:

| | |
|---|---|
| 98° C. | 30 sec |
| 98° C. | 15 sec |
| 66° C. | 30 sec |
| 72° C. | 1 min |
| 72° C. | 5 min |
| 10° C. | hold |

After cycling, the plate containing the completed libraries was removed from the thermal cycler. At this point, the samples can be pooled by volume and purified as a single sample using magnetic beads (SPRI) for example. The samples also can be purified individually. The pool or the individual libraries can be quantified by using a qPCR-based method, by using a Fragment Analyzer or BioAnalyzer, or by using PicoGreen and a plate reader (as in the case of the example). A skilled artisan will know the myriad of options for library quantitation. If the libraries are purified individually, they can be normalized to 2 nM each concentration and pooled by volume.

Figure 6:
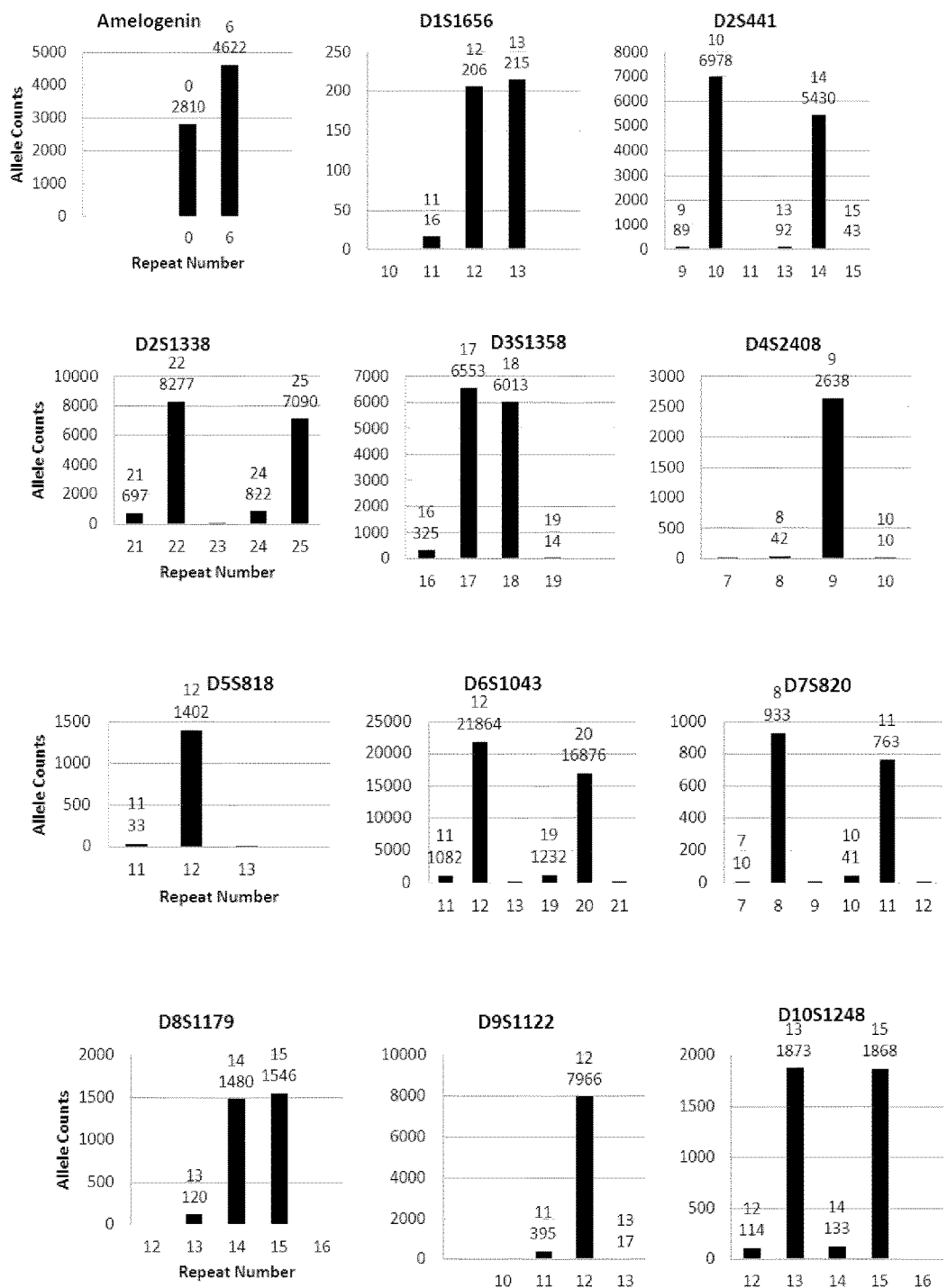
FIG. 6 shows a series of bar charts showing the exemplary STR loci plots from the experiment of FIG. 5. The plots show different allelic calls for the STRs in the panel of FIG. 5.
Figure 6:
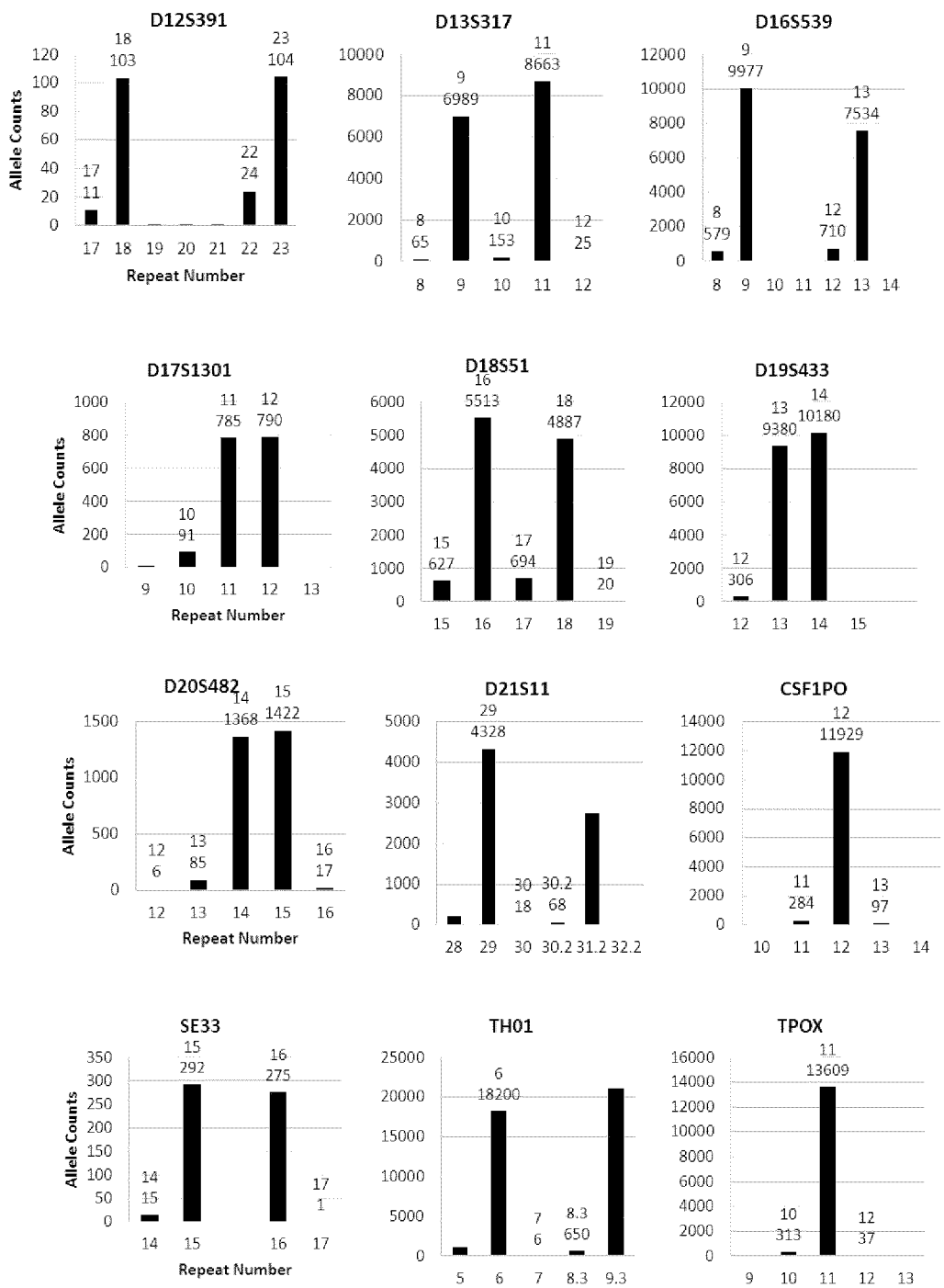
Figure 6:
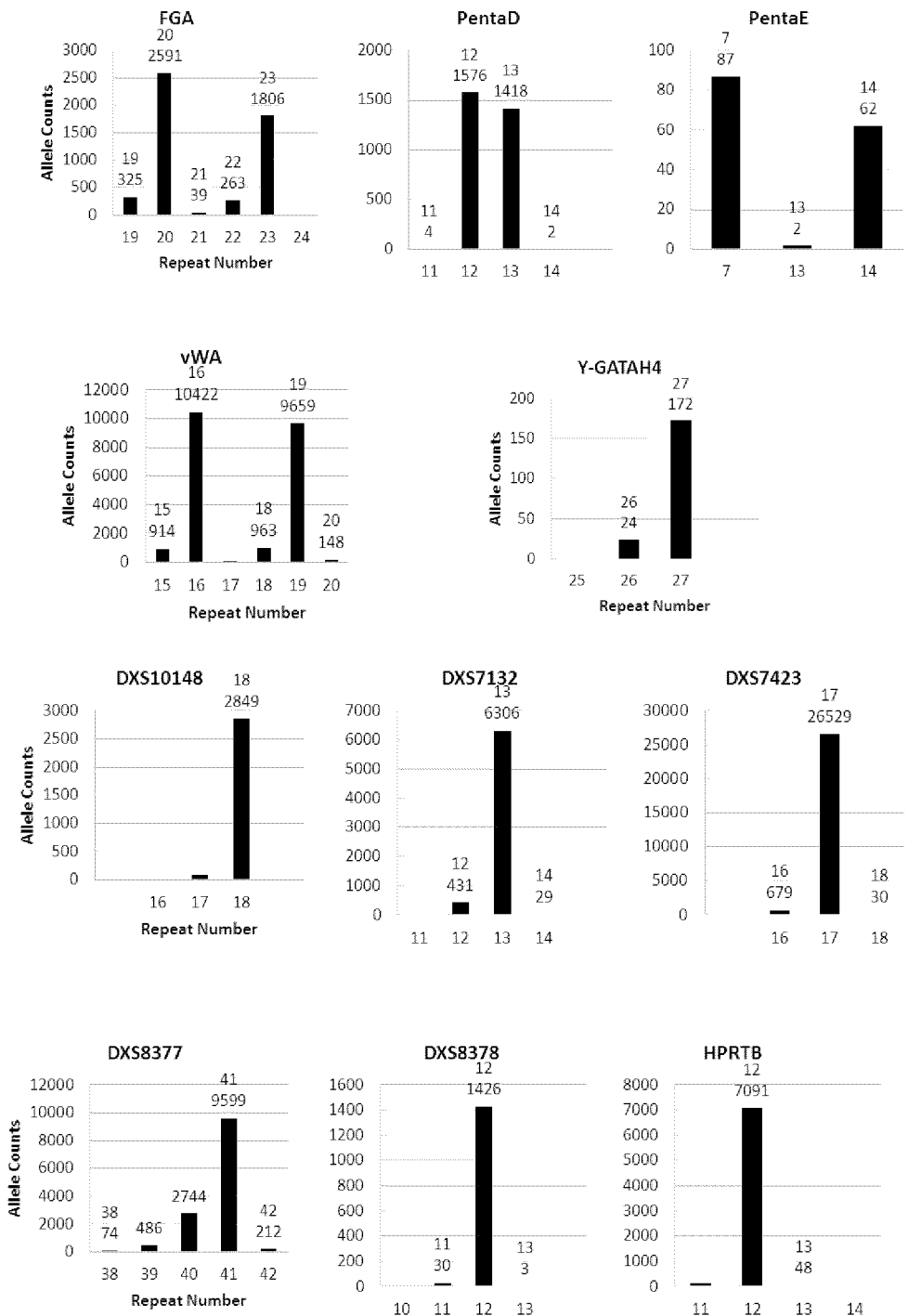
Figure 6:
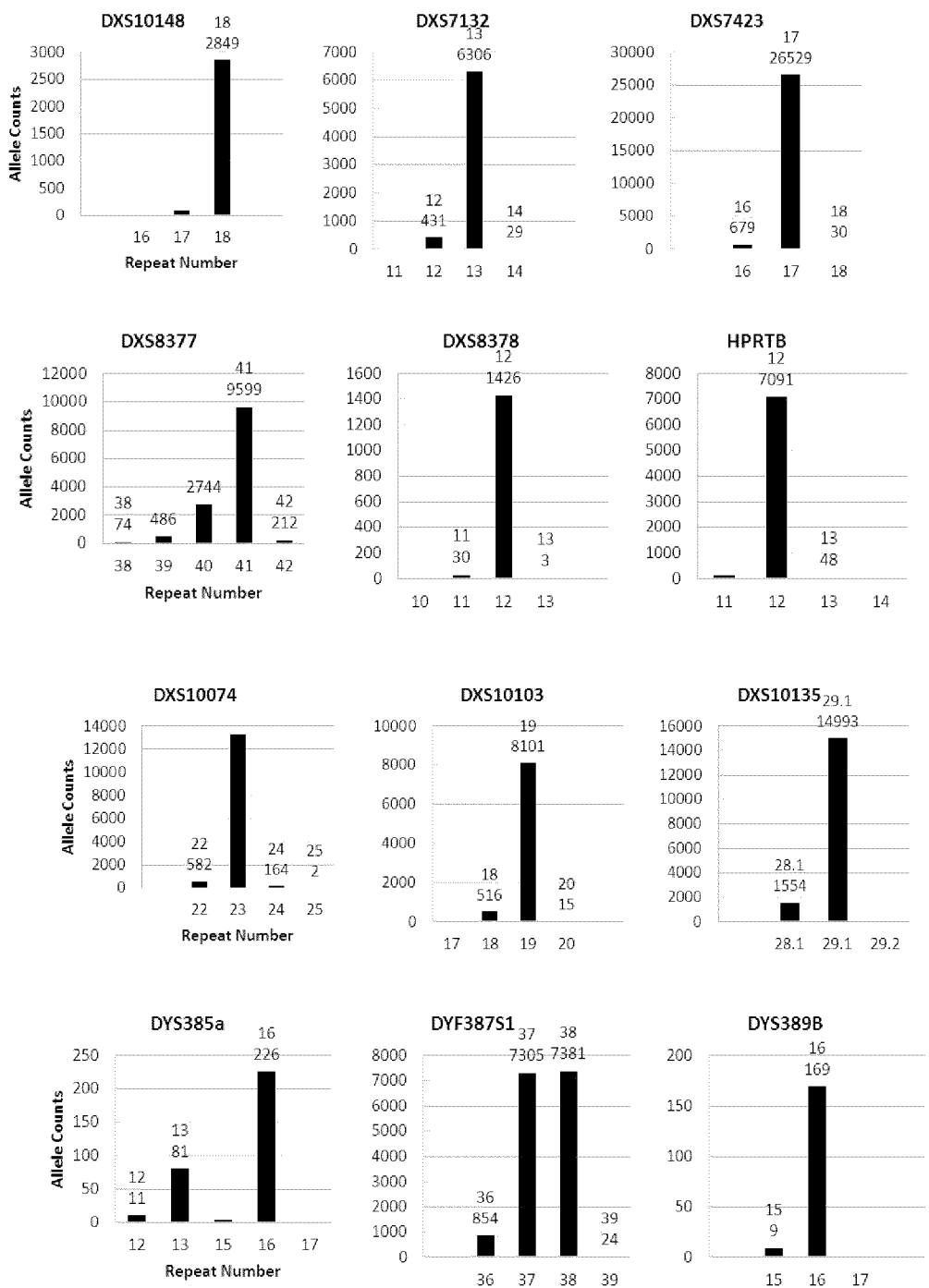
Figure 6:
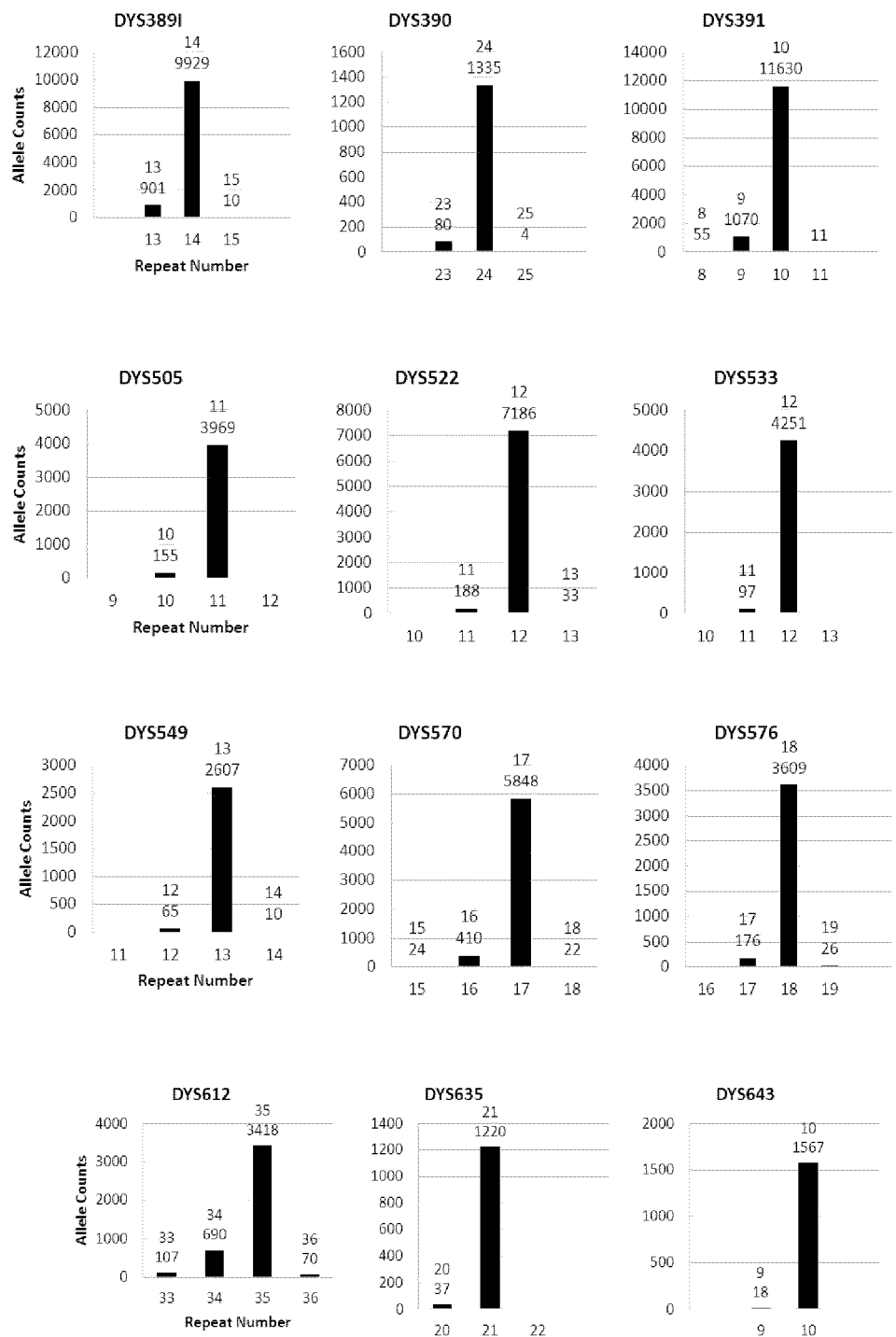

The pools of purified libraries were denatured, diluted, clustered and sequenced on the MiSeq sequencing instrument with a 350-cycle sequencing run and the two index reads. After sequencing, the samples were demultiplexed according to the adapter sequences and analyzed through the Forensics Genomics pipeline (Illumina, Inc.). The STR reads were separated from the SNP reads and analyzed independently. The STRs were analyzed using the algorithm described in a previous patent application (PCT/US2013/30867, incorporated herein by reference in its entirety). The repeat number(s) and any sequence variations were reported along with the read numbers. The SNPs were analyzed using a manifest and the calls were reported along with the read numbers. The relative balance between alleles (Min/Max %), balance between loci (% CV), error rates, and stutter rates were calculated for the STR loci. The results for the STRs in the initial databanking multiplex are shown in FIG. 5A-C. The balance (mean balance 80%), stutter (~3%) and error rates (less than 5%) meet design input requirements for the loci included in this example. The % CV (~142%) was calculated using all 56 loci. Even though the primers used show inter-locus balance, further primer optimization is anticipated to improve the inter-locus balance. The calls for the known loci match published results for 2800M. The results for the SNPs are shown in FIG. 5D-E. The coverage, allele calls, stutter and other artifacts for the 56 STR loci in the large multiplex are shown in FIG. 6. These graphs mimic the electropherograms generated by CE technology. The bars are analogous to peaks for the defined allele (X axis) and the read counts (Y axis) are analogous to RFU. The coverage for the SNPs was anywhere from 10-2500× depending on the SNP, however every SNP that was multiplexed was counted and provided accurate calls.

Example 3—DNA Profiling for Criminal Casework

This example describes an experiment following the workflow of FIG. 3. This example incorporates UMIs into the primers, as it could be assumed that the samples obtained are from individuals whose identity is not already known.

For this experiment, the STRs were multiplexed with iSNPs, aSNPs and phenotypic-informative SNPs as found in Table 5.

TABLE 5 case work STRs and SNPs

Identity informative SNPs

| | | | | |
|---|---|---|---|---|
| rs1005533 | rs1357617 | rs2076848 | rs4530059 | rs763869 |
| rs10092491 | rs1360288 | rs2107612 | rs4606077 | rs8037429 |
| rs1015250 | rs1382387 | rs2111980 | rs560681 | rs8078417 |
| rs1024116 | rs1413212 | rs214955 | rs576261 | rs826472 |
| rs1028528 | rs1454361 | rs221956 | rs6444724 | rs873196 |
| rs1029047 | rs1463729 | rs2269355 | rs6811238 | rs876724 |
| rs1031825 | rs1490413 | rs2342747 | rs6955448 | rs891700 |
| rs10488710 | rs1493232 | rs2399332 | rs7041158 | rs901398 |
| rs10495407 | rs1498553 | rs251934 | rs717302 | rs907100 |
| rs1058083 | rs1523537 | rs279844 | rs719366 | rs914165 |
| rs10773760 | rs1528460 | rs2830795 | rs722098 | rs917118 |
| rs10776839 | rs159606 | rs2831700 | rs722290 | rs938283 |
| rs1109037 | rs1736442 | rs2920816 | rs727811 | rs964681 |
| rs1294331 | rs1821380 | rs321198 | rs729172 | rs987640 |
| rs12997453 | rs1886510 | rs338882 | rs733164 | rs9905977 |
| rs13182883 | rs1979255 | rs354439 | rs735155 | rs993934 |
| rs13218440 | rs2016276 | rs3780962 | rs737681 | rs9951171 |
| rs1335873 | rs2040411 | rs430046 | rs740598 | |
| rs1336071 | rs2046361 | rs4364205 | rs740910 | |
| rs1355366 | rs2056277 | rs445251 | rs7520386 | |

Autosomal STRs

| | | | | |
|---|---|---|---|---|
| D1S1656 | CSF1PO | vWA | D21S11 | D4S2408 |
| D2S441 | D7S820 | D13S317 | TPOX | D17S1301 |
| D2S1338 | D8S1179 | Penta E | SE33 | D9S1122 |
| D3S1358 | D10S1248 | D16S539 | Penta D | D6S1043 |
| FGA | TH01 | D18S51 | D22S1045 | Amelogenin |
| D5S818 | D12S391 | D19S433 | D20S482 | |

X STRs

| | | | | |
|---|---|---|---|---|
| DXS8378 | DXS8377 | DXS10101 | DXS10148 | DXS10146 |
| DXS7132 | DXS10135 | DXS10134 | DXS10079 | |
| HPRTB | DXS10074 | DXS7423 | DXS10103 | |

Y STRs

| | | | | |
|---|---|---|---|---|
| DYS456 | DYS393 | DYS437 | DYS533 | DYS449 |
| DYS389I/II | DYS391 | DYS438 | DYS518 | DYS522 |
| DYS390 | DYS439 | DYS448 | DYS570 | DYS505 |
| DYS458 | DYS635 | DYS576 | DYS643 | DYS627 |
| DYS19 | DYS392 | DYS481 | DYS460 | DYF387S1a/b |
| DYS385a/b | YGATAH4 | DYS549 | DYS612 | |

Phenotypic informative SNPs

| | | | | |
|---|---|---|---|---|
| N29insA | rs1805006 | rs1110400 | rs12203592 | rs2378249 |
| rs11547464 | rs1805007 | rs28777 | rs1042602 | rs12896399 |
| rs885479 | rs1805009 | rs16891982 | rs1800407 | rs1393350 |
| rs1805008 | Y152OCH | rs12821256 | rs2402130 | rs683 |
| rs1805005 | rs2228479 | rs4959270 | rs12913832 | |

Ancestry informative SNPs

| | | | | |
|---|---|---|---|---|
| rs10497191 | rs17642714 | rs2238151 | rs4471745 | rs7554936 |
| rs1079597 | rs1800414 | rs2593595 | rs459920 | rs7657799 |
| rs11652805 | rs1834619 | rs260690 | rs4833103 | rs7722456 |
| rs1229984 | rs1871534 | rs2814778 | rs4891825 | rs798443 |
| rs12439433 | rs1876482 | rs310644 | rs4918664 | rs7997709 |
| rs12498138 | rs1919550 | rs3737576 | rs671 | rs870347 |
| rs12913832 | rs192655 | rs3811801 | rs6754311 | rs917115 |
| rs1426654 | rs200354 | rs3814134 | rs6990312 | rs9522149 |
| rs1462906 | rs2024566 | rs3823159 | rs7226659 | |
| rs1572018 | rs2042762 | rs3827760 | rs7251928 | |
| rs16891982 | rs2166624 | rs3916235 | rs7326934 | |
| rs174570 | rs2196051 | rs4411548 | rs735480 | |

This example includes UMIs for the STR primers. For these examples, only the STR primers contain UMIs, however both STR and SNP primers could include UMIs if desired and that option is not excluded from practice. For this example however only the STR primers incorporate UMIs for demonstration purposes. Unique molecule identifiers were introduced during two cycles of PCR (FIG. 3). First, as for Example 2, the PCR primers contain a gene-specific PCR primer sequence at the 3' end and an adapter tag sequence at the 5' end, the same as for tag sequences used in Example 2 for i5 and i7 sequences. In this experiment, the UMIs are positioned between the gene-specific primer sequence and the tag sequence. In the case of this example, there were five randomized bases used for the UMI on both the forward and reverse primers. The primers were mixed together for all of the targets. The primer mix comprised of 26 Autosomal STR primer pairs and 86 SNP primer pairs (92 SNPs covered). Polymerase (Hot-start Phusion II in this example) was added to a mastermix of all of the components required for PCR, and the primers were added. The mix was pipetted into wells of a PCR plate. DNA was added to the plate as purified DNA, optimally 1 ng. As in Example 2, purified DNA from 2800M control was tested at 1 ng. The multiplex reaction mixture was subjected to two cycles of PCR following the protocol:

| 98 C. | 3 min | |
|---|---|---|
| 98 C. | 2 min | |
| 54 C. | 12 min | ramp 0.2 C./sec |
| 72 C. | 4 min | 2 cycles |
| 4 C. | hold | |

After cycling, the samples were removed from the thermal cycler and *E. coli* single-stranded DNA binding protein (SSB) was added to the reaction. It was contemplated that the SSB reduces primer dimers by the unused tagged gene-specific primers and prevents any more amplification from these primers. The SSB was incubated with the sample on ice, alternatively RT or 37 C incubation could also be used. After this incubation, polymerase (Hot-start Phusion II in this example) was added to a mastermix of all of the components required for PCR, and the mastermix was added to the sample with a pair of adapters (i7 and i5 adapters) and cycled for a determined number of cycles (in this experiment 34 cycles), following the protocol:

| 95 C. | 3 min |
|---|---|
| 95 C. | 30 sec |
| 66 C. | 30 sec |
| 72 C. | 1 min |
| 72 C. | 5 min |
| 10 C. | hold |

The samples were purified with SPRI beads, and the individual libraries could be quantified by using a qPCR-based method, by using a Fragment Analyzer (as in the case of the example) or BioAnalyzer, or by using PicoGreen and a plate reader. The libraries were normalized to 2 nM each concentration and pooled by volume.

Figure 8:
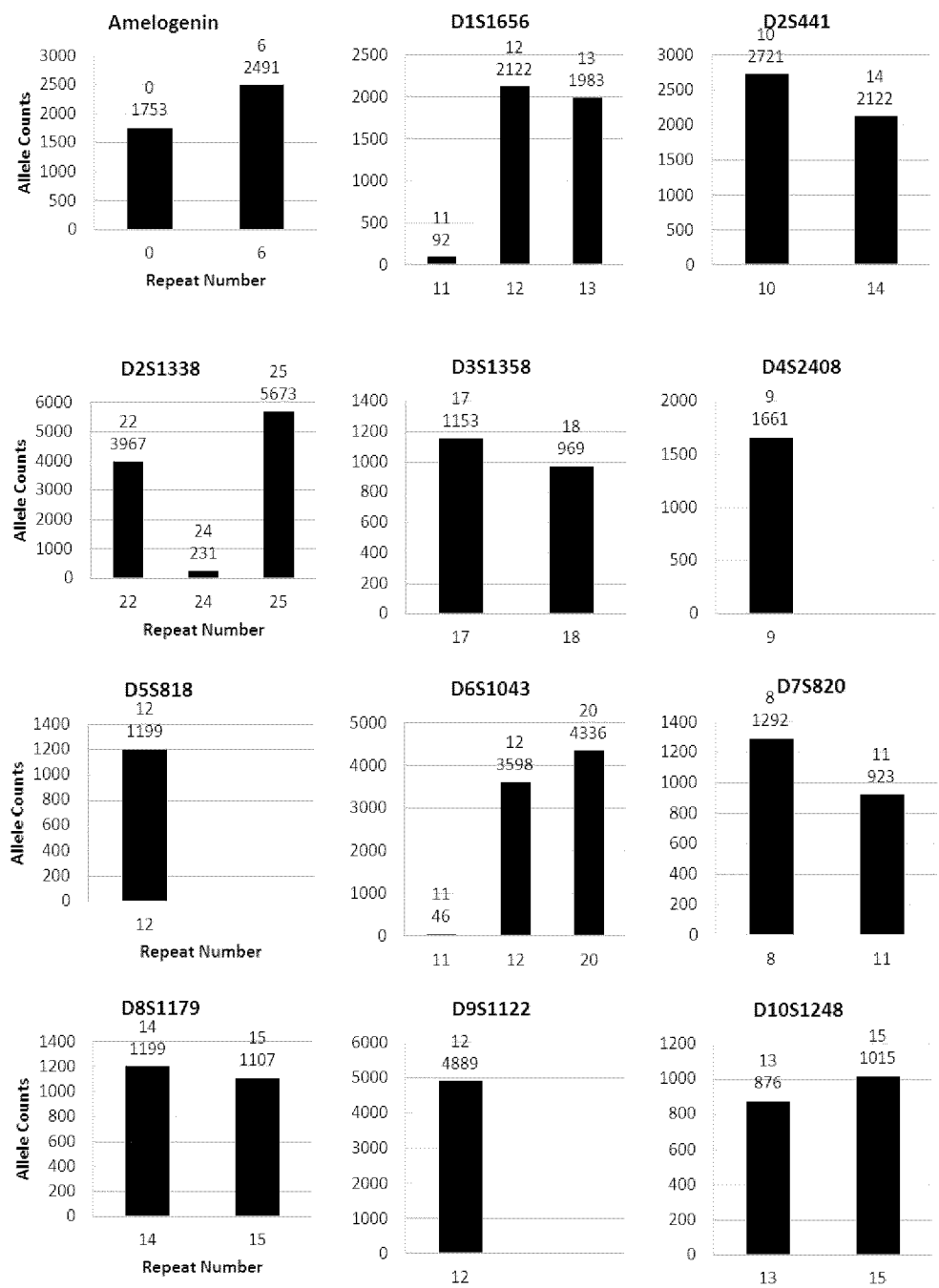
FIG. 8 shows a series of bar charts showing the exemplary STR loci plots from the experiment of FIG. 7. The plots show different allelic calls for the STRs in the panel of FIG. 7.
Figure 8:
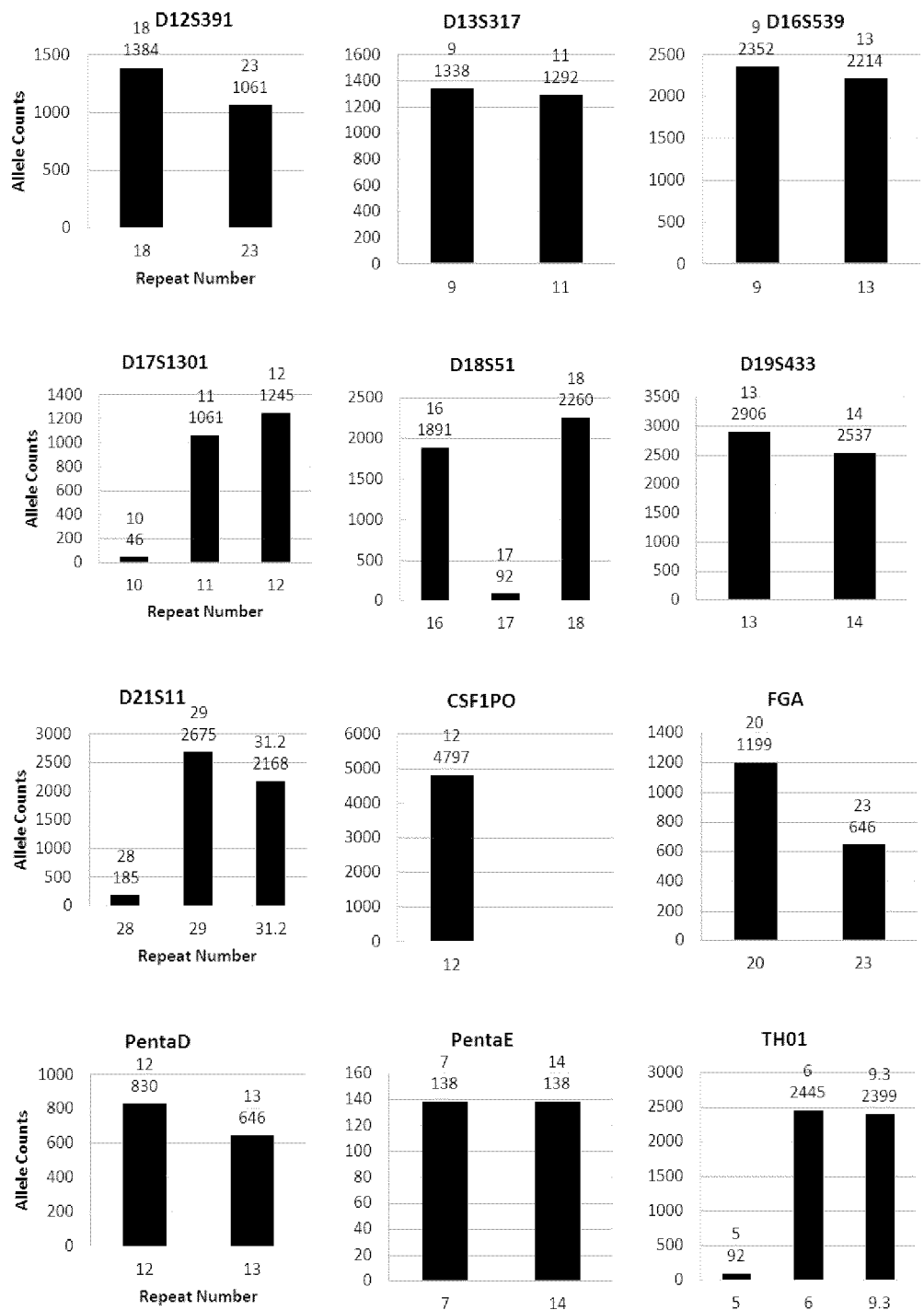
Figure 8:
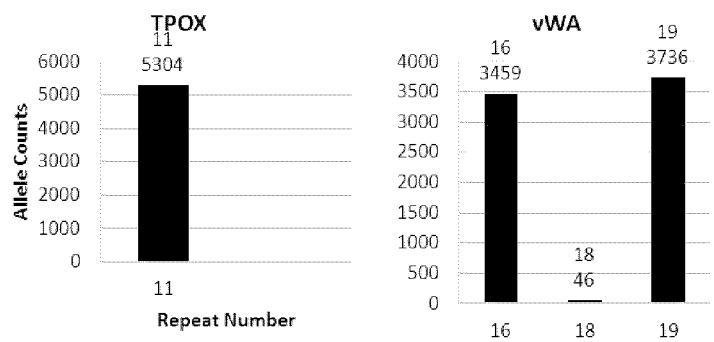

The pools of purified libraries were denatured, diluted, clustered and sequenced using the MiSeq with a 350×100-cycle sequencing run and the two index reads. After sequencing, data was determined as reported in Example 2. However, since the primers contain UMIs, the UMIs were used to collapse the data by using PCR duplicates to remove sequencing and PCR errors and artifacts. The SNPs were analyzed using a manifest and the calls were reported along with the read numbers. The relative balance between alleles (Min/Max %), balance between loci (% CV), error rates, and stutter rates (STRs, only) were calculated. The results for the initial casework multiplex are shown in FIG. 7A-E. The coverage, allele calls, stutter and other artifacts for the 26 STR loci in the large multiplex are shown in FIG. 8. These graphs mimic the electropherograms generated by CE. The bars are analogous to peaks and the read counts are analogous to RFU. The coverage for the SNPs was anywhere from 10-5500× depending on the SNP, however every SNP that was multiplexed was counted and provided useful results.

Figure 9:
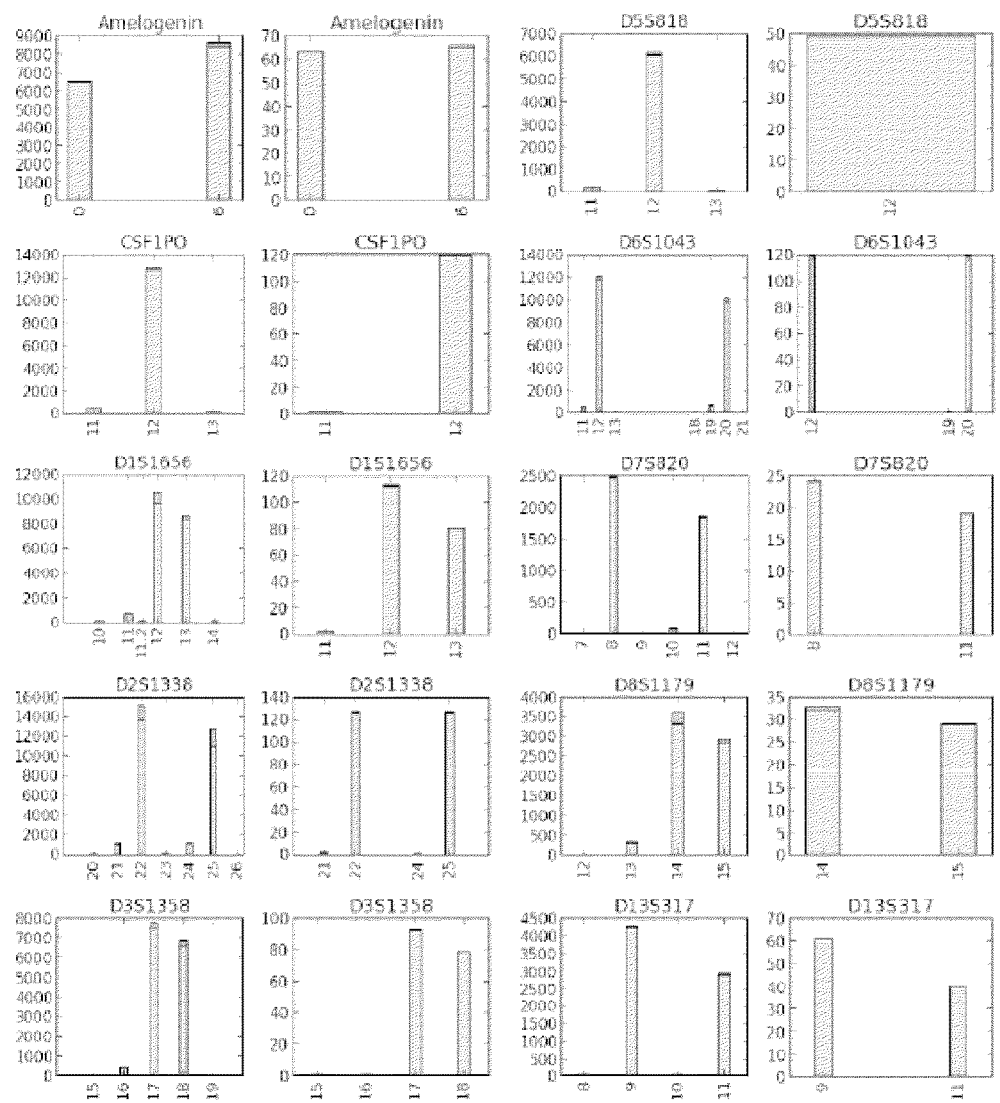
FIG. 9 shows bar graphs of samples analyzed without UMIs, and with UMIs. The left panel for each set represents samples analyzed without UMIs and the right panel for each set represents samples analyzed with UMIs. The X axis designates the repeat number of the STR and the Y axis designates the count number of the particular allele. The error lines within the bars separate the sequencing error (upper part of the bar) from the correct sequence (lower part of the bar) within the STR sequence.
Figure 9:
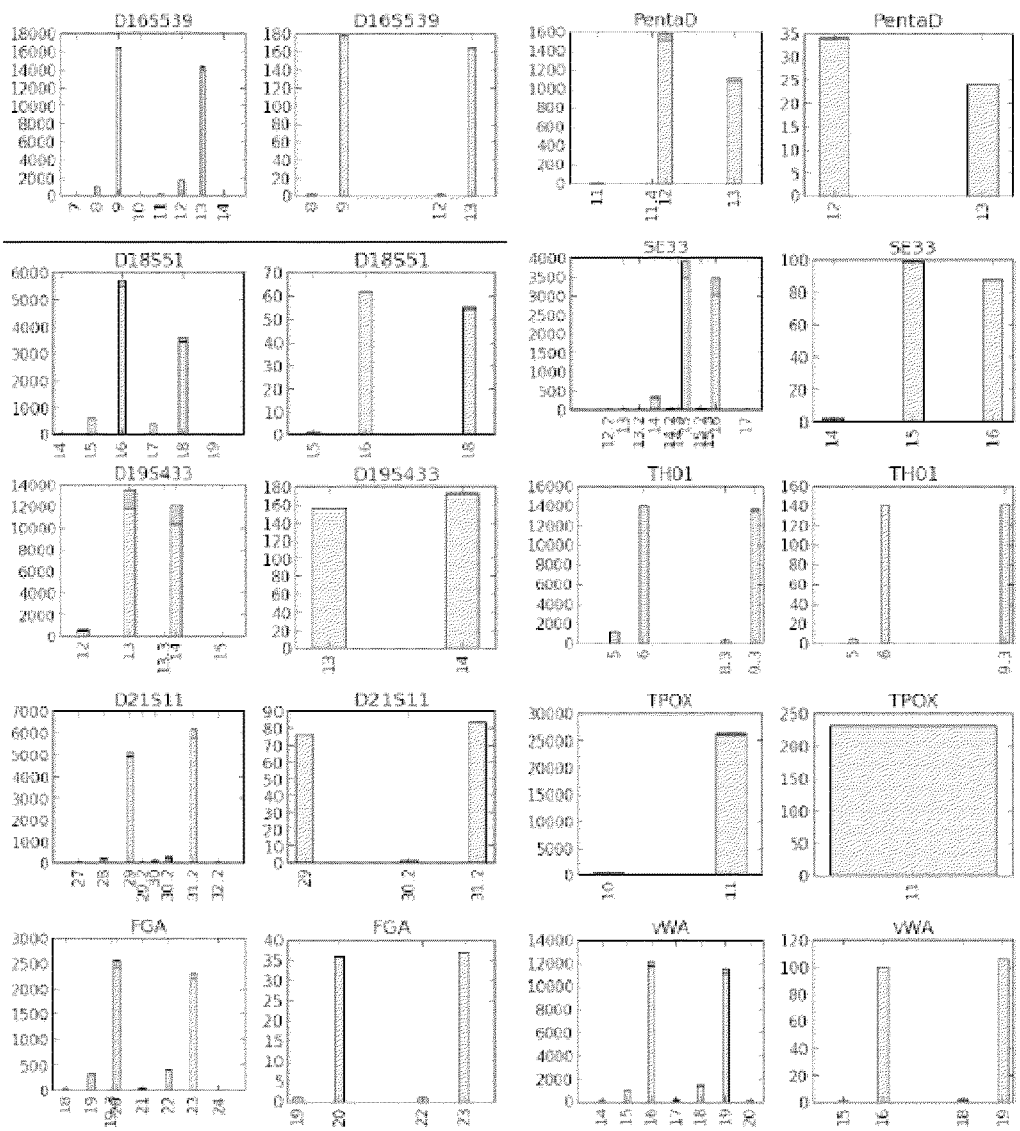
Figure 11:
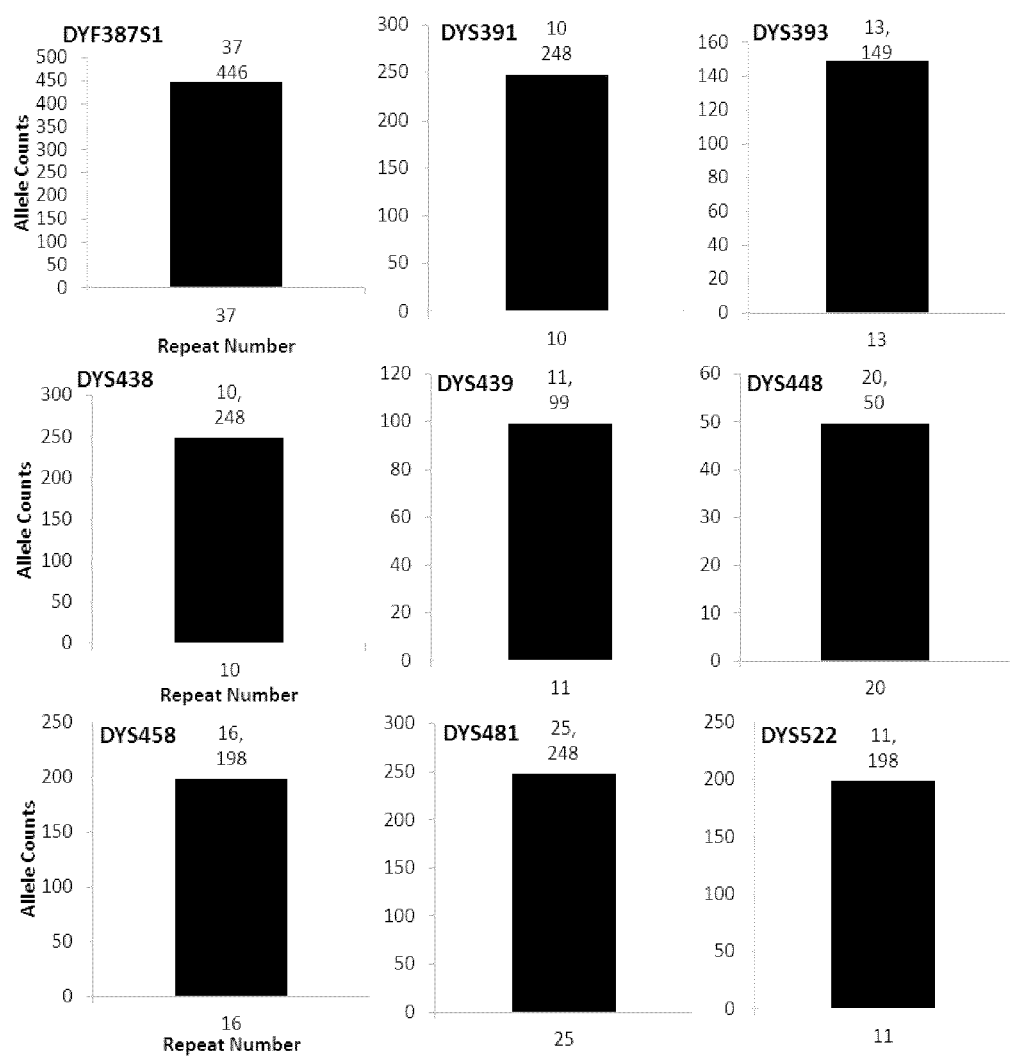
FIG. 11 shows bar charts that show that STR loci specific to the Y chromosome were detected in the experiment of FIG. 9, further demonstrating that the present application can detect contaminating male DNA and specific STR loci from that male DNA whereas two experiments would need to be run with the current CE methodologies to do so.
Figure 11:
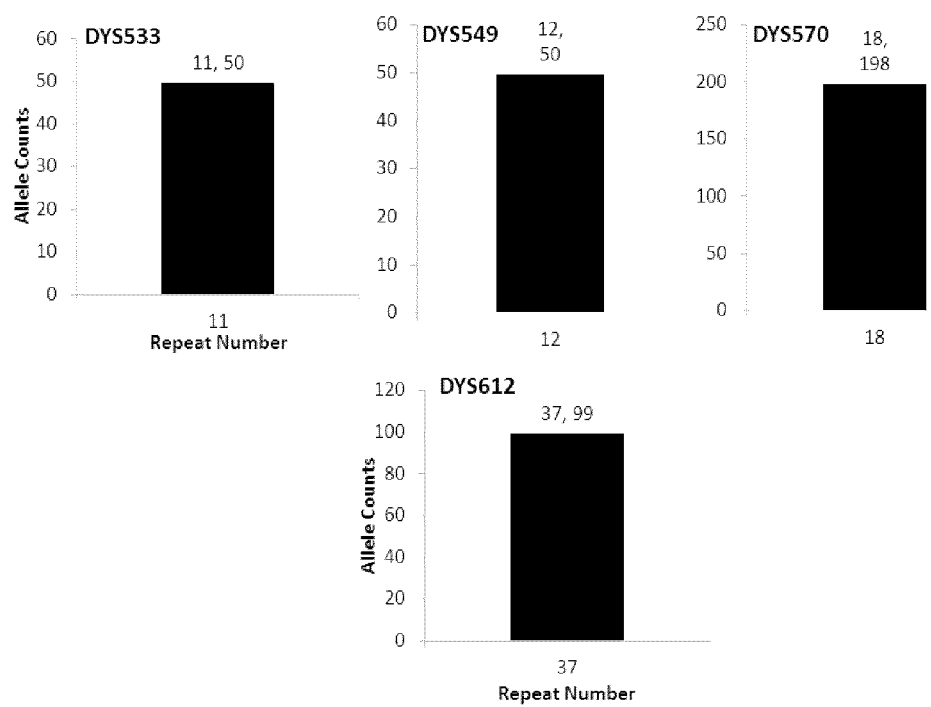

One result that was generated by these studies was that stutter was shown to be a PCR artifact. This has been hypothesized by many investigators (and polymerase slippage has been indicated in human colon cancers), but this hasn't been demonstrated for the Forensics assays. The UMIs can be used to show that stutter is indeed a PCR artifact. The products with n+1 or n−1 repeats have the same UMIs as the products with the correct number of repeats (FIG. 9). In FIG. 9A each locus shows the results without UMI correction compared to FIG. 9B where UMI correction is performed. As demonstrated, without UMI correction the balance between the alleles is not as good as when UMI correction is performed. Further, there is considerably more stutter that is apparent without UMI correction. The portion of the bar above the inter-bar line represents the sequencing error whereas below the line represents the correct sequence within the STR sequence. The error is greatly reduced with UMI correction. For example, SE33 locus has error that is removed with UMI correction. Error correction can be extremely important for criminal casework to provide the most accurate DNA profiling possible.

Example 4—DNA Profiling Using 12 Sample Individuals

Methods and Materials

DNA from 12 sample individuals (Sample #: 1, 3, 4, 5, 6, 7, 10, 13, 14, 15, 16, 17) and one reference genome (2800M) was tested following the workflow of FIG. 3. This experiment incorporates UMIs into the STR primers as described in Example 3. Two replicates of each sample were analyzed with the Illumina® ForenSeq DNA Signature Library Prep Kit on the MiSeq sequencer. One ng DNA was used for each replication using the DNA Primer Mix B: Collected samples mix, which contains primers for 61 STRs plus Amelogenin, 95 identity-informative SNPs, 56 ancestry-informative SNPs, 22 phenotypic-informative SNPs (2 ancestry SNPs are also used for phenotype prediction).

Default Settings

STR: analytical threshold=6.5%; interpretation threshold=15%. SNP: analytical threshold=3%; interpretation threshold=15%.

Figure 16C:
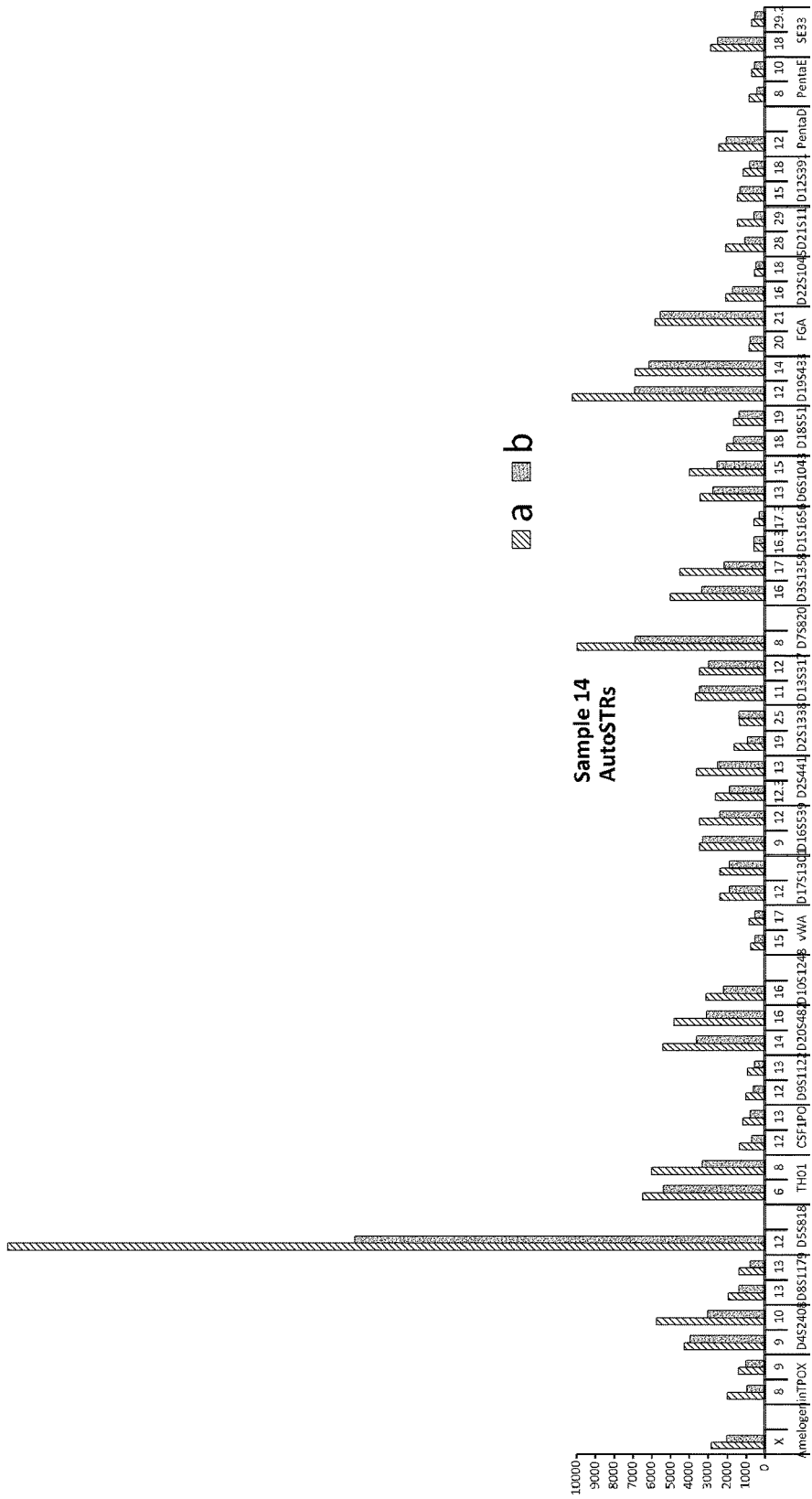
Figures 16D, 16E:
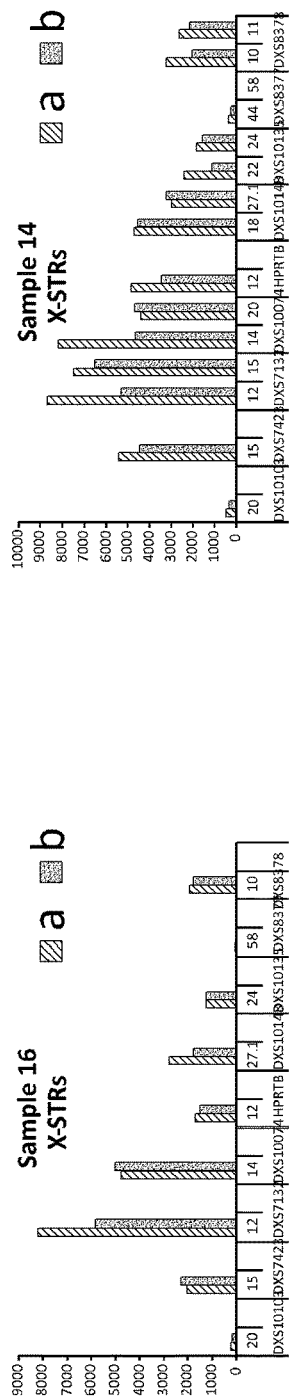
Figure 17A:
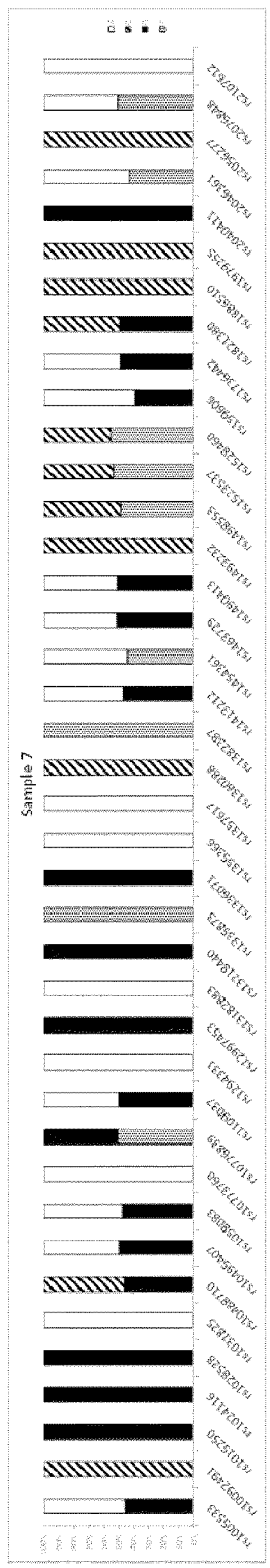
FIG. 17A and FIG. 17B are bar charts showing exemplary SNP plots from the experiment of FIG. 12.
Figure 17B:
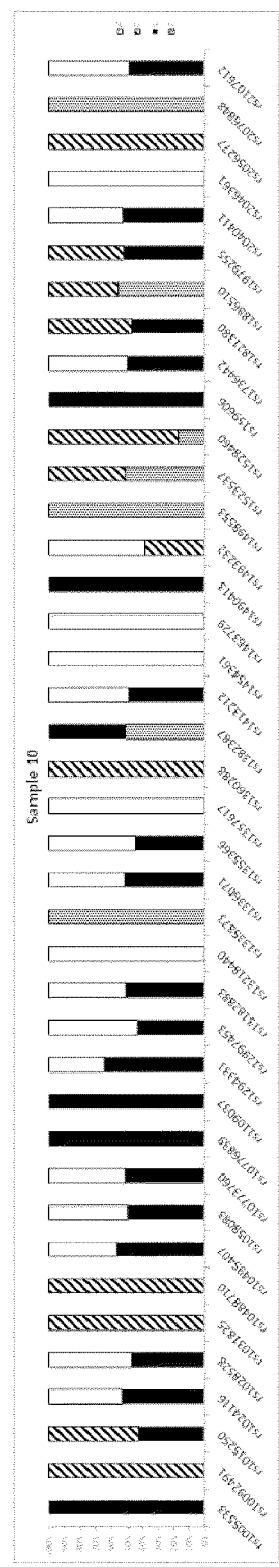

The high level sequencing calls, such as coverage and loci called, for the DNA profiling of the 12 sample individuals are shown in FIG. 12. As can be seen, every locus was covered by at least 100,000 reads in both replications. Only two samples resulted in a failed STR call (1 out of 61). All of the 173 SNPs were successfully called in all individuals in both replications. Sample STR calls of two sample individuals are shown in FIG. 16. Sample SNP calls of two sample individuals are shown in FIG. 17. FIG. 13 shows the population statistics, such as the random match probability (RMP) of the National Institute of Standards and Technology (NIST) auto-STRs, 95% confidence haplotype frequency of NIST Y-STRs, RMP of the dbSNP iSNPs, and the RMP of the STRs from the U.S. Y-STR database.

Phenotypes, such as eye color and hair color of the 12 sample individuals and the reference individual were predicted based on the genotype of pSNPs in the experiment, and compared to the self-reported phenotypes (FIG. 14). High degree of correlation between the predicted and reported phenotypes was observed.

Figure 15:
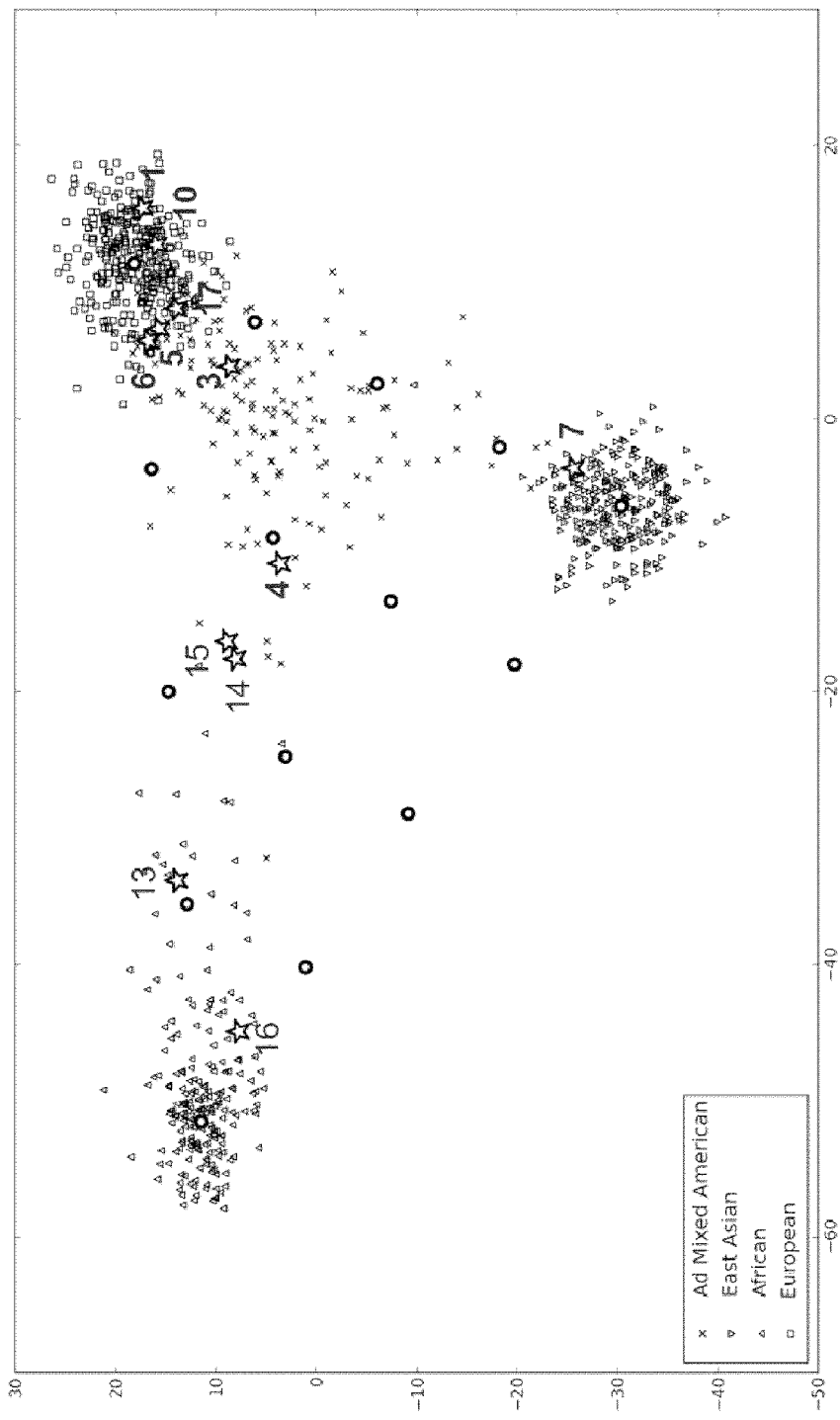
FIG. 15 is a graph showing exemplary ancestry mapping based on genotype of aSNPs from the experiment shown in FIG. 12.

Ancestry of the 12 sample individuals were predicted using the genotype of 56 aSNPs in the experiment. PCA1 and PCA3 scores of each sample individual were calculated, and plotted against reference samples on an ancestry plot. As shown in FIG. 15, ancestry of the sample individuals can be predicted based on the location on the ancestry plot. Fourteen centroid points were included in the ancestry plot (circles). Based on the closest centroid point, the ancestry of each sample individual was predicted.

Figures 18A, 18B:
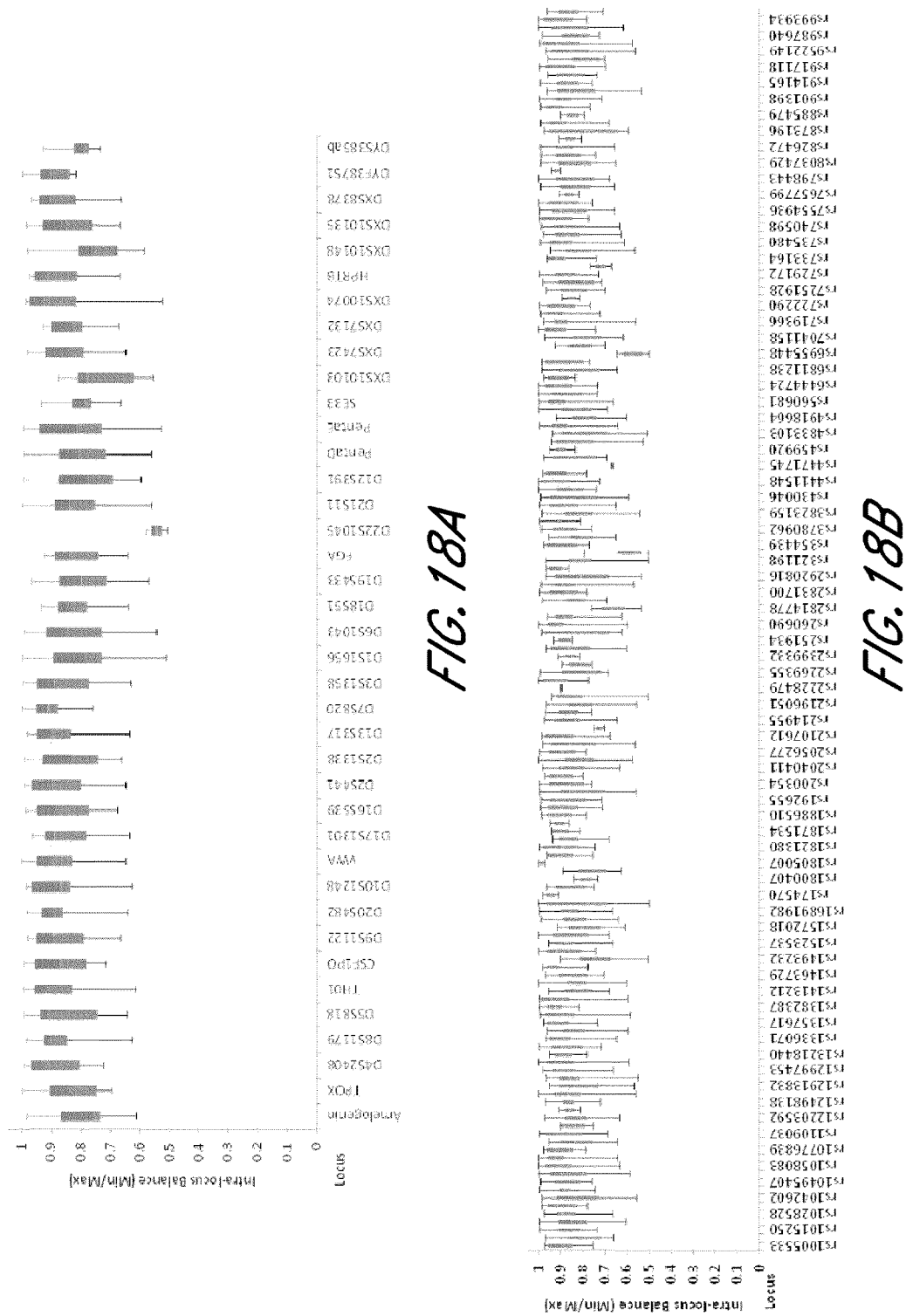
FIG. 18A and FIG. 18B show box plots showing the intra-locus balance of exemplary STR and SNP loci from the experiment of FIG. 12.
Figure 19A:
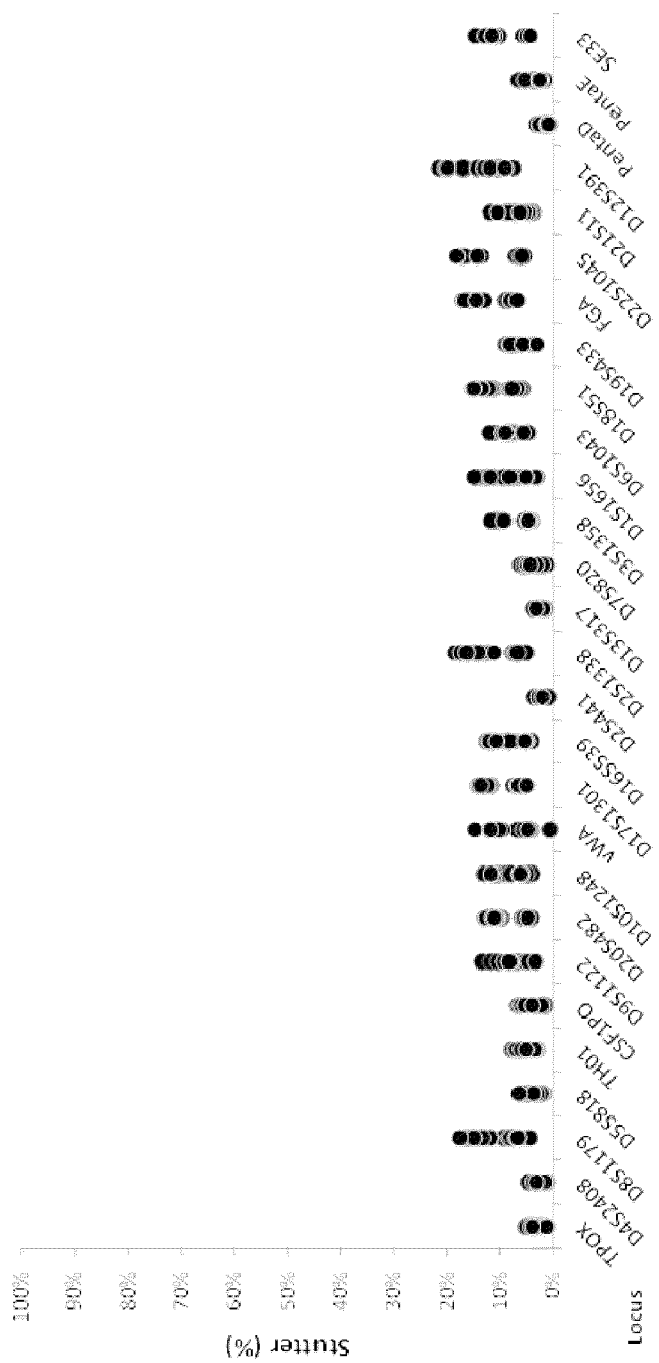
FIG. 19A and FIG. 19B are graphs showing stutter analysis of exemplary STR loci from the experiment of FIG. 12.
Figure 19B:
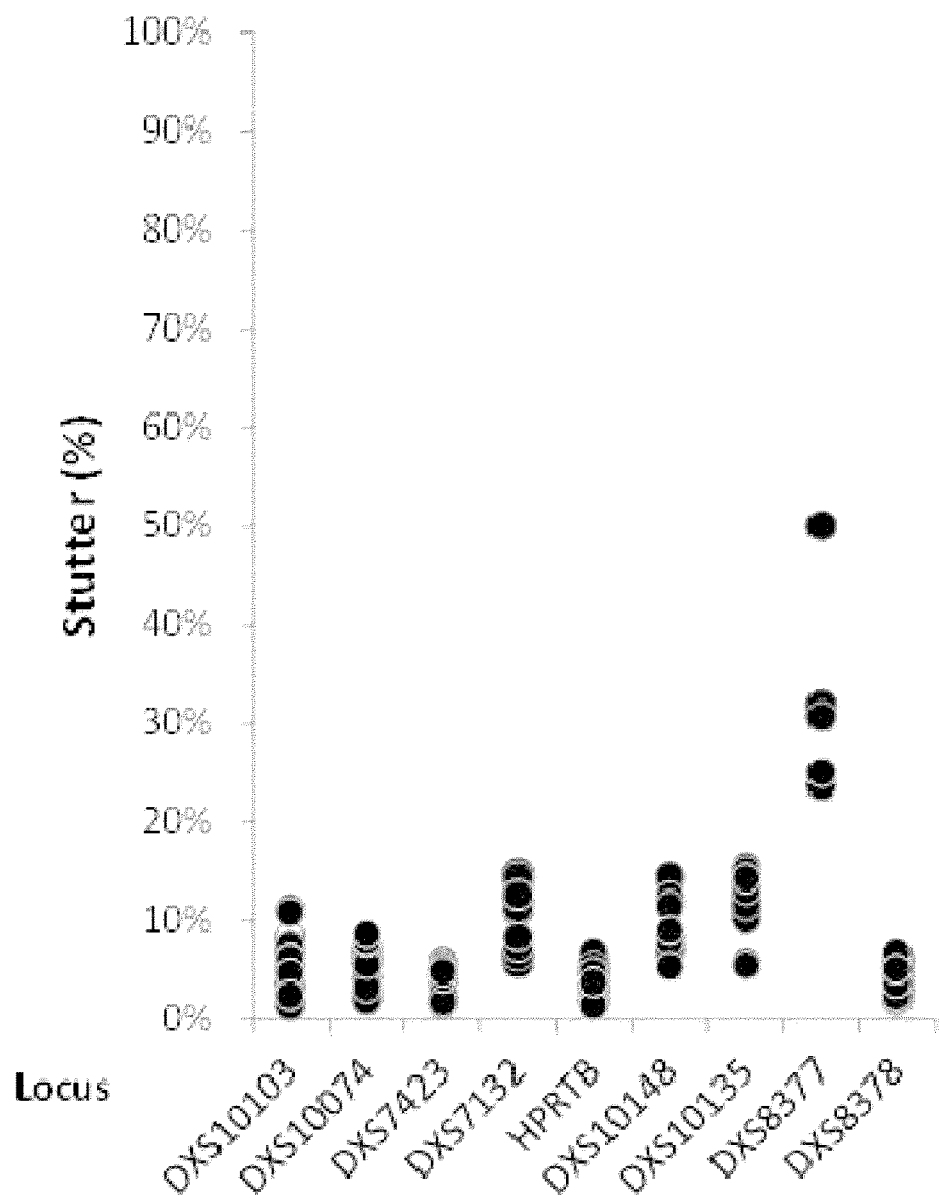

The DNA profiling experiment also showed high level of intra-locus balance in both the STR loci and the SNP loci, as can be seen in FIG. 18, and low level of stutter, as can be seen in FIG. 19.

Figure 21:
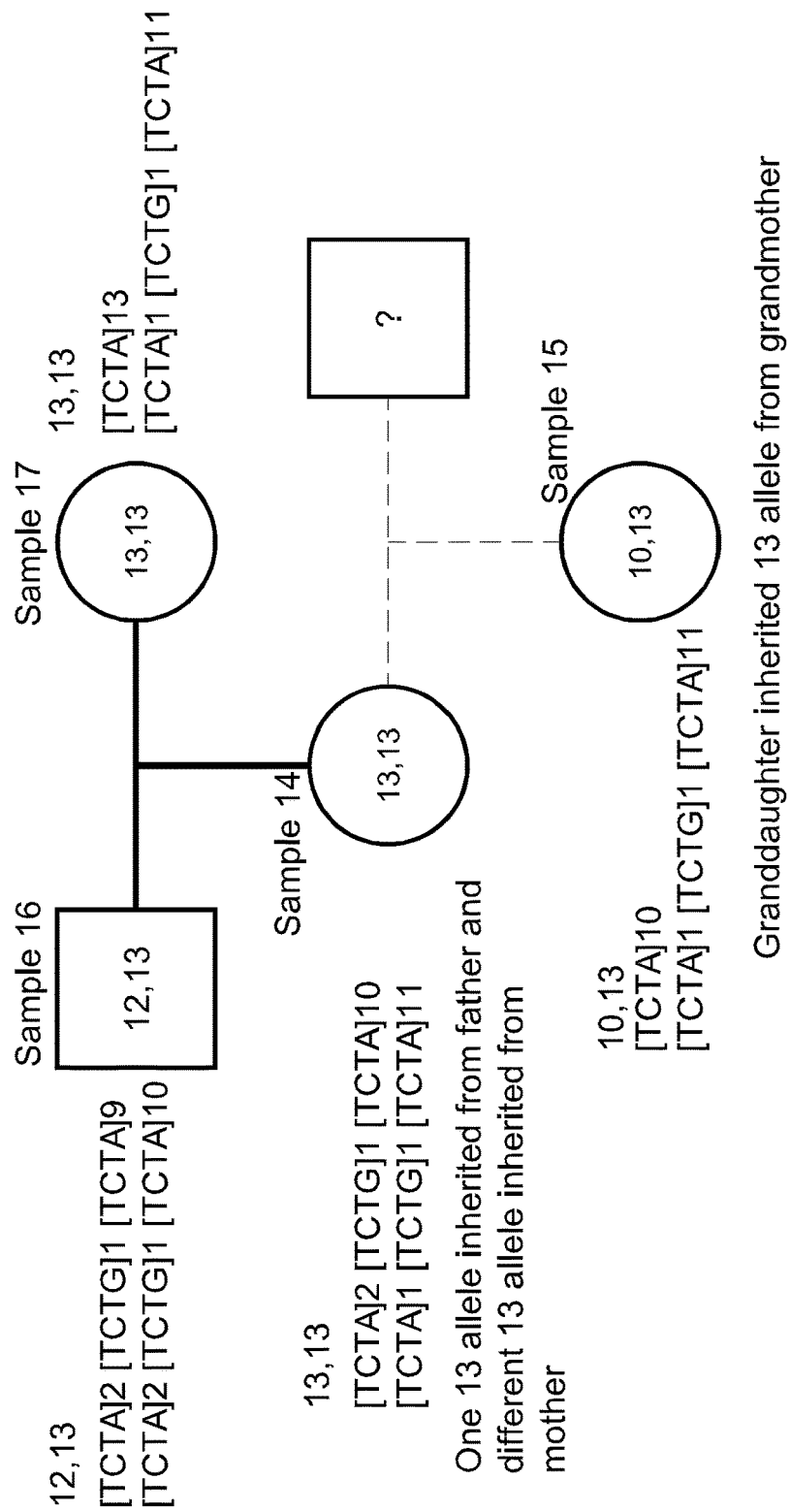
FIG. 21 is a block diagram that shows an exemplary inheritance plot based on variants within the STR D8S1179 from the experiment of FIG. 12. Sequences represented include [TCTA]2 [TCTG]1 [TCTA]9 (SEQ ID NO:421); [TCTA]2 [TCTG]1 [TCTA]10 (SEQ ID NO:422); [TCTA] 13 (SEQ ID NO:423); [TCTA]1 [TCTG]1 [TCTA]11 (SEQ ID NO:424); [TCTA]10 (SEQ ID NO:425).
Figure 22:
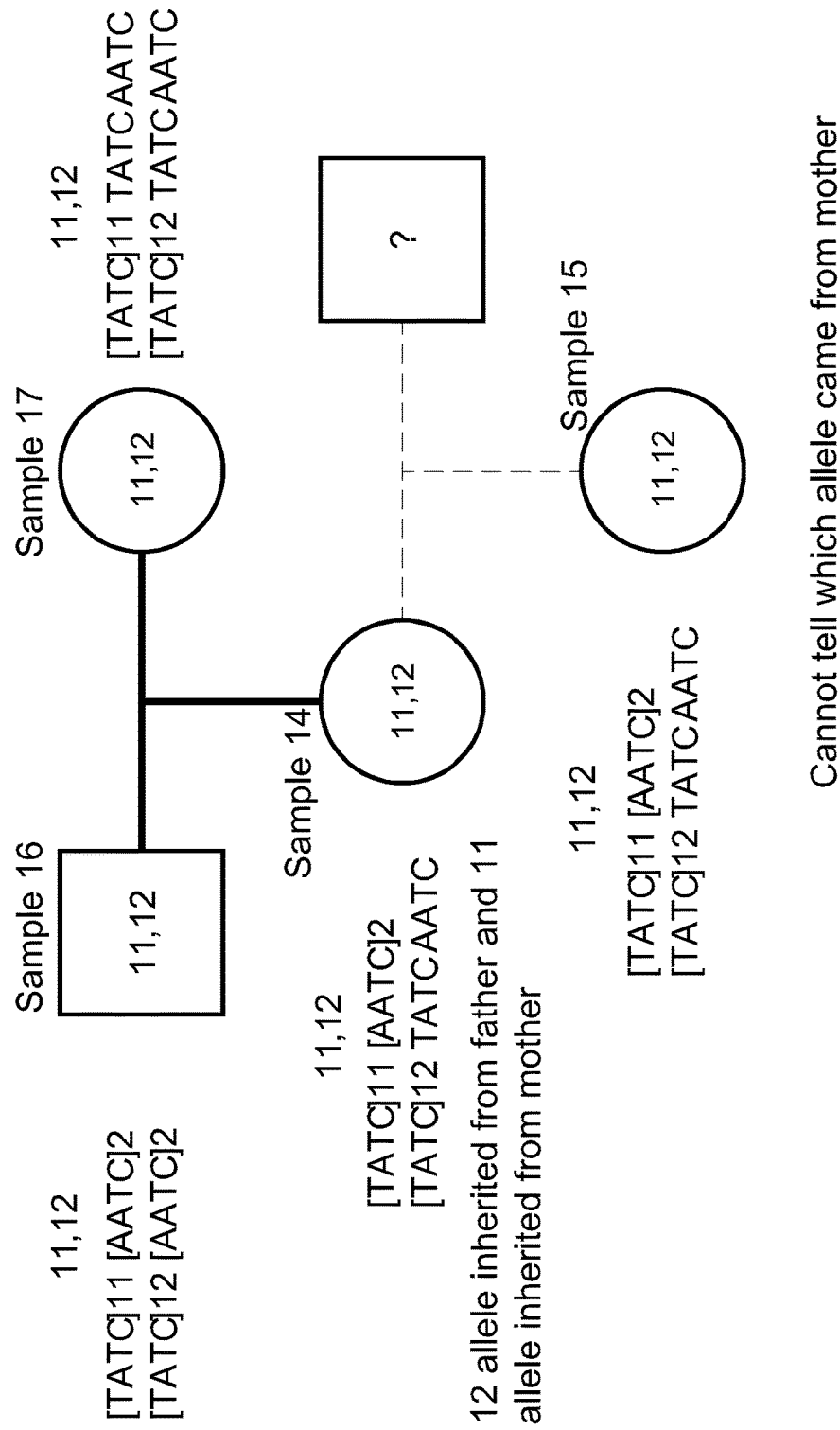
FIG. 22 is a block diagram that shows an exemplary inheritance plot based on variants within the STR D13S317 from the experiment of FIG. 12. Sequences represented include [TATC]11 [AATC]2 (SEQ ID NO:426); [TATC]12

Six of the 12 individuals plus 2800M have at least one isometric heterozygote locus, which is shown in FIG. 20. An isometric heterozygote locus is defined as an STR that has the same repeat number, two different sequences, which are equally balanced. Using the information on the variants in the STR D8S1179, the 13 allele of Sample 15 was traced to the grandmother, Sample 17 (FIG. 21). Similar variant information in the STR D13S317 was used to trace the alleles of Sample 15. However, in this case the origin of either allele cannot be ascertained (FIG. 22).

Example 5—DNA Profiling for Research, Forensic, or Paternity Use

This example is based on the workflow described in ForenSeq™ DNA Signature Prep Guide (Illumina, San Diego, Calif.), the content of which is hereby incorporated by reference in its entirety.

Either purified DNA or crude lysate may be used for this example. For purified DNA, each 1 ng sample is diluted to 0.2 ng/μl with nuclease-free water. For crude lysate, each 2 μl sample is diluted with 3 μl nuclease-free water. A Master Mix is set up for eight or more reactions. For each reaction, 5.4 μl of ForenSeq PCR1 Reaction Mix, 0.4 μl of ForenSeq Enzyme Mix and 5.8 μl of DNA primer Mix (A or B) are added into a 1.5 ml microcentrifuge tube. 10 μl of Master Mix is transferred to each well of the PCR plate, and the DNA or lysate is added. The multiplex reaction mixture is subjected PCR following the protocol:
98 degrees C. for 3 min.
8 cycles of:
  96 degrees C. for 45 sec.
  80 degrees C. for 30 sec.
  54 degrees C. for 2 min., with specified ramping mode
  68 degrees C. for 2 min., with specified ramping mode 10 cycles of:
  96 degrees C. for 30 sec.
  68 degrees C. for 3 min., with specified ramping mode 68 degrees C. for 10 min.
Hold at 10 degrees C.

After cycling, the samples are removed from the thermal cycler. ForenSeq PCR2 Reaction Mix is added to the samples with a pair of adapters (i7 and i5 adapters) and cycled for a 15 cycles, following the protocol:
98 degrees C. for 30 sec.
15 cycles of:
  98 degrees C. for 20 sec.
  66 degrees C. for 30 sec.
  68 degrees C. for 90 sec.
68 degrees C. for 10 min.
Hold at 10 degrees C.

The samples are purified with Sample Purification Beads, and the libraries are normalized and pooled by volume. The pooled libraries are diluted in Hybridization Buffer (HT1), added with Human Sequencing Control (HSC), and heat denatured in preparation for sequencing.

Example 6—Genotyping with Degraded DNA

FIG. 23 shows genotyping results using sheared and/or DNase-treated DNA representing degraded DNA. As shown, more than 50% STR and SNP loci were correctly called with sheared DNA. A random match probability (RMP) of $10^{-19}$ was achieved with DNA of less than 100 bp. Correct ancestry was also predicted using degraded DNA.

Example 7—Genotyping Sensitivity

FIGS. 24 and 25 show genotyping sensitivity results at sub-nanogram DNA input levels from 7.82 pg to 1 ng. As shown, 100% alleles were successfully called at 125 ng input DNA for both STR and SNP. More than 50% alleles were successfully called at as low as 7.82 pg input DNA. Intra-locus balance was greater than 70% for most loci at 1 ng input DNA.

All numbers expressing quantities of ingredients, reaction conditions, and the like used in the specification are to be understood as being modified in all instances by the term "about". Accordingly, unless indicated to the contrary, the numerical parameters set forth therein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Citation of the above publications or documents is not intended as an admission that any of the foregoing is pertinent prior art, nor does it constitute any admission as to the contents or date of these publications or documents.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention. The various embodiments of the invention should be understood that they have been presented by way of example only, and not by way of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

Terms and phrases used in this document, and embodiments thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless apparent from the context or expressly stated otherwise. Similarly, a group of items linked with the conjunction "or" should not be read as requiring mutual exclusivity among that group, but rather should also be read as "and/or" unless it is apparent from the context or expressly stated otherwise. Furthermore, although items, elements or components of the invention may be described or claimed in the singular, the plural is contemplated to be within the scope thereof unless limitation to the singular is explicitly stated. For example, "at least one" may refer to a single or plural and is not limited to either. The presence of broadening words and phrases such as "one or more," "at least," "but not limited to", or other like phrases in some instances shall not be read to mean that the narrower case is intended or required in instances where such broadening phrases may be absent.

What is claimed is:

1. A composition of primers, comprising:
a first primer set comprising primers that specifically hybridize to a first target sequence and amplify a first fragment having a first fragment length, wherein the first target sequence comprises a single nucleotide polymorphism (SNP), and wherein the primers that specifically hybridize to the first target sequence hybridize to a portion of the first target sequence that flanks the SNP and do not hybridize to the SNP; and
a second primer set comprising primers that specifically hybridize to a second target sequence and amplify a second fragment having a second fragment length, wherein the first fragment length is shorter than the second fragment length, and wherein the second target sequence comprises a tandem repeat; and
wherein at least one of the primers in the composition comprising the first and second primer sets comprises one or more tag sequences, and wherein at least one of the primers in the composition has a low melting temperature, has a length of at least 24 nucleotides, comprises a homopolymer nucleotide sequence, or a combination thereof, and wherein at least one of the primers in the composition has a low melting temperature and has a length of at least 24 nucleotides.

2. The composition of claim 1, wherein the one or more tag sequences further comprise a primer tag, a capture tag, a sequencing tag, a unique molecular identifier tag, or a combination thereof.

3. The composition of claim 1, wherein at least one of the primers in the first primer set has a length of at least 24 nucleotides.

4. The composition of claim 1, wherein the low melting temperature is a temperature that is less than 60 degrees C.

5. The composition of claim 1, wherein the first primer set further comprises additional primers that specifically hybridize to one or more additional target sequences collectively comprising at least 29 SNPs.

6. The composition of claim 1, wherein the tandem repeat is a short tandem repeat (STR), an intermediate tandem repeat (ITR), or a variant thereof.

7. The composition of claim 1, wherein the second primer set further comprises additional primers that specifically hybridize to one or more additional target sequences collectively comprising at least 23 tandem repeat sequences.

8. The composition of claim 1, wherein at least one of the primers in the composition of primers has a length of between 24 and 38 nucleotides.

9. The composition of claim 1, wherein at least one of the primers in the composition of primers has a melting temperature that is less than 58 degrees C.

10. The composition of claim 1, wherein at least one of the primers in the composition of primers has a melting temperature of about 54 degrees C.

* * * * *